(12) United States Patent
Ehrenreich et al.

(10) Patent No.: US 11,583,661 B2
(45) Date of Patent: Feb. 21, 2023

(54) DEVICES AND METHODS FOR FLUID TRANSFER THROUGH A PLACED PERIPHERAL INTRAVENOUS CATHETER

(71) Applicant: Velano Vascular, Inc., San Francisco, CA (US)

(72) Inventors: Kevin J. Ehrenreich, San Francisco, CA (US); Pitamber Devgon, Philadelphia, PA (US); Richard T. Briganti, Bala Cynwyd, PA (US); Brian J. Funk, San Francisco, CA (US)

(73) Assignee: Velano Vascular, Inc., San Francisco, CA (US)

( * ) Notice: Subject to any disclaimer, the term of this patent is extended or adjusted under 35 U.S.C. 154(b) by 33 days.

(21) Appl. No.: 17/378,023

(22) Filed: Jul. 16, 2021

(65) Prior Publication Data

US 2021/0338980 A1 Nov. 4, 2021

Related U.S. Application Data

(62) Division of application No. 15/927,509, filed on Mar. 21, 2018, now Pat. No. 11,090,461.

(Continued)

(51) Int. Cl.
*A61M 25/01* (2006.01)
*A61B 5/15* (2006.01)
(Continued)

(52) U.S. Cl.
CPC ......... *A61M 25/0113* (2013.01); *A61B 5/153* (2013.01); *A61B 5/15003* (2013.01);
(Continued)

(58) Field of Classification Search
CPC .......... A61M 25/0113; A61M 25/0023; A61M 2025/0004; A61M 2025/0681;
(Continued)

(56) References Cited

U.S. PATENT DOCUMENTS 3,262,448 A 7/1966 Ring et al.
3,766,913 A 10/1973 Moorehead et al.
(Continued)

FOREIGN PATENT DOCUMENTS

CN 103906470 A 7/2014
CN 104254360 A 12/2014
(Continued)

OTHER PUBLICATIONS

Blood Sampling Hemolysis Study for the MaxPlus TM Positive Flow Connector, Maximus Medical Products, Inc. © 2003, 1 page.
(Continued)

*Primary Examiner* — Dung T Ulsh
(74) *Attorney, Agent, or Firm* — The Webb Law Firm

(57) ABSTRACT

An apparatus includes a catheter, an introducer, and an actuator. A distal end portion of the introducer is configured to couple to an indwelling peripheral intravenous line. The actuator is movably coupled to the introducer and is configured to move the catheter between a first position, in which the catheter is disposed within the introducer, and a second position, in which a distal end portion of the catheter is distal to the introducer. A first portion of the actuator is disposed outside of the introducer and in contact with an outer surface of the introducer such that (1) a longitudinal axis defined by a second portion of the actuator is nonparallel to a longitudinal axis defined by the introducer and (2) the second portion of the actuator exerts a force on a proximal end portion of the catheter operable to increase an internal stress with in a portion of the catheter.

6 Claims, 26 Drawing Sheets

Related U.S. Application Data

(60) Provisional application No. 62/474,202, filed on Mar. 21, 2017.

(51) Int. Cl.
  *A61B 5/153* (2006.01)
  *A61M 25/06* (2006.01)
  *A61M 25/00* (2006.01)

(52) U.S. Cl.
  CPC .. *A61B 5/150641* (2013.01); *A61B 5/150748* (2013.01); *A61B 5/150992* (2013.01); *A61B 5/150389* (2013.01); *A61B 5/150503* (2013.01); *A61M 25/0023* (2013.01); *A61M 2025/0004* (2013.01); *A61M 2025/0681* (2013.01)

(58) Field of Classification Search
  CPC .......... A61B 5/15003; A61B 5/150641; A61B 5/150748; A61B 5/150992; A61B 5/153; A61B 5/150389; A61B 5/150503
  See application file for complete search history.

(56) References Cited

U.S. PATENT DOCUMENTS

| | | | |
|---|---|---|---|
| 3,835,854 A | 9/1974 | Jewett | |
| 4,068,659 A | 1/1978 | Moorehead | |
| 4,159,022 A * | 6/1979 | Pevsner | A61M 25/0122 604/159 |
| 4,192,319 A | 3/1980 | Hargens et al. | |
| 4,314,555 A | 2/1982 | Sagae | |
| 4,342,313 A | 8/1982 | Chittenden | |
| 4,468,224 A | 8/1984 | Enzmann et al. | |
| 4,578,063 A | 3/1986 | Inman et al. | |
| 4,705,511 A | 11/1987 | Kocak | |
| 4,790,830 A | 12/1988 | Hamacher | |
| 4,808,158 A | 2/1989 | Kreuzer et al. | |
| 4,808,165 A | 2/1989 | Carr | |
| 4,935,010 A | 6/1990 | Cox et al. | |
| 4,976,697 A | 12/1990 | Walder et al. | |
| 5,013,304 A | 5/1991 | Russell et al. | |
| 5,057,092 A | 10/1991 | Webster, Jr. | |
| 5,069,674 A | 12/1991 | Fearnot et al. | |
| 5,100,390 A | 3/1992 | Lubeck et al. | |
| 5,135,502 A | 8/1992 | Koenig, Jr. et al. | |
| 5,147,334 A | 9/1992 | Moss | |
| 5,176,647 A | 1/1993 | Knoepfler | |
| 5,201,722 A | 4/1993 | Moorehead et al. | |
| 5,203,771 A | 4/1993 | Melker et al. | |
| 5,254,107 A | 10/1993 | Soltesz | |
| 5,270,003 A | 12/1993 | Bernes et al. | |
| 5,360,407 A | 11/1994 | Leonard | |
| 5,368,029 A | 11/1994 | Holcombe et al. | |
| 5,405,323 A | 4/1995 | Rogers et al. | |
| 5,415,636 A | 5/1995 | Forman | |
| 5,552,118 A | 9/1996 | Mayer | |
| 5,553,625 A | 9/1996 | Rao | |
| 5,562,631 A | 10/1996 | Bogert | |
| 5,603,706 A | 2/1997 | Wyatt et al. | |
| 5,611,782 A | 3/1997 | Haedt | |
| 5,658,263 A | 8/1997 | Dang et al. | |
| 5,704,914 A | 1/1998 | Stocking et al. | |
| 5,713,876 A | 2/1998 | Bogert et al. | |
| 5,749,857 A | 5/1998 | Cuppy | |
| 5,755,709 A | 5/1998 | Cuppy | |
| 5,807,350 A | 9/1998 | Diaz | |
| 5,810,835 A | 9/1998 | Ryan et al. | |
| 5,827,229 A | 10/1998 | Auth et al. | |
| 5,848,996 A | 12/1998 | Eldor | |
| 5,853,393 A | 12/1998 | Bogert | |
| 5,897,537 A | 4/1999 | Berg et al. | |
| 5,911,715 A | 6/1999 | Berg et al. | |
| 5,944,690 A | 8/1999 | Falwell et al. | |
| 5,944,695 A | 8/1999 | Johnson et al. | |
| 6,036,677 A | 3/2000 | Javier et al. | |
| 6,059,759 A | 5/2000 | Mottola et al. | |
| 6,080,138 A | 6/2000 | Lemke et al. | |
| 6,093,177 A | 7/2000 | Javier et al. | |
| 6,126,618 A | 10/2000 | Bischof | |
| 6,197,001 B1 | 3/2001 | Wilson et al. | |
| 6,213,978 B1 | 4/2001 | Voyten | |
| 6,394,979 B1 | 5/2002 | Forman et al. | |
| 6,508,790 B1 | 1/2003 | Lawrence | |
| 6,533,772 B1 | 3/2003 | Sherts et al. | |
| 6,585,703 B1 | 7/2003 | Kassel et al. | |
| 6,648,835 B1 | 11/2003 | Shemesh | |
| 6,652,507 B2 | 11/2003 | Pepin | |
| 6,685,664 B2 | 2/2004 | Levin et al. | |
| 6,692,473 B2 | 2/2004 | St Cyr et al. | |
| 6,712,790 B1 | 3/2004 | Prestidge et al. | |
| 6,719,726 B2 | 4/2004 | Meng et al. | |
| 6,719,781 B1 | 4/2004 | Kim | |
| 6,722,370 B1 | 4/2004 | Mann | |
| 6,726,675 B1 | 4/2004 | Beyar | |
| 6,755,812 B2 | 6/2004 | Peterson et al. | |
| 6,858,024 B1 | 2/2005 | Berg et al. | |
| 6,872,193 B2 | 3/2005 | Shaw et al. | |
| 6,908,459 B2 | 6/2005 | Harding et al. | |
| 6,913,595 B2 | 7/2005 | Mastorakis | |
| 7,008,404 B2 | 3/2006 | Nakajima | |
| 7,087,047 B2 | 8/2006 | Kraus et al. | |
| 7,135,008 B2 | 11/2006 | O'Mahony et al. | |
| 7,252,654 B2 | 8/2007 | VanTassel et al. | |
| 7,311,689 B2 | 12/2007 | Levin et al. | |
| 7,316,678 B2 | 1/2008 | Nash et al. | |
| 7,462,161 B2 | 12/2008 | O'Mahony et al. | |
| 7,615,033 B2 | 11/2009 | Leong | |
| 7,625,367 B2 | 12/2009 | Adams et al. | |
| 7,662,110 B2 | 2/2010 | Flaherty | |
| 7,670,320 B2 | 3/2010 | Iwase et al. | |
| 7,685,367 B2 | 3/2010 | Ruia et al. | |
| 7,691,088 B2 | 4/2010 | Howell | |
| 7,713,250 B2 | 5/2010 | Harding et al. | |
| 7,717,882 B2 | 5/2010 | Harding | |
| 7,717,899 B2 | 5/2010 | Bowe et al. | |
| 7,762,977 B2 | 7/2010 | Porter et al. | |
| 7,766,961 B2 | 8/2010 | Patel et al. | |
| 7,771,394 B2 | 8/2010 | Shue et al. | |
| 7,892,208 B2 | 2/2011 | Schnell et al. | |
| 7,972,294 B2 | 7/2011 | Nash et al. | |
| 8,048,031 B2 | 11/2011 | Shaw et al. | |
| 8,062,226 B2 | 11/2011 | Moore | |
| 8,092,374 B2 | 1/2012 | Smith et al. | |
| 8,104,475 B2 | 1/2012 | Cheung | |
| 8,114,057 B2 | 2/2012 | Gerdts et al. | |
| 8,162,890 B2 | 4/2012 | Amisar et al. | |
| 8,211,089 B2 | 7/2012 | Winsor et al. | |
| 8,251,978 B2 | 8/2012 | Nash et al. | |
| 8,267,911 B2 | 9/2012 | Gallogly et al. | |
| 8,361,013 B2 | 1/2013 | Wood | |
| 8,361,014 B2 | 1/2013 | Wood | |
| 8,366,685 B2 | 2/2013 | Devgon | |
| 8,372,032 B2 | 2/2013 | Wood | |
| 8,425,532 B2 | 4/2013 | Flom et al. | |
| 8,444,605 B2 | 5/2013 | Kuracina et al. | |
| 8,491,568 B2 | 7/2013 | Schertiger et al. | |
| 8,500,054 B2 | 8/2013 | Grant et al. | |
| 8,506,533 B2 | 8/2013 | Carlyon et al. | |
| 8,523,801 B2 | 9/2013 | Nash et al. | |
| 8,532,730 B2 | 9/2013 | Brister et al. | |
| 8,690,833 B2 | 4/2014 | Belson | |
| 8,696,639 B2 | 4/2014 | Smith et al. | |
| 8,702,658 B2 | 4/2014 | Spearman | |
| 8,721,546 B2 | 5/2014 | Belson | |
| 8,728,035 B2 | 5/2014 | Warring et al. | |
| 8,728,038 B2 | 5/2014 | Spearman | |
| 8,728,058 B2 | 5/2014 | Schertiger | |
| 8,753,312 B2 | 6/2014 | Bowe et al. | |
| 8,808,246 B2 | 8/2014 | Cabot | |
| 8,876,773 B2 | 11/2014 | Ishida | |
| 8,932,259 B2 | 1/2015 | Stout et al. | |
| 8,936,581 B2 | 1/2015 | Bihlmaier | |
| 8,974,411 B2 | 3/2015 | McKinnon | |

(56) References Cited

U.S. PATENT DOCUMENTS

| | | |
|---|---|---|
| 9,028,425 B2 | 5/2015 | Burkholz |
| 9,056,182 B2 | 6/2015 | Moulton et al. |
| 9,084,851 B2 | 7/2015 | Kosinski et al. |
| 9,089,474 B2 | 7/2015 | Cederschiold |
| 9,101,746 B2 | 8/2015 | Stout et al. |
| 9,114,241 B2 | 8/2015 | Stout et al. |
| 9,126,012 B2 | 9/2015 | McKinnon et al. |
| 9,149,604 B2 | 10/2015 | Nishide et al. |
| 9,155,876 B2 | 10/2015 | Sonderegger et al. |
| 9,186,100 B2 | 11/2015 | Devgon |
| 9,198,610 B2 | 12/2015 | Davis et al. |
| 9,233,208 B2 | 1/2016 | Tekeste |
| 9,302,049 B2 | 4/2016 | Tekeste |
| 9,314,201 B2 | 4/2016 | Burkholz et al. |
| 9,352,119 B2 | 5/2016 | Burkholz et al. |
| 9,352,128 B2 | 5/2016 | Ishida |
| 9,358,335 B2 | 6/2016 | Wada et al. |
| 9,381,320 B2 | 7/2016 | Vincent et al. |
| 9,399,112 B2 | 7/2016 | Shevgoor et al. |
| 9,402,975 B2 | 8/2016 | Shevgoor |
| 9,408,569 B2 | 8/2016 | Andreae et al. |
| 9,415,185 B2 | 8/2016 | Notter |
| 9,480,794 B2 | 11/2016 | Keith et al. |
| 9,522,229 B2 | 12/2016 | Sonderegger et al. |
| 9,522,237 B2 | 12/2016 | Alheidt et al. |
| 9,549,701 B2 | 1/2017 | Peterson et al. |
| 9,579,486 B2 | 2/2017 | Burkholz et al. |
| 9,592,374 B2 | 3/2017 | Muse |
| 9,616,214 B2 | 4/2017 | Stout et al. |
| 9,636,278 B2 | 5/2017 | Sanders et al. |
| 9,737,686 B2 | 8/2017 | Trainer et al. |
| 9,744,344 B1 | 8/2017 | Devgon et al. |
| 9,750,446 B2 | 9/2017 | Devgon et al. |
| 9,750,920 B2 | 9/2017 | Vincent et al. |
| 9,750,927 B2 | 9/2017 | Ma |
| 9,750,928 B2 | 9/2017 | Burkholz et al. |
| 9,770,580 B2 | 9/2017 | Burkholz et al. |
| 9,775,972 B2 | 10/2017 | Christensen et al. |
| 9,789,279 B2 | 10/2017 | Burkholz et al. |
| 9,832,412 B2 | 11/2017 | Burkholz et al. |
| 9,839,385 B2 | 12/2017 | Burkholz |
| 9,895,092 B2 | 2/2018 | Burkholz |
| 9,907,913 B2 | 3/2018 | Kosinski et al. |
| 9,909,162 B2 | 3/2018 | Yeh |
| 9,919,826 B2 | 3/2018 | Ivosevic et al. |
| 9,943,676 B2 | 4/2018 | Tekeste |
| 9,980,878 B2 | 5/2018 | Marici et al. |
| 9,993,634 B2 | 6/2018 | Christensen et al. |
| 10,010,685 B2 | 7/2018 | Ferreri et al. |
| 10,039,884 B2 | 8/2018 | Ferreri et al. |
| 10,046,155 B2 | 8/2018 | Carter et al. |
| 10,076,272 B2 | 9/2018 | Devgon et al. |
| 10,105,085 B2 | 10/2018 | Andreae et al. |
| 10,105,494 B2 | 10/2018 | Alheidt et al. |
| 10,112,033 B2 | 10/2018 | Burkholz et al. |
| 10,143,411 B2 | 12/2018 | Cabot |
| 10,154,904 B2 | 12/2018 | Gray et al. |
| 10,182,753 B2 | 1/2019 | Davis et al. |
| 10,219,982 B2 | 3/2019 | Weir et al. |
| 10,232,140 B2 | 3/2019 | McKinnon |
| 10,238,325 B2 | 3/2019 | Burkholz et al. |
| 10,238,852 B2 | 3/2019 | Burkholz et al. |
| 10,245,416 B2 | 4/2019 | Harding et al. |
| 10,300,247 B2 | 5/2019 | Devgon et al. |
| 10,307,571 B2 | 6/2019 | Burkholz |
| 10,350,066 B2 | 7/2019 | Cooper et al. |
| 10,391,031 B2 | 8/2019 | Yevmenenko et al. |
| 2002/0120215 A1 | 8/2002 | Crawford et al. |
| 2003/0083620 A1 | 5/2003 | Luther et al. |
| 2003/0122021 A1 | 7/2003 | McConnell et al. |
| 2003/0225369 A1 | 12/2003 | McMichael et al. |
| 2004/0092879 A1 | 5/2004 | Kraus et al. |
| 2004/0138622 A1 | 7/2004 | Palasis |
| 2004/0176682 A1 | 9/2004 | Murphy |
| 2004/0181192 A1 | 9/2004 | Cuppy |
| 2005/0015048 A1 | 1/2005 | Chiu et al. |
| 2005/0090801 A1 | 4/2005 | Racz et al. |
| 2005/0096609 A1 | 5/2005 | Maginot et al. |
| 2005/0119597 A1 | 6/2005 | O'Mahony et al. |
| 2005/0165355 A1 | 7/2005 | Fitzgerald |
| 2005/0192558 A1 | 9/2005 | Bernard et al. |
| 2005/0197623 A1 | 9/2005 | Leeflang et al. |
| 2005/0245875 A1 | 11/2005 | Restelli et al. |
| 2005/0267327 A1 | 12/2005 | Iizuka et al. |
| 2005/0273076 A1 | 12/2005 | Beasley et al. |
| 2006/0015068 A1* | 1/2006 | Amisar ............ A61M 25/0637 604/164.01 |
| 2006/0100582 A1 | 5/2006 | Marianowicz et al. |
| 2006/0142694 A1 | 6/2006 | Bednarek et al. |
| 2006/0155209 A1 | 7/2006 | Miller et al. |
| 2006/0155244 A1 | 7/2006 | Popov |
| 2007/0088279 A1 | 4/2007 | Shue et al. |
| 2007/0100295 A1 | 5/2007 | Belley et al. |
| 2007/0219460 A1 | 9/2007 | Goldenberg |
| 2007/0282280 A1 | 12/2007 | Tennican |
| 2008/0033396 A1 | 2/2008 | Danek et al. |
| 2008/0045862 A1 | 2/2008 | Dalebout et al. |
| 2008/0097407 A1 | 4/2008 | Plishka |
| 2008/0287918 A1 | 11/2008 | Rosenman et al. |
| 2008/0300574 A1 | 12/2008 | Belson et al. |
| 2008/0319387 A1 | 12/2008 | Amisar et al. |
| 2009/0156963 A1 | 6/2009 | Noble et al. |
| 2009/0192496 A1 | 7/2009 | Suwito et al. |
| 2009/0209912 A1 | 8/2009 | Keyser et al. |
| 2010/0121218 A1 | 5/2010 | Mugan et al. |
| 2010/0160863 A1 | 6/2010 | Heuser |
| 2010/0210934 A1 | 8/2010 | Belson |
| 2010/0286657 A1 | 11/2010 | Heck |
| 2010/0305519 A1 | 12/2010 | McKinnon et al. |
| 2011/0015577 A1 | 1/2011 | Baney et al. |
| 2011/0202123 A1 | 8/2011 | Bonutti |
| 2012/0016307 A1 | 1/2012 | Burkholz et al. |
| 2012/0041392 A1 | 2/2012 | Donawick |
| 2012/0046648 A1 | 2/2012 | Scheckel |
| 2012/0053523 A1 | 3/2012 | Harding et al. |
| 2012/0071856 A1 | 3/2012 | Goldfarb et al. |
| 2012/0109079 A1 | 5/2012 | Asleson et al. |
| 2012/0157968 A1 | 6/2012 | Eldredge et al. |
| 2012/0197200 A1 | 8/2012 | Belson |
| 2012/0277627 A1* | 11/2012 | Devgon ........... A61B 5/150717 600/576 |
| 2013/0006226 A1 | 1/2013 | Hong et al. |
| 2013/0102888 A1 | 4/2013 | Slim |
| 2013/0121897 A1 | 5/2013 | Davis et al. |
| 2013/0131597 A1 | 5/2013 | Blaivas et al. |
| 2013/0197449 A1 | 8/2013 | Franklin |
| 2013/0281925 A1 | 10/2013 | Benscoter et al. |
| 2014/0012085 A1 | 1/2014 | Smith et al. |
| 2014/0107427 A1 | 4/2014 | Chow et al. |
| 2014/0107564 A1 | 4/2014 | Bullington et al. |
| 2014/0107800 A1 | 4/2014 | Flom et al. |
| 2014/0171803 A1 | 6/2014 | Van Hoven et al. |
| 2014/0180127 A1 | 6/2014 | Meyer et al. |
| 2014/0188002 A1 | 7/2014 | Close et al. |
| 2014/0188003 A1 | 7/2014 | Belson |
| 2014/0194833 A1 | 7/2014 | Andrus |
| 2014/0296745 A1 | 10/2014 | Cash |
| 2014/0358120 A1 | 12/2014 | Haarala et al. |
| 2014/0364766 A1 | 12/2014 | Devgon et al. |
| 2014/0378867 A1 | 12/2014 | Belson |
| 2015/0005669 A1 | 1/2015 | Burkholz |
| 2015/0038909 A1 | 2/2015 | Christensen et al. |
| 2015/0051584 A1 | 2/2015 | Korkuch et al. |
| 2015/0065952 A1 | 3/2015 | Pacheco et al. |
| 2015/0119859 A1 | 4/2015 | Cajamarca et al. |
| 2015/0119863 A1 | 4/2015 | Christensen et al. |
| 2015/0123398 A1 | 5/2015 | Sanders et al. |
| 2015/0148747 A1 | 5/2015 | Whitley |
| 2015/0208973 A1 | 7/2015 | Burkholz |
| 2015/0209510 A1 | 7/2015 | Burkholz et al. |
| 2015/0297456 A1 | 10/2015 | Marici et al. |
| 2015/0306345 A1 | 10/2015 | Burkholz et al. |
| 2015/0313526 A1 | 11/2015 | Van Wieren |
| 2015/0320937 A1 | 11/2015 | Kosinski et al. |

(56) References Cited

U.S. PATENT DOCUMENTS

| | | |
|---|---|---|
| 2015/0360005 A1 | 12/2015 | Arellano et al. |
| 2016/0008517 A1 | 1/2016 | Burkholz et al. |
| 2016/0015945 A1 | 1/2016 | Warring et al. |
| 2016/0038067 A1 | 2/2016 | Davis et al. |
| 2016/0073937 A1 | 3/2016 | Burkholz et al. |
| 2016/0121086 A1 | 5/2016 | Castro et al. |
| 2016/0166772 A1 | 6/2016 | Mirzazadeh et al. |
| 2016/0206858 A1 | 7/2016 | Ishida |
| 2016/0220786 A1 | 8/2016 | Mitchell et al. |
| 2016/0220790 A1 | 8/2016 | Borowicz |
| 2016/0256667 A1 | 9/2016 | Ribelin et al. |
| 2016/0367177 A1 | 12/2016 | Edelhauser et al. |
| 2017/0000982 A1 | 1/2017 | Ishida |
| 2017/0043066 A1 | 2/2017 | Laub |
| 2017/0056595 A1 | 3/2017 | Alheidt et al. |
| 2017/0056639 A1 | 3/2017 | Ma |
| 2017/0119997 A1 | 5/2017 | Burkholz et al. |
| 2017/0120001 A1 | 5/2017 | Hyer et al. |
| 2017/0120008 A1 | 5/2017 | Burkholz et al. |
| 2017/0120009 A1 | 5/2017 | Garrison et al. |
| 2017/0120010 A1 | 5/2017 | Burkholz et al. |
| 2017/0120012 A1 | 5/2017 | Sonderegger et al. |
| 2017/0120013 A1 | 5/2017 | Peterson et al. |
| 2017/0120017 A1 | 5/2017 | Burkholz et al. |
| 2017/0273714 A1 | 9/2017 | Harding et al. |
| 2017/0325713 A1 | 11/2017 | Burkholz et al. |
| 2017/0333676 A1 | 11/2017 | Vincent et al. |
| 2017/0368326 A1 | 12/2017 | Burkholz et al. |
| 2018/0021543 A1 | 1/2018 | Burkholz et al. |
| 2018/0093074 A1 | 4/2018 | Burkholz et al. |
| 2018/0093085 A1 | 4/2018 | Burkholz et al. |
| 2018/0272106 A1 | 9/2018 | Funk et al. |
| 2018/0280626 A1 | 10/2018 | Branson et al. |
| 2018/0289920 A1 | 10/2018 | Harding et al. |
| 2018/0318557 A1 | 11/2018 | Burkholz et al. |
| 2018/0339132 A1 | 11/2018 | Brunetti |
| 2018/0353311 A1 | 12/2018 | Cummins et al. |
| 2018/0353729 A1 | 12/2018 | Hu et al. |
| 2019/0022324 A1 | 1/2019 | Tekeste |
| 2019/0054270 A1 | 2/2019 | Bornhoft |
| 2019/0091462 A1 | 3/2019 | Bihlmaier et al. |
| 2019/0167855 A1 | 6/2019 | Burkholz et al. |
| 2019/0167951 A1 | 6/2019 | Harding et al. |
| 2019/0167966 A1 | 6/2019 | Burkholz et al. |
| 2019/0175088 A1 | 6/2019 | Burkholz et al. |
| 2019/0209726 A1 | 7/2019 | Ma et al. |

FOREIGN PATENT DOCUMENTS

| | | |
|---|---|---|
| CN | 105407953 A | 3/2016 |
| CN | 105530983 A | 4/2016 |
| EP | 1191970 B1 | 3/2006 |
| EP | 2504054 B1 | 9/2013 |
| JP | S55119739 U | 8/1980 |
| JP | 2010505534 A | 2/2010 |
| RU | 2087162 C1 | 8/1997 |
| RU | 2452376 C2 | 6/2012 |
| RU | 2556963 C2 | 7/2015 |
| WO | 1996021393 A1 | 7/1996 |
| WO | 1998039054 A1 | 9/1998 |
| WO | 2000041617 A1 | 7/2000 |
| WO | 2004089437 A1 | 10/2004 |
| WO | 2006065949 A2 | 6/2006 |
| WO | 2006126002 A1 | 11/2006 |
| WO | 2008097949 A1 | 8/2008 |
| WO | 2008122008 A1 | 10/2008 |
| WO | 2008130077 A1 | 10/2008 |
| WO | 2008138351 A1 | 11/2008 |
| WO | 2009152470 A1 | 12/2009 |
| WO | 2010065901 A1 | 6/2010 |
| WO | 2010089154 A1 | 8/2010 |
| WO | 2010107949 A1 | 9/2010 |
| WO | 2011011436 A2 | 1/2011 |
| WO | 2011030282 A1 | 3/2011 |
| WO | 2011143621 A1 | 11/2011 |
| WO | 2012064786 A1 | 5/2012 |
| WO | 2013174381 A1 | 11/2013 |
| WO | 2014093472 A1 | 6/2014 |
| WO | 2016089871 A1 | 6/2016 |
| WO | 2016178974 A1 | 11/2016 |
| WO | 2017074674 A1 | 5/2017 |

OTHER PUBLICATIONS

"Collection Tubes Are Used," J Emerg Nurs. Dec. 2004; 30(6):529-33, Retrieved from the Internet <URL: http://www.ienonline.org/article/S0099-1767(04)00634-8/fulltext> , 2 pages.

Connect and Protect with BO Diagnostics—Preanalytical Systems, BO Vacutainer®, Luer-Lok TM, Access Device, 2006, 2 pages.

Evidence-Based Practice (EBP) Guideline Drawing Labs from Peripheral IV Sites, Nursing Research Council of United Hospital—Developed Apr. 2004; Revised Mar. 2009, 3 pages.

Frey, "Drawing Blood Samples From Vascular Access Devices: Evidence-based Practice," Journal of Infusion Nursing: Sep./Oct. 2003, pp. 285-293, vol. 26:5, Article: CE, Abstract, 1 page.

Himberger Jr., "Accuracy of drawing blood through infusing intravenous lines," 2001, Retrieved from the Internet <URL: http://www.ncbi.nlm.nih.gov/pubmed/?term= Accuracy%20of%20drawing%20blood%20through%20infusing%20intravenous%20 lines>.

Jagger, et al., "Drawing Venous Blood With Syringes: A Risky Use of Injection Equipment," Advances in Exposure Prevention, 2000, 3 pages, vol. 5:3.

Needleless IV Access Devices, BO Q-Syte TM, Luer Access Split-Septum, 2007, 1 page.

Vascular Access Procedures, Vascular Access Procedures, Retrieved from the Internet <URL: http://www.radiologyinfo.org/en/info.cfm?pg=vasc_access>, 7 pages.

Velano Vascular, "Introducing PIVO" [Retrieved from the Internet] <URL: http://velanovascular.com/solutions/>, 2017.

WHO guidelines on drawing blood: best practices in phlebotomy, © World Health Organization, 2010, 125 pages.

* cited by examiner

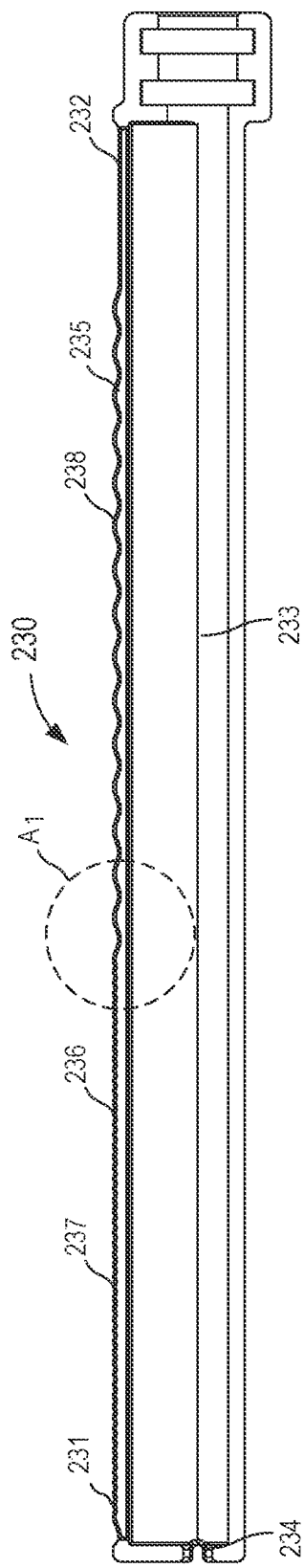
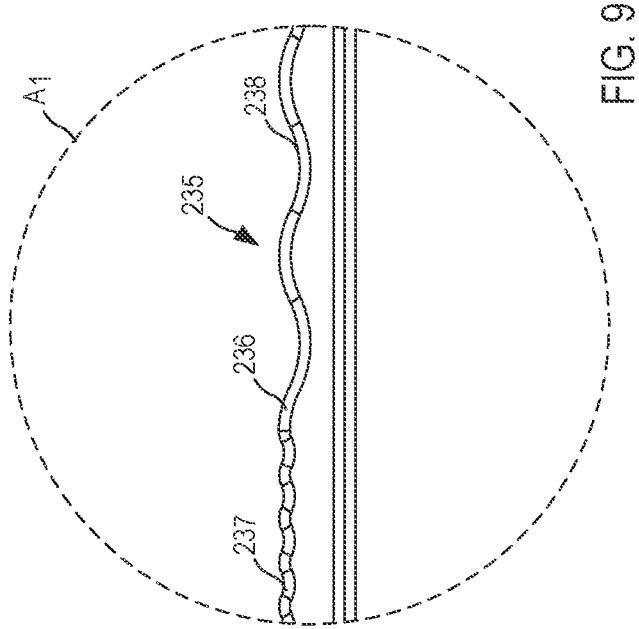
FIG. 8
FIG. 9

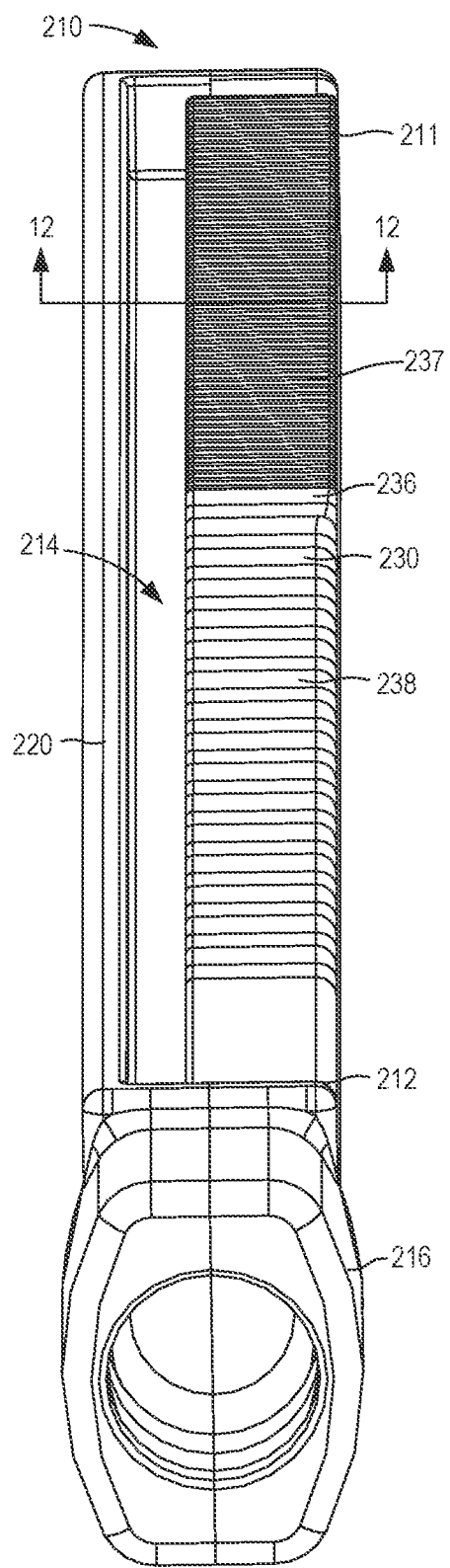
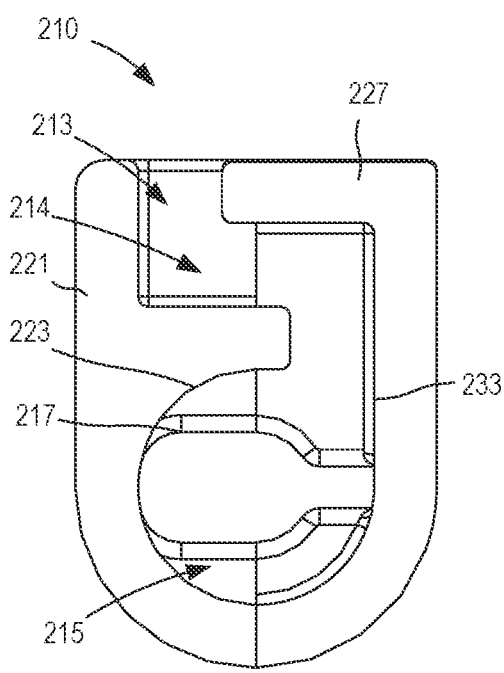
FIG. 11
FIG. 12

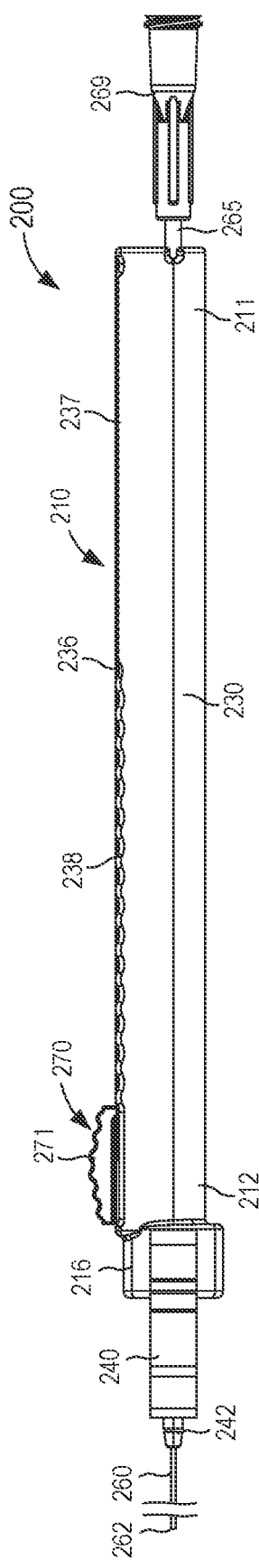
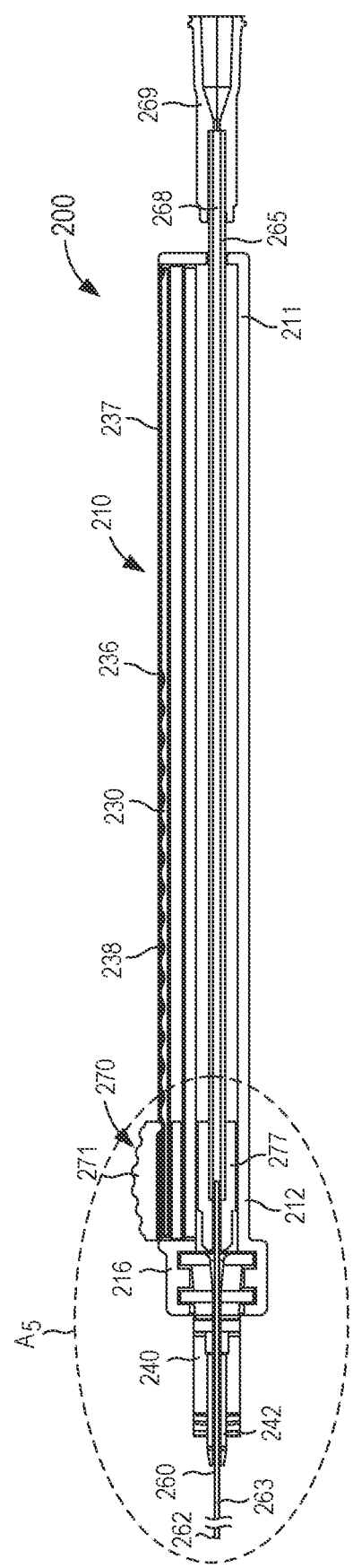
FIG. 27
FIG. 28

10

Couple, to an indwelling peripheral intravenous line, a lock of a fluid transfer device having an introducer coupled to the lock, a catheter movably disposed in the introducer, and an actuator coupled to the catheter and in contact with an outer surface of the introducer
11

Move the actuator relative to the introducer to advance the catheter from a first position, in which the catheter is disposed within at least one of an inner volume of the introducer or the lock, toward a second position
12

Provide, to a user, an indication associated with a position of a distal end portion of the catheter as the actuator moves the catheter from the first position toward the second position
13

Place the catheter in the second position based on the indication such that the distal end portion of the catheter is disposed beyond at least a portion of the peripheral intravenous line
14

FIG. 30

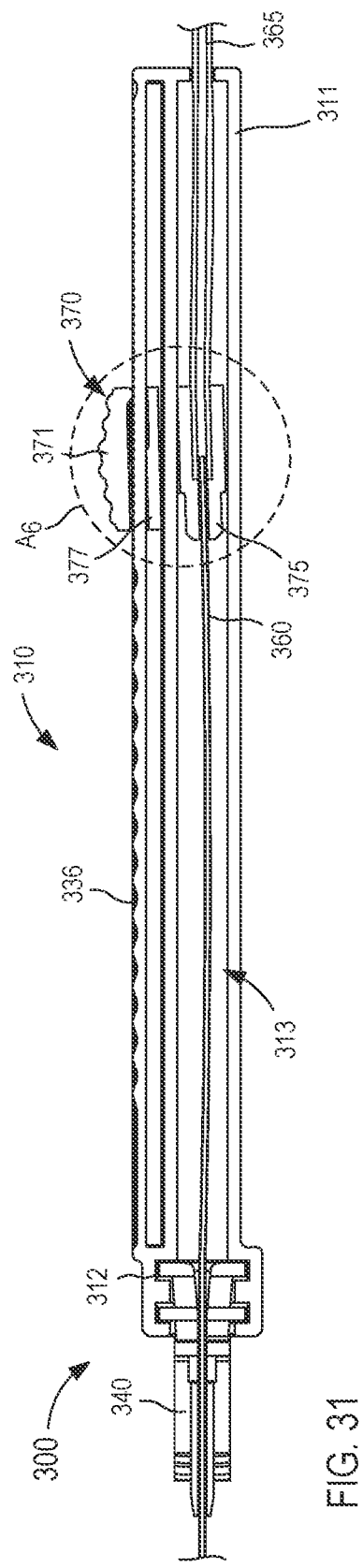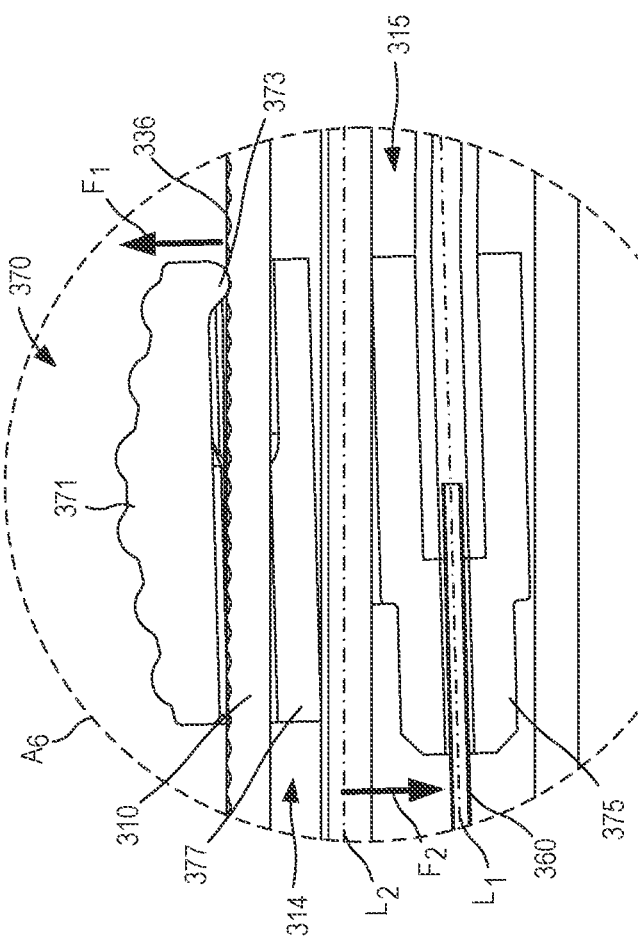
FIG. 31
FIG. 32

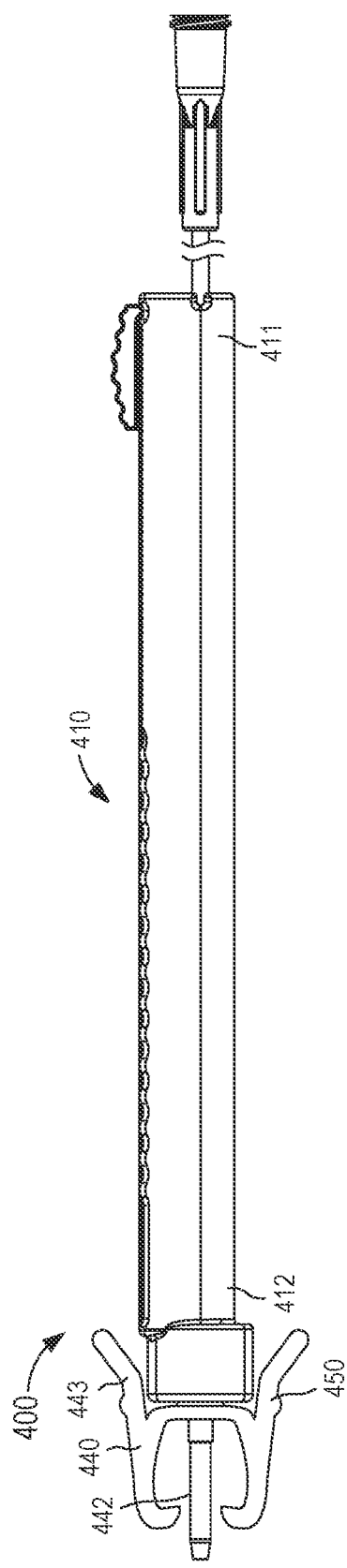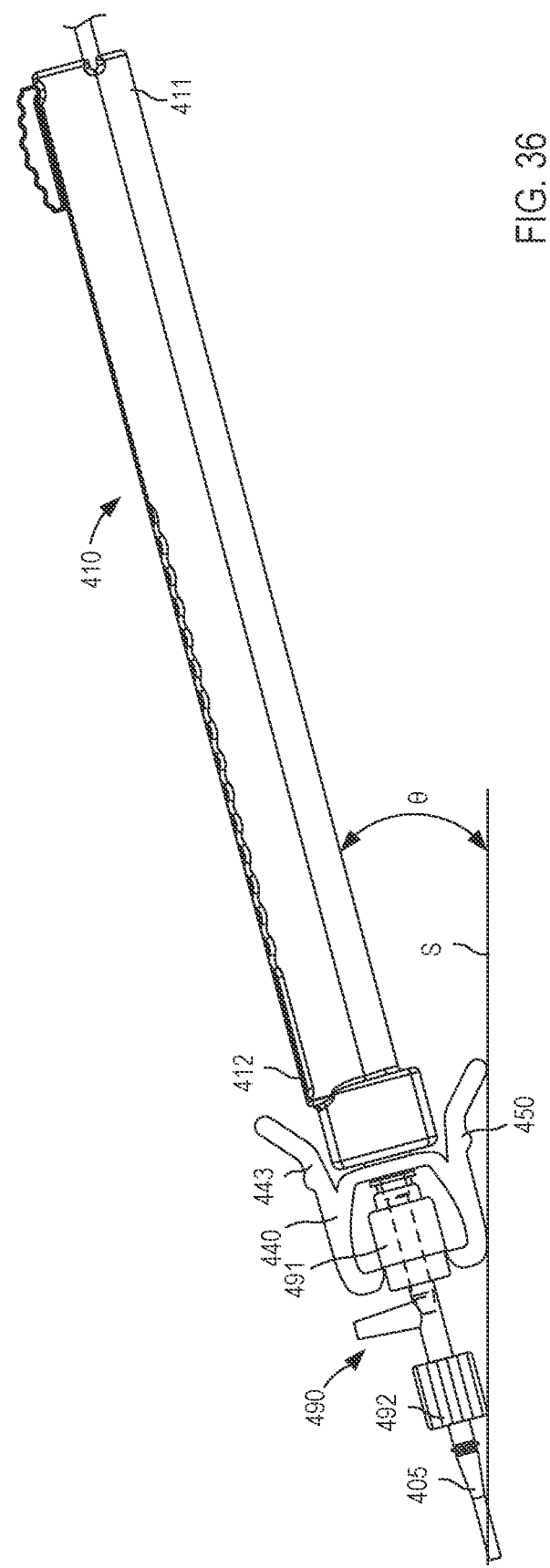

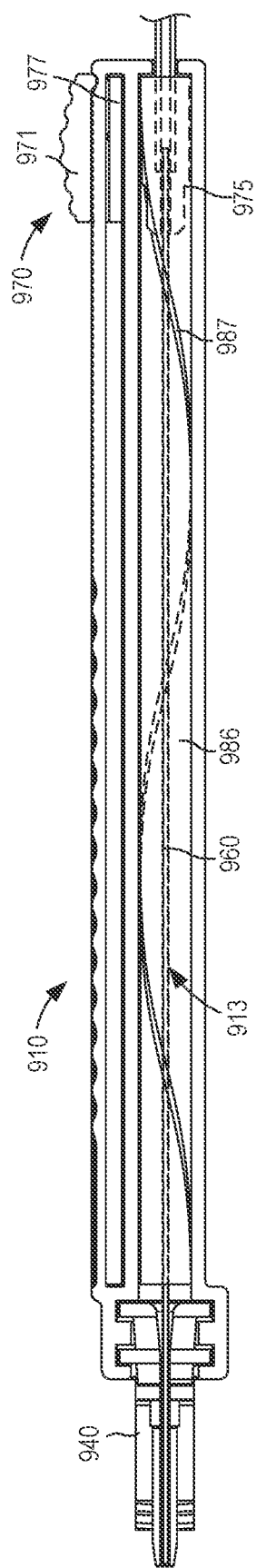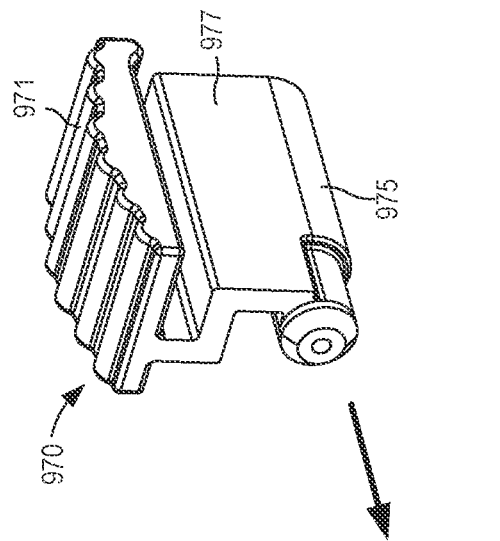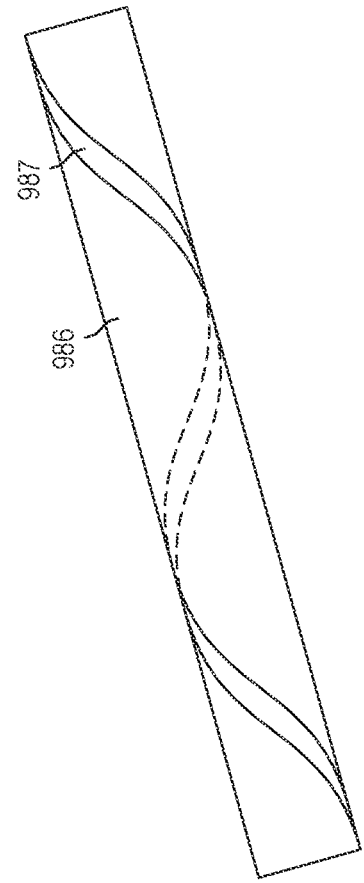
FIG. 42
FIG. 43

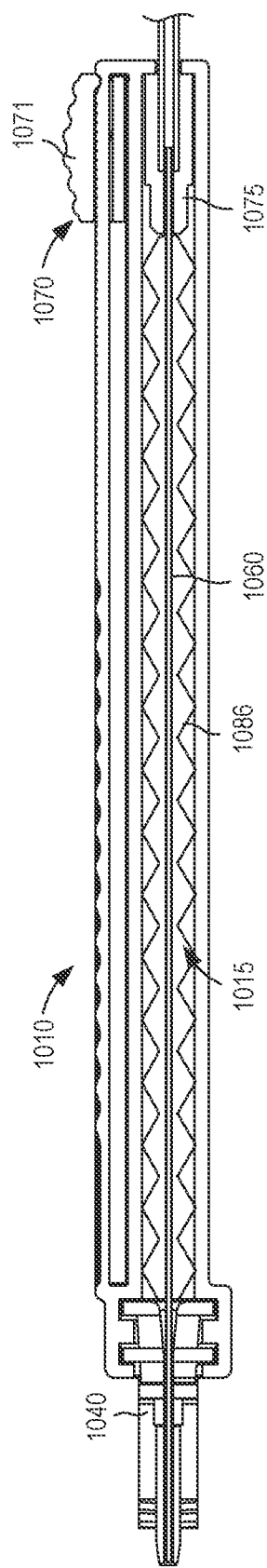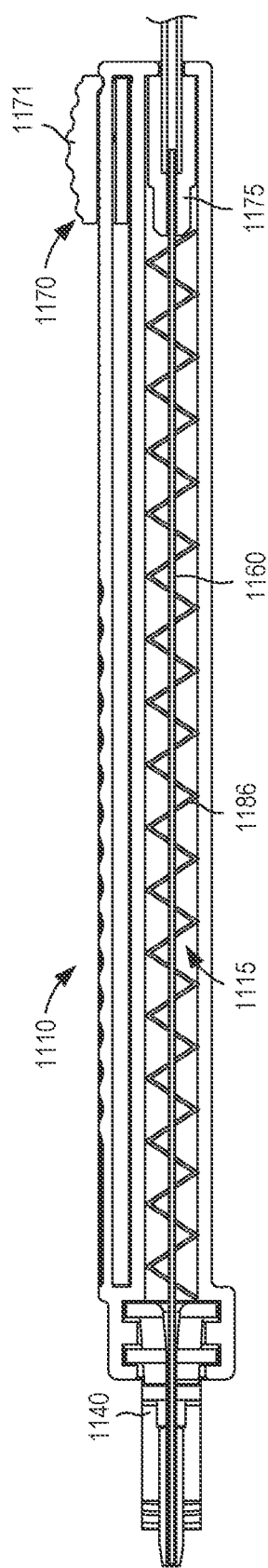

DEVICES AND METHODS FOR FLUID TRANSFER THROUGH A PLACED PERIPHERAL INTRAVENOUS CATHETER

CROSS-REFERENCE TO RELATED APPLICATIONS

This application is a divisional of U.S. patent application Ser. No. 15/927,509 entitled "Devices and Methods for Fluid Transfer Through a Placed Peripheral Intravenous Catheter", filed Mar. 21, 2018, which claims priority to and the benefit of U.S. Provisional Patent Application Ser. No. 62/474,202 entitled, "Devices and Methods for Fluid Transfer Through a Placed Peripheral Intravenous Catheter", filed Mar. 21, 2017, the disclosures of each of which are incorporated herein by reference in their entirety.

BACKGROUND

The embodiments described herein relate generally to fluid transfer medical devices. More particularly, the embodiments described herein relate to devices and methods for transferring fluid to or from a patient through a placed peripheral intravenous catheter.

The typical hospitalized patient encounters a needle every time a doctor orders a lab test. The standard procedure for blood extraction involves using a metal needle ("butterfly needle") to "stick" patients' veins in their arms or hands. Blood drawing is a manual, labor intensive process, with the average patient requiring hours of direct skilled labor during a typical hospital stay. This needle stick is not only painful and a major source of patient dissatisfaction, but the nurses or specialized blood drawing personnel (phlebotomists) often have difficulty finding the vein in approximately 10-15% of patients, resulting in multiple, painful "stick" attempts. This results in significantly higher material and labor costs (needles and tubing must be disposed of after every attempt) and increased patient pain and bruising.

The current process for drawing blood is inefficient, taking on average 7-10 minutes, and more than 21 minutes for 10% of patients. These 10% of patients are referred to as Difficult Intra-Venous Access or more commonly as "tough stick" patients. If superficial veins are not readily apparent, blood can be forced into the vein by massaging the arm from wrist to elbow, tapping the site with the index and middle finger, applying a warm, damp washcloth to the site for 5 minutes, or by lowering the extremity over the bedside to allow the veins to fill. Each of these methods is time consuming and therefore costly.

Peripheral IV catheters (PIVs) are inserted into most patients while they are hospitalized and used for infusing fluids and medications. However, they are not designed for blood extractions. The failure rates for aspiration reach 20-50% when PIV s have been left inserted for more than a day. Blood extracted from PIVs is often hemolyzed, defined as the rupture of red blood cells and the release of their contents into surrounding fluid, resulting in a discarded sample and need to repeat the blood collection.

Several barriers can contribute to the shortcomings of extracting blood through a PIV. First, most catheters are formed from a soft bio-reactive polymer, which can lead to a potential narrowing or collapse of the catheter as the negative pressure is applied for aspiration. Another barrier is that longer indwelling times can increase debris (e.g., fibrin/platelet clots) that builds up on the tip of the catheter and within the lumen of the catheter and/or PIV. Similarly, such debris can at least partially occlude the lumen of the vein in which the PIV is placed. In some instances, this debris (e.g., fibrin/platelet clots) around the PIV can lead to reduced blood flow within portions of the vein surrounding the inserted PIV (e.g., both upstream and downstream), which in turn, results in improper and/or inefficient aspiration. Another barrier is attributed to a "suction cup" effect, wherein the negative pressure created by aspiration through the catheter and the possible curved path of a vein results in the tip of the catheter adhering to the wall of the vein. As the negative pressure increases the vein can rupture resulting in "blowing the vein." which is a concern for phlebotomists during aspiration through a PIV.

Thus, a need exists for an improved system and method for phlebotomy through a peripheral intravenous catheter.

SUMMARY

Devices and methods for transferring fluid to or from a patient through a placed peripheral intravenous catheter are described herein. In some embodiments, an apparatus includes a catheter, an introducer, and an actuator. The catheter has a proximal end portion and a distal end portion and defines a lumen therethrough. The introducer has a proximal end portion and a distal end portion and defines an inner volume configured to movably receive the catheter. The distal end portion of the introducer has a lock configured to couple the introducer to an indwelling peripheral intravenous line. The actuator is movably coupled to the introducer and has a first portion disposed outside of the introducer and a second portion disposed in the inner volume of the introducer and coupled to the proximal end portion of the catheter. The actuator is configured to be moved relative to the introducer to move the catheter between a first position, in which the catheter is disposed within the introducer, and a second position, in which the distal end portion of the catheter is disposed beyond the distal end portion of the introducer such that at least a first portion of the catheter is disposed within the peripheral intravenous line when the introducer is coupled to the peripheral intravenous line. The first portion of the actuator is in contact with an outer surface of the introducer such that (1) a longitudinal axis defined by the second portion of the actuator is nonparallel to a longitudinal axis defined by the introducer and (2) the second portion of the actuator exerts a force on the proximal end portion of the catheter operable to increase an internal stress within at least second a portion of the catheter.

BRIEF DESCRIPTION OF THE DRAWINGS

FIG. 8 is a side view of the second member illustrated in FIG. 7.

FIG. 9 is an enlarged view of a portion of the second member identified in FIG. 8 by the region A1.

FIG. 11 is a front perspective view of the introducer illustrated in FIG. 10.

FIG. 12 is a cross-sectional view of the introducer taken along the line 12-12 in FIG. 11.

FIG. 27 is a side view of the fluid transfer device of FIG. 3 in the second configuration.

FIG. 28 is a cross-sectional view of the fluid transfer device in the second configuration taken along the line 22-22 in FIG. 3.

FIG. 30 is a flowchart illustrating a method of using a fluid transfer device according to an embodiment.

FIG. 31 is a cross-sectional side view of a fluid transfer device according to an embodiment.

FIG. 32 is an enlarged cross-sectional view side of a portion of the fluid transfer device illustrated in FIG. 31 by the region A6.

FIG. 35 is a side view of a fluid transfer device according to an embodiment.

FIG. 36 is a side view of the fluid transfer device of FIG. 35 disposed at a predetermined angle relative to a target surface.

FIG. 42 is a cross-sectional side view of a fluid transfer device and an internal support member according to an embodiment.

FIG. 43 is a perspective view of the internal support member and an actuator of the fluid transfer device illustrated in FIG. 42.

FIGS. 44 and 45 are cross-sectional side views of a fluid transfer device and an internal support member each according to a different embodiment.

DETAILED DESCRIPTION

Figure 1:
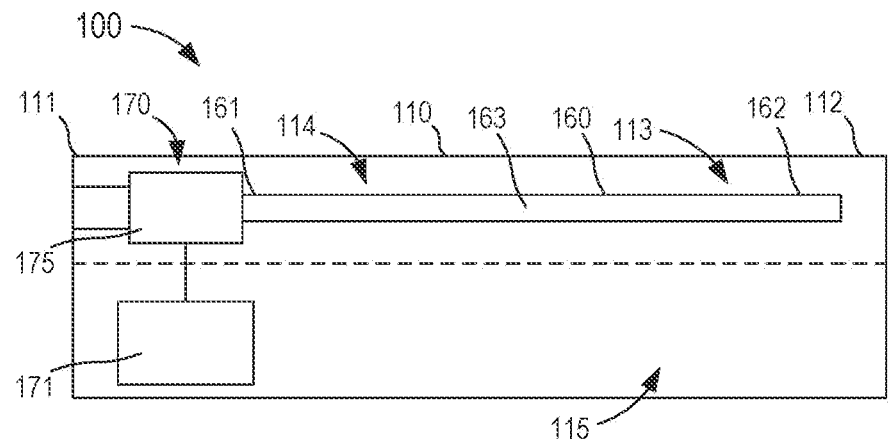
FIGS. 1 and 2 are schematic illustrations of a fluid transfer device in a first configuration and a second configuration, respectively, according to an embodiment.

In some embodiments, an apparatus includes a catheter, an introducer, and an actuator. The catheter has a proximal end portion and a distal end portion and defines a lumen therethrough. The introducer has a proximal end portion and a distal end portion and defines an inner volume configured to movably receive the catheter. The distal end portion of the introducer has a lock configured to couple the introducer to an indwelling peripheral intravenous line. The actuator is movably coupled to the introducer and has a first portion disposed outside of the introducer and a second portion disposed in the inner volume of the introducer and coupled to the proximal end portion of the catheter. The actuator is configured to be moved relative to the introducer to move the catheter between a first position, in which the catheter is disposed within the introducer, and a second position, in which the distal end portion of the catheter is disposed beyond the distal end portion of the introducer such that at least a first portion of the catheter is disposed within the peripheral intravenous line when the introducer is coupled to the peripheral intravenous line. The first portion of the actuator is in contact with an outer surface of the introducer such that (1) a longitudinal axis defined by the second portion of the actuator is nonparallel to a longitudinal axis defined by the introducer and (2) the second portion of the actuator exerts a force on the proximal end portion of the catheter operable to increase an internal stress within at least second a portion of the catheter.

In some embodiments, an apparatus includes a catheter, an introducer, and an actuator. The catheter has a proximal end portion and a distal end portion and defines a lumen therethrough. The introducer has a proximal end portion and a distal end portion and defines an inner volume configured to movably receive the catheter. The distal end portion of the introducer has a lock configured to couple the introducer to an indwelling peripheral intravenous line. The lock defines a lumen configured to movably receive the catheter. The actuator is coupled to the proximal end portion of the catheter and is configured to move relative to the introducer in response to a first force exerted on the actuator to move the catheter between a first position, in which the distal end portion of the catheter is disposed within the lumen of the lock, and a second position, in which the catheter extends through the lock and the peripheral intravenous line when the lock is coupled to the peripheral intravenous line such that the distal end portion of the catheter is distal to the peripheral intravenous line. The actuator is configured to exert a second force different from the first force on the proximal end portion of the catheter as the actuator moves the catheter from the first position to the second position. The second force results in a deflection of a portion of the catheter disposed between the actuator and the lock as the actuator moves the catheter from the first position to the second position.

In some embodiments, a method of using a fluid transfer device includes coupling a lock of the fluid transfer device to an indwelling peripheral intravenous line. The fluid transfer device includes an introducer having a distal end portion coupled to the lock, a catheter movably disposed in an inner volume defined by the introducer, and an actuator coupled to a proximal end portion of the catheter and configured to be moved relative to the introducer. A first force is exerted on the actuator to move the actuator relative to the introducer to advance the catheter from a first position, in which a distal end portion of the catheter is disposed within a lumen defined by the lock, toward a second position. A second force different from the first force is exerted by the actuator on the proximal end portion of the catheter as the actuator advances the catheter from the first position toward the second position. A portion of the catheter disposed between the actuator and the lock is deflected a first amount in response to the second force as the catheter is advanced from the first position to the second position. The portion of the catheter is deflected a second amount greater than the first amount in response to (1) the second force and (2) the distal end portion of the catheter impacting an obstruction as the catheter is advanced from the first position to the second position.

In some embodiments, an apparatus includes a catheter, an introducer, and an actuator. The catheter has a proximal end portion and a distal end portion. The introducer has a proximal end portion and a distal end portion and is configured to be coupled to a peripheral intravenous line. The introducer defines an inner volume configured to movably receive the catheter. The actuator includes a first portion that is in contact with an outer surface of the introducer and a second portion disposed within the inner volume and coupled to the proximal end portion of the catheter. The actuator is configured to move relative to the introducer to move the catheter between a first position, in which the catheter is disposed within the introducer, and a second position, in which the distal end portion of the catheter is disposed beyond the distal end portion of the introducer such that at least a portion of the catheter is disposed within the peripheral intravenous line when the introducer is coupled thereto. The contact between the outer surface and the first portion of the actuator is such that the catheter is biased when the catheter is in the first position.

As used herein, the terms "catheter" and "cannula" are used interchangeably to describe an element configured to define a passageway for moving a bodily fluid from a first location to a second location (e.g., a fluid passageway to move a bodily fluid out of the body). While cannulas can be configured to receive a trocar, a guide wire, or an introducer to deliver the cannula to a volume inside the body of a patient, the cannulas referred to herein need not include or receive a trocar, guide wire, or introducer.

As used in this specification, the terms "Y-adapter" and "T-adapter" are used to refer to a dual port IV extension set. In this manner, the terms "Y-adapter" and "T-adapter" generally describe an overall shape of the dual port IV extension set. For example, as used herein, a Y-adapter is substantially "Y" shaped including a single port at a first end and two ports angularly disposed at a second end. Furthermore, the terms "Y-adapter" and "T-adapter" are included by way of example only and not limitation. For example, in some embodiments, an apparatus can include a single port IV extension set (e.g., a single port adapter) or a multi-port IV extension set (e.g., an adapter with more than two ports).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the term "stiffness" relates to an object's resistance to deflection, deformation, and/or displacement by an applied force. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness is an extensive property of the object being described, and thus is dependent upon the material from which the object is formed as well as certain physical characteristics of the object (e.g., shape and boundary conditions). For example, the stiffness of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be increased, for example, by introducing into the object and/or constructing the object of a material having a high modulus of elasticity.

Similarly, a material's hardness is an intensive property of the constituent material and describes the measure of how resistant the material is to various kinds of permanent shape change when a force is applied. In discussing the hardness and the subsequent effect on the stiffness of a catheter, the Shore durometer scale is generally used. There are several scales for durometers with two commonly used in describing plastics, polymers, elastomers, and/or rubbers, namely, type A and type D, where type A is generally used for softer materials and type D is generally used for harder materials. The Shore durometer of a material is denoted by a number between 0 and 100, with higher numbers indicating a harder material, followed by the type of scale. For instance, a first material can be measured as having a Shore durometer of 40 Shore A and a second material can be measured as having a Shore durometer of 20 Shore D. Therefore, according to the Shore durometer scale, the second material is harder and thus, more stiff than the first material.

As used herein, the word "clutch" and/or "clutching" refers to a transitioning of a catheter between a first configuration (e.g., an "unclutched" configuration) and a second configuration (e.g., a "clutched" configuration) in a predetermined and/or predictable manner. Specifically, a catheter can bent, flexed, bowed, deformed, deflected, moved, compressed, and/or otherwise reconfigured when transitioned from an "unclutched" configuration to a "clutched" configuration. In some instances, a catheter can "clutch" and/or can be "clutched" in response to a distal end of the catheter impacting an obstruction, kink, bend, valve, etc. that restricts, limits, and/or substantially prevents further movement thereof. In some instances, the clutching of the catheter can be in the form of a linear, sinusoidal, elliptical, curvilinear, and/or logarithmic deflection and/or deformation, or any other form or combination of forms of deflection and/or deformation away from an original or "unclutched" configuration. In some instances, an amount and/or manner of deformation and/or deflection ("clutching") of the catheter when transitioned to the clutched configuration can be tuned by increasing or decreasing the stiffness, hardness, and/or durometer of the constituent material forming the catheter, increasing or decreasing an inner and/or outer diameter of the catheter, increasing or decreasing a wall thickness of the catheter, increasing or decreasing a length of a substantially unsupported portion of the catheter, increasing or decreasing a range of motion and/or degree of freedom of the catheter, increasing or decreasing an amount of force transferred to the catheter, and/or any other suitable adjustment.

Figure 2:
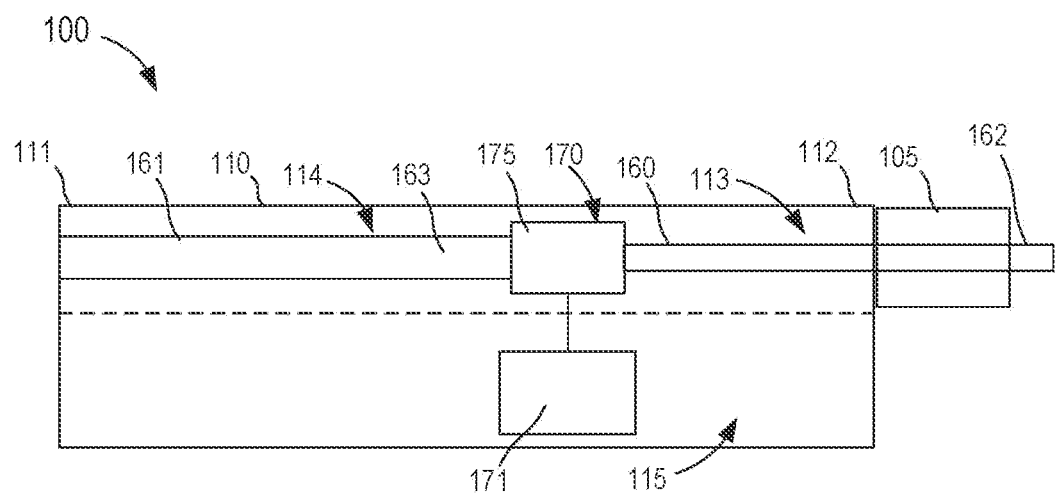

FIGS. 1 and 2 are schematic illustrations of a fluid transfer device 100 for phlebotomy through a peripheral intravenous line or catheter in a first configuration and second configuration, respectively, according to an embodiment. The fluid transfer device 100 (also referred to herein as "transfer device") can be any suitable shape, size, and/or configuration. As described in further detail herein, the transfer device 100 is configured to couple to and/or otherwise engage an indwelling peripheral intravenous catheter (PIV) 105 to transfer fluid from (e.g., aspiration of blood) and/or transfer fluid to (e.g., infusion of a drug or substance) a portion of a patient.

The transfer device 100 includes at least an introducer 110, a catheter 160 (or cannula), and an actuator 170. The introducer 110 can be any suitable configuration. For example, in some embodiments, the introducer 110 can be an elongate member having a substantially circular cross-sectional shape. In some embodiments, the shape of the introducer 110 and/or one or more features or surface finishes of at least an outer surface of the introducer 110 can be arranged to increase the ergonomics of the transfer device 100, which in some instances, can allow a user to manipulate the transfer device 100 with one hand (i.e., single-handed use).

The introducer 110 has a proximal end portion proximal end portion 111 and a distal end portion 112 and defines an inner volume 113. Although not shown in FIGS. 1 and 2, the proximal end portion 111 of the introducer 110 can include an opening or port configured to movably receive a portion of the catheter 160. As such, a first portion of the catheter 160 can be disposed within the inner volume 113 and a second portion of the catheter 160 can be disposed outside of the inner volume 113. The opening or port can be any suitable configuration. For example, in some embodiments, the opening and/or port can include a seal or the like configured to form a substantially fluid tight seal with an outer surface of the portion of the catheter 160 disposed therein. In other embodiments, the arrangement of the opening and/or port can be such that a user can place the catheter 160 in selective contact with a surface of the proximal end portion 111 defining the opening and/or port, which in turn, can clamp and/or pinch the catheter 160 to selectively obstruct a lumen of the catheter 160, as described in further detail herein with reference to specific embodiments.

The distal end portion 112 of the introducer 110 includes and/or is coupled to a lock configured to physically and fluidically couple the introducer 110 to the PIV 105 (see e.g., FIG. 2). For example, in some embodiments, the distal end portion 112 can include a coupler or the like such as a Luer Lok™ configured to physically and fluidically couple to an associated coupler of the lock. In some embodiments, the lock is configured to selectively engage and/or contact the PIV 105 to couple the introducer 110 thereto. For example, in some embodiments, the shape, size, and/or arrangement of the lock is such that the lock forms three points of contact with the PIV 105. In some embodiments, such an arrangement can provide structural rigidity and/or support to the PIV 105 as a portion of the lock (e.g., a proboscis or the like) is inserted into a portion of the PIV 105, as described in further detail herein.

In some embodiments, the distal end portion 112 of the introducer 110 can include and/or can be coupled to a support member or the like that is operable in placing the introducer 110 and/or device 100 at a predetermined angle relative to a target surface. For example, in some embodiments, the arrangement of the lock can be such that placing a predetermined portion of the lock in contact with a target surface, in turn, places the introducer 110 and/or device 100 at a predetermined and/or desired angle relative to the target surface. In other embodiments, a support member and/or the like can be coupled to the distal end portion 112 of the introducer 110 and configured to place the introducer 110 and/or device 100 at the predetermined and/or desired angle relative to the target surface. In some instances, the target surface can be a cutaneous surface of a body through which the PIV 105 is inserted (e.g., an outer surface of a patient's arm or the like). In some embodiments, the predetermined angle can be, for example, between about 0° and about 30°, between about 4° and about 15°, between about 8° and about 10°, or any other suitable angle.

In some embodiments, the distal end portion 112 of the introducer 110 (and/or the lock) can include a seal or the like that can be transferred from a sealed configuration to a substantially open configuration to place at least a portion of the inner volume 113 in fluid communication with the lock. In some embodiments, the seal can include back flow prevention mechanism such as a one-way valve or the like that can allow, for example, the catheter 160 to be advanced in the distal direction therethrough while limiting and/or substantially preventing a fluid flow, outside the catheter 160, in the proximal direction through the seal.

As described above, the introducer 110 defines the inner volume 113, which extends between the proximal end portion 111 and the distal end portion 112. The inner volume 113 has and/or defines a first portion 114 configured to receive a first portion 171 of the actuator 170 and a second portion 115 configured to receive the catheter 160 and a second portion 175 of the actuator 172, as shown in FIGS. 1 and 2. More specifically, an inner surface of the introducer 110 that defines the inner volume 113 can have, for example, a tortuous cross-sectional shape (not shown in FIGS. 1 and 2) such that an axis defined by the first portion 114 of the inner volume 113 is parallel to and offset from an axis defined by the second portion 115 of the inner volume 113. In this manner, the first portion 114 of the inner volume 113 can be spaced apart from the second portion 115 of the inner volume 113 without being fluidically isolated therefrom. In some embodiments, the first portion 114 of the inner volume 113 can extend through a wall of the introducer 110. In other words, the introducer 110 can define a slot, channel, track, opening, and/or the like that is in fluid communication with the first portion 114 of the inner volume 113. Conversely, the second portion 115 of the inner volume 113 can be entirely defined and/or enclosed (at least in the circumferential direction) by the introducer 110. Moreover, in some embodiments, the tortuous cross-sectional shape of the inner volume 113 is such that the second portion 115 cannot be viewed (e.g., is out of the line of sight) via the slot or the like in fluid communication with the first portion 114 of the inner volume 113, which in turn, can limit and/or substantially prevent contamination of the catheter 160 disposed therein.

Although not shown in FIGS. 1 and 2, in some embodiments, the introducer 110 can include and/or can receive an internal support member or the like. In such embodiments, the internal support member can be positioned within the inner volume 113 and can be configured to support and/or guide at least a portion of the catheter 160 disposed in the inner volume 113 of the introducer 110. In some embodiments, the internal support member can be configured to at least partially isolate a portion of the catheter 160, which in turn, can be operative to maintain the sterility of the catheter 160 prior to use.

The catheter 160 of the transfer device 100 includes a proximal end portion 161 and a distal end portion 162 and defines a lumen 163 that extends through the proximal end portion 161 and the distal end portion 162. The catheter 160 is movably disposed within the second portion 115 of the inner volume 113 defined by the introducer 110 and is coupled to the actuator 170. In some embodiments, the catheter 160 can be moved (e.g., via movement of the actuator 170) between a first position and a second position to transition the transfer device 100 between the first configuration and the second configuration, respectively. More specifically, at least the distal end portion 162 of the catheter 160 is disposed within the second portion 115 of the inner volume 113 when the catheter 160 is in the first position (FIG. 1) and at least a portion of the catheter 160 extends through the PIV 105 to place a distal end of the catheter 160 in a distal position relative to a portion of the PIV 105 when the catheter 160 is in the second position (FIG. 2). Although not shown in FIGS. 1 and 2, in some embodiments, the transfer device 100 can include a secondary catheter or the like that is coupled to the actuator 170 and in fluid communication with the catheter 160. In such embodiments, the secondary catheter can be, for example, disposed in a proximal position relative to the catheter 160 and can be configured to extend through the opening and/or port defined by the proximal end portion 111 of the introducer 110. In this manner, a proximal end portion of the secondary catheter can be coupled to a vacuum (air or liquid) source, a fluid reservoir, fluid source, syringe, and/or the like, which in turn, places the catheter 160 in fluid communication therewith. Moreover, in embodiments including the secondary catheter, the catheter 160 can be entirely disposed within the introducer 110 when the catheter 160 is in the first position.

The catheter 160 can be any suitable shape, size, and/or configuration. For example, in some embodiments, at least a portion of the catheter 160 can have an outer diameter (e.g., between a 10-gauge and a 30-gauge) that is substantially similar to or slightly smaller than an inner diameter defined by a portion of the lock coupled to the distal end portion 112 of the introducer 110. In this manner, an inner surface of the portion of the lock can guide the catheter 160 as the catheter 160 is moved between the first position and the second position. In some embodiments, such an arrangement can limit and/or can substantially prevent bending, deforming, and/or kinking of a portion of the catheter 160 the portion is moved between the first position and the second position. In some embodiments, the catheter 160 can have a length that is sufficient to place a distal surface of the catheter 160 in a desired position relative to a distal surface of the PIV 105 when the catheter 160 is in the second position. In other words, the length of the catheter 160 can be sufficient to define a predetermined and/or desired distance between the distal surface of the catheter 160 and the distal surface of the PIV 105 when the catheter 160 is in the second position. In some instances, placing the distal surface of the catheter 160 at the predetermined and/or desired distance from the distal surface of the PIV 105 can, for example, place the distal surface of the catheter 160 in a desired position within a vein, as described in further detail herein.

The catheter 160 can be formed from any suitable material or combination of materials, which in turn, can result in the catheter 160 having any suitable stiffness or durometer. In some embodiments, at least a portion of the catheter 160 can be formed of a braided material or the like, which can change, modify, and/or alter a flexibility of the catheter 160 in response to a bending force or the like. In some embodiments, forming the catheter 160 of the braided material or the like can reduce a likelihood of kinking and/or otherwise deforming in an undesired manner. In addition, forming at least a portion of the catheter 160 of a braided material can result in a compression and/or deformation in response to a compression force exerted in a direction of a longitudinal centerline defined by the catheter 160 (e.g., an axial force or the like). In this manner, the catheter 160 can absorb a portion of force associated with, for example, impacting an obstruction or the like. As described in further detail herein, in some instances, at least a portion of the catheter 160 can deform in response to the force associated with impacting such an obstruction or the like.

The actuator 170 of the transfer device 100 can be any suitable shape, size, and/or configuration. As described above, the actuator 170 includes the first portion 171 movably disposed within the first portion 114 of the inner volume 113 and the second portion 175 movably disposed within the second portion 115 of the inner volume 113 and coupled to the catheter 160. Although not shown in FIGS. 1 and 2, the actuator 170 can have a cross-sectional shape that is associated with and/or otherwise corresponds to the cross-sectional shape of the inner volume 113 (e.g., the tortuous cross-sectional shape). Thus, an axis defined by the first portion 171 of the actuator 170 is parallel to and offset from an axis defined by the second portion 175 of the actuator 170.

The arrangement of the actuator 170 and the introducer 110 is such that the first portion 171 extends through the slot or the like in fluid communication with the first portion 114 of the inner volume 113. As such, a first region of the first portion 171 of the actuator 170 is disposed outside of the introducer 110 and a second region of the first portion 171 of the actuator 170 is disposed in the first portion 114 of the inner volume 113. In this manner, a user can engage the first region of the first portion 171 of the actuator 170 and can move the actuator 170 relative to the introducer 110 to move the catheter 160 coupled to the second portion 175 of the actuator 170 between the first position and the second position. Although not shown in FIGS. 1 and 2, in some embodiments, the first portion 171 of the actuator 170 can include a tab, protrusion, and/or surface that is in contact with an outer surface of the introducer 110. In such embodiments, the outer surface of the introducer 110 can include, for example, a set of ribs, ridges, bumps, grooves, and/or the like along which the tab, protrusion, and/or surface of the first portion 171 advances when the actuator 170 is moved relative to the introducer 110, which in turn, produces a haptic output or feedback (acoustic, tactile and visual) which can provide an indication associated with a position of the distal end portion 162 of the catheter 160 to the user.

In some embodiments, the arrangement of the first portion 171 of the actuator 170 and the outer surface of the introducer 110 is such that the actuator 1 70 is disposed at an angle relative to the introducer 110. That is to say, the contact between the first portion 171 of the actuator 170 and the outer surface of the introducer 110 tilts the actuator 170 relative to the introducer 110. Accordingly, in some instances, a longitudinal centerline of the actuator 170 can be nonparallel to a longitudinal centerline of the introducer 110. Furthermore, with the actuator 170 coupled to the proximal end portion 161 of the catheter 160, angling and/or tilting the actuator 170 results in a force (e.g., a pre-load force or the like) exerted on the catheter 160 that is sufficient to bend at least a portion of the catheter 160 (e.g., the catheter 160 is placed in a biased configuration), as described in further detail herein.

In some embodiments, the transfer device 100 can be disposed in the first configuration prior to use (e.g., shipped, stored, prepared, etc. in the first configuration). In use, a user can manipulate the transfer device 100 to couple the introducer 110 to the indwelling PIV 105 (e.g., via the lock coupled to and/or assembled with the introducer 110). With the transfer device 100 coupled to the PIV 105, the user can engage the first portion 171 of the actuator 170 to move the actuator 170 relative to the introducer 110, which in turn, moves the catheter 160 from the first position (e.g., disposed within the introducer 110) toward the second position. In some embodiments, the arrangement of the actuator 170 and the introducer 110 is such that advancing the actuator 170 relative to the introducer 110 produces a haptic output and/or feedback configured to provide and indicator associated with position of the distal end portion 162 of the catheter 160 relative to the introducer 110 and/or the PIV 105 to the user. For example, based on the haptic feedback or any other suitable indicator, the user can place the catheter 160 in the second position such that the distal surface of the catheter 160 extends a desired distance beyond the distal surface of the PIV 105, as described above.

With the catheter 160 in the second position (e.g., with the transfer device 100 in the second configuration shown in FIG. 2), the user can establish fluid communication between a fluid reservoir, fluid source, syringe, and/or the like and the catheter 160. For example, as described above, in some embodiments, the user can couple the secondary catheter (not shown) to the fluid reservoir, fluid source, syringe, and/or the like. Although described as establishing fluid communication between the catheter 160 and the fluid reservoir or fluid source after placing the catheter 160 in the second position, in other embodiments, the user can establish fluid communication between the catheter 160 and the fluid reservoir or fluid source prior to moving the actuator 170 relative to the introducer 110. With the catheter 160 in fluid communication with the fluid reservoir and/or fluid source, the transfer device 100 can then transfer a fluid from the patient or transfer a fluid to the patient via the catheter 160 extending through and beyond the PIV 105.

In some instances, the catheter 160 can impact an obstruction or the like as the user advances the catheter 160 (via the actuator 170) from the first position to the second position. In some such instances, the catheter 160 can be configured to bend, deform, and/or otherwise reconfigure in response to a force exerted by the user. That is to say, a force (e.g., an activation or actuation force) exerted by the user on the actuator 170 that otherwise is sufficient to move the catheter 160 toward the second position results in a deflection, deformation, and/or reconfiguration of at least a portion of the catheter 160 when the catheter 160 impacts an obstruction or the like. Moreover, with at least a portion of the catheter 160 being pre-loaded (e.g., bent, bowed, biased, deflected, and/or deformed in response to the angle of the actuator 170, as described above), the deflection, deformation, and/or reconfiguration of the portion of the catheter 160 can be predetermined, anticipated, and/or the like.

As described above, the deflection, deformation, and/or reconfiguration of the portion of the catheter 160 in response to impacting the obstruction can result in a "clutching" (e.g., bowing, bending, flexing, deflecting, deforming, compressing, etc.) of the catheter 160 and/or device 100 that reduces undesired forces otherwise exerted on, for example, a wall of a vein or the like. In some embodiments, the clutching of the catheter 160 can produce and/or can result in an audible, visual, and/or haptic indication that the catheter 160 has impacted an obstruction, as described in further detail herein with respect to specific embodiments. In some instances, once the catheter 160 and/or device 100 is "clutched" the user can pause as the preloaded and/or clutched catheter 160 and/or device 100 exerts a constant but linearly reducing force to overcome the obstruction or the like. In some instances, the clutched catheter 160 and/or device 100 can auto-unclutch (e.g., self-relieve at least a portion of the stress along a length of the catheter 160), resulting in a safe and/or controlled process for overcoming the obstruction.

FIGS. 3-29 illustrate a fluid transfer device 200 according to another embodiment. The fluid transfer device 200 (also referred to herein as "transfer device") can be any suitable shape, size, or configuration and can be coupled to a PIV (not shown in FIGS. 3-29), for example, via a lock and/or adapter. As described in further detail herein, a user can transition the transfer device 200 from a first configuration to a second configuration to advance a catheter through an existing, placed, and/or indwelling PIV (i.e., when the transfer device 200 is coupled thereto) such that at least an end portion of the catheter is disposed in a distal position relative to the PIV. Moreover, with peripheral intravenous lines each having a shape, size, and/or configuration that can vary based on, for example, a manufacturer of the PIV and/or its intended usage, the transfer device 200 can be arranged to allow the transfer device 200 to be coupled to a PIV having any suitable configuration and subsequently, to advance at least a portion of a catheter through the PIV substantially without kinking, snagging, breaking, and/or otherwise reconfiguring the catheter in an undesirable manner. In addition, the transfer device 200 can be manipulated by a user to place a distal surface of the catheter a predetermined and/or desired distance beyond a distal surface of the PIV to be disposed within a portion of a vein that receives a substantially unobstructed flow of blood.

Figure 3:
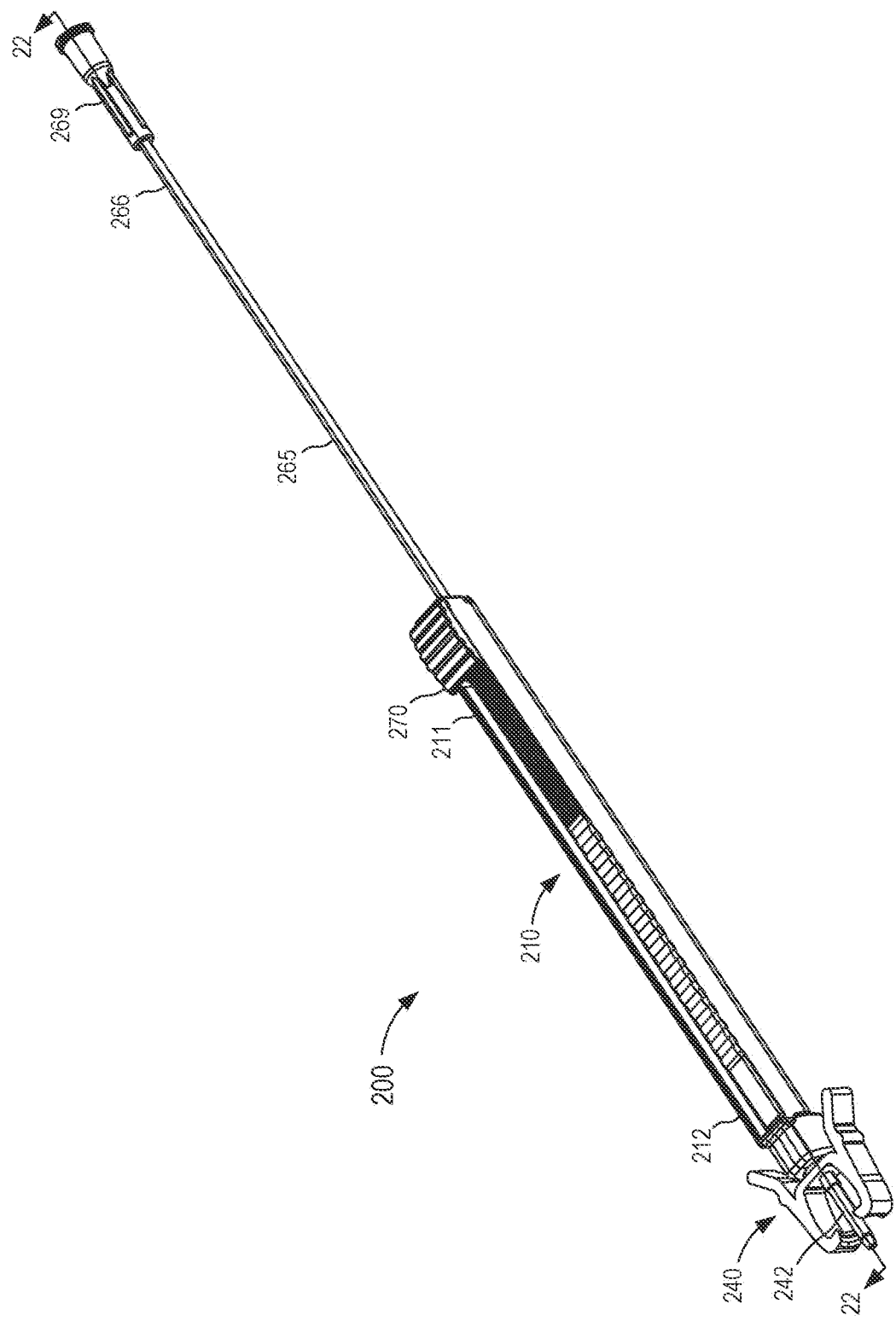
FIG. 3 is a perspective view of a fluid transfer device in a first configuration, according to an embodiment.
Figure 4:
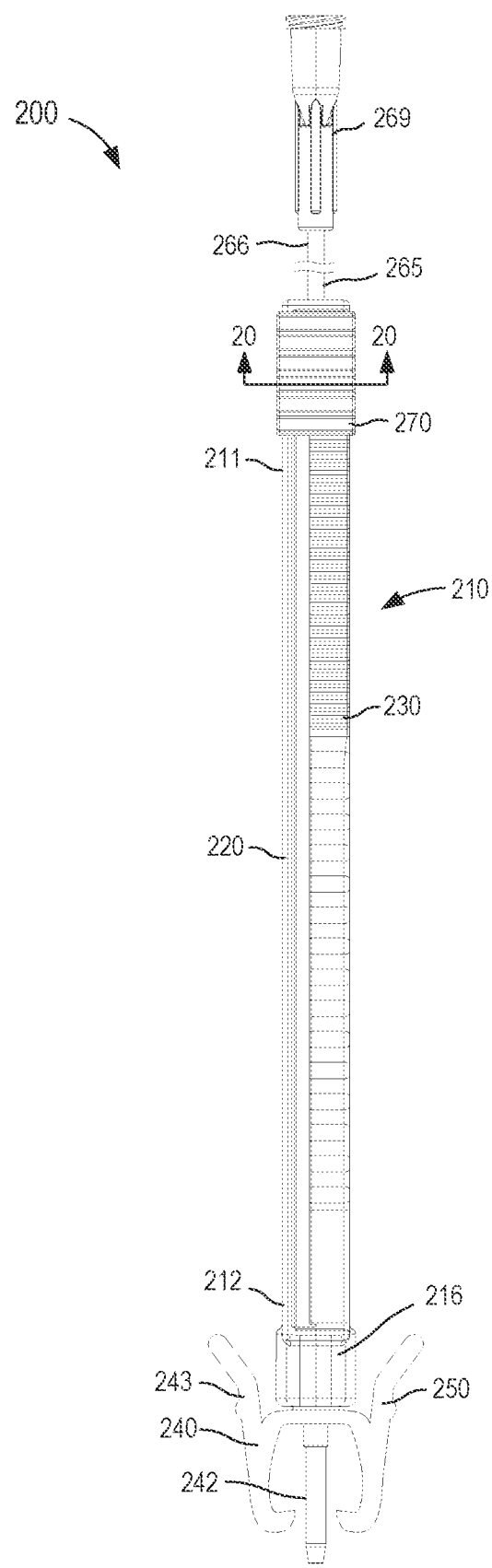
FIG. 4 is a top view of the fluid transfer device illustrated in FIG. 3.
Figure 5:
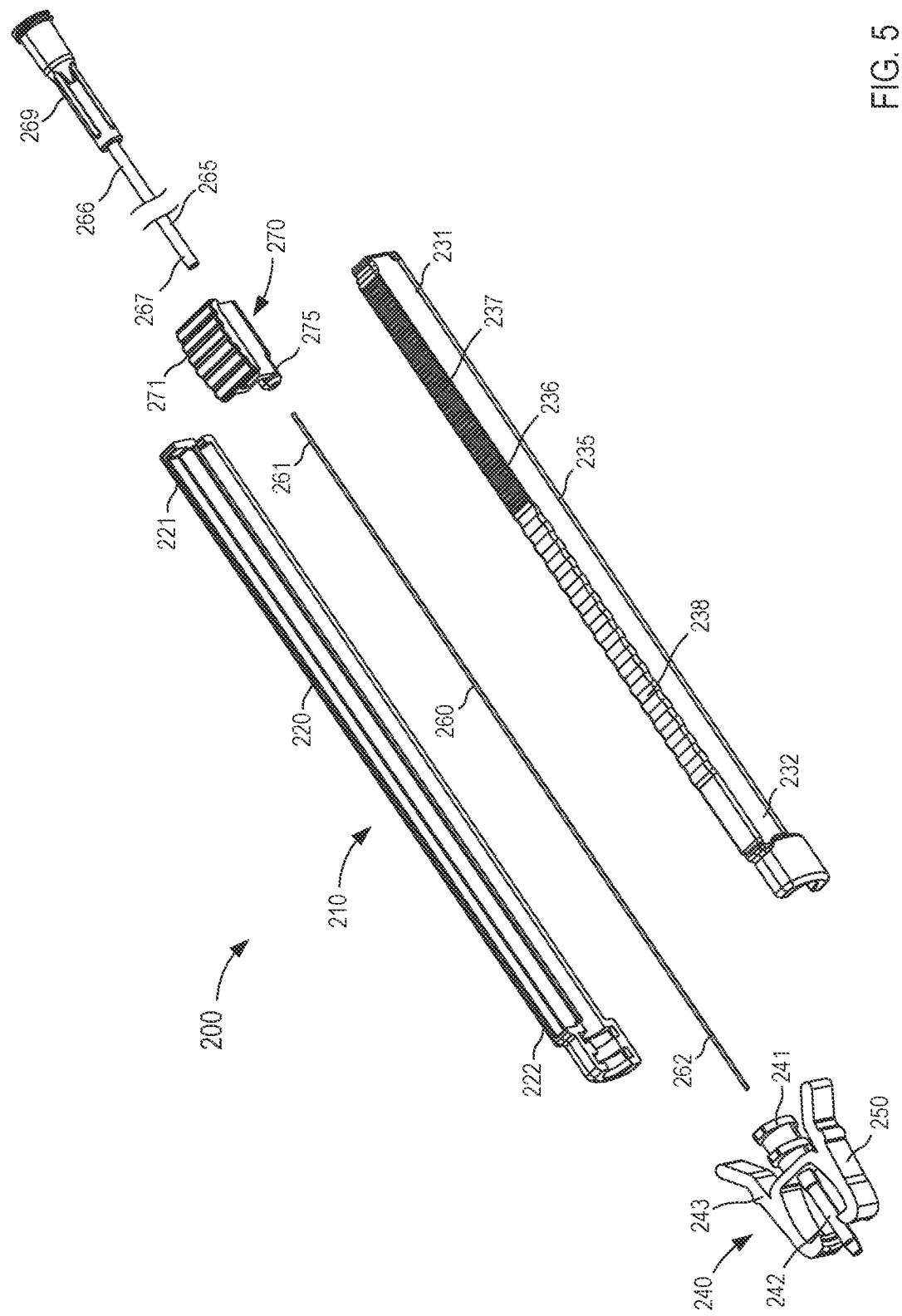
FIG. 5 is an exploded view of the fluid transfer device illustrated in FIG. 3.

As shown in FIGS. 3-5, the transfer device 200 includes an introducer 210, a lock 240, a catheter 260, a secondary catheter 265, and an actuator 270. The introducer 210 can be any suitable shape, size, or configuration. For example, in some embodiments, the introducer 210 can be an elongate member having a substantially circular cross-sectional shape. In some embodiments, the shape of the introducer 210 and/or one or more features or surface finishes of at least an outer surface of the introducer 210 can be arranged to increase the ergonomics of the transfer device 200, which in some instances, can allow a user to manipulate the transfer device 200 with one hand (i.e., single-handed use).

Figure 6:
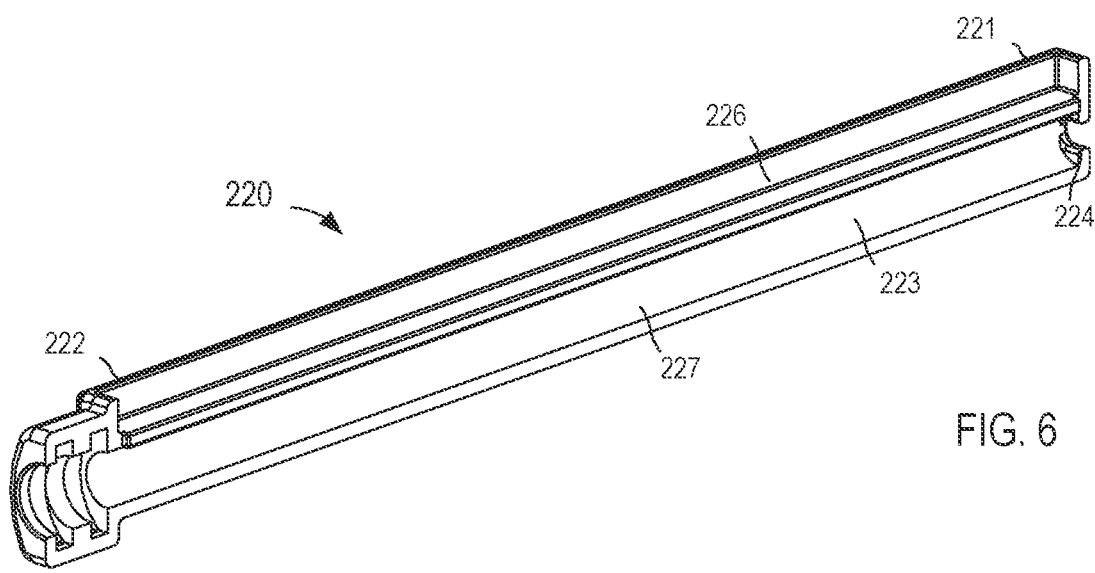
FIG. 6 is a perspective view of a first member of an introducer included in the fluid transfer device of FIG. 3.

As shown in FIGS. 5-12, the introducer 210 of the transfer device 200 includes a first member 220 and a second member 225 that are coupled to collectively form the introducer 210. As shown in FIG. 6, the first member 220 includes a proximal end portion 221, a distal end portion 222, and an inner surface 224. The inner surface 224 has a first portion 224 and a second portion 225. The proximal end portion 221 of the first member 220, and more specifically, a proximal wall of the first member 220 defines a notch 226 configured to selectively receive a portion of the secondary catheter 265, as described in further detail herein.

Figure 7:
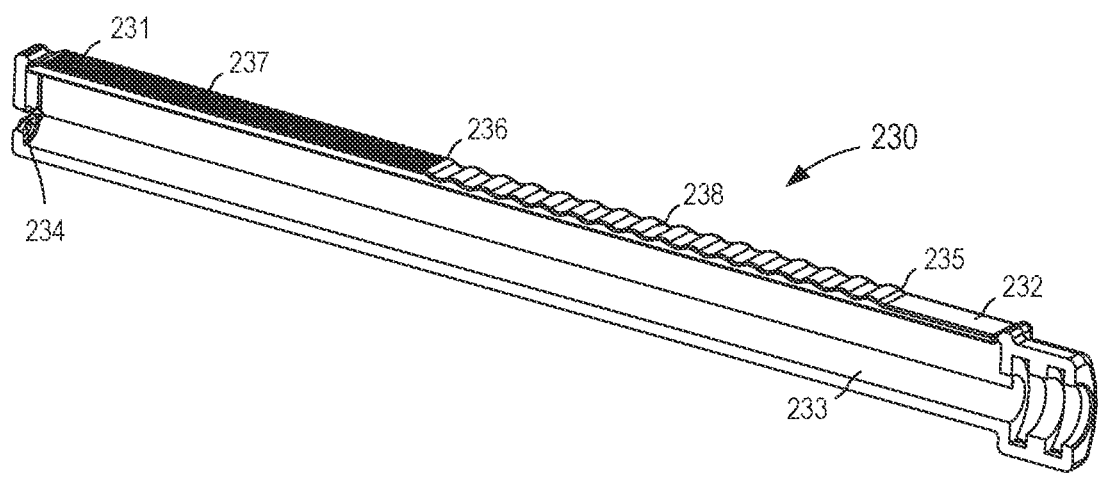
FIG. 7 is a perspective view of a second member of the introducer included in the fluid transfer device of FIG. 3.

As shown in FIGS. 7-9, the second member 230 has a proximal end portion 231, a distal end portion 232, an inner surface 233, and an outer surface 235. As described above with reference to the first member 220, the proximal end portion 231 of the second member 230, and more specifically, a proximal wall of the second member 230 defines a notch 234 configured to selectively receive a portion of the secondary catheter 265. The outer surface 235 of the second member 230 includes a set of ribs 236 distributed along a length of the second member 230. More particularly, each rib 236 extends along a width of the second member 230 and successively distributed along the length of the second member 230. In this manner, the outer surface 235 defines alternating local minima and local maxima arranged along the length of the second member 230. As described in further detail herein, a portion of the actuator 270 is configured to be advanced along the outer surface 235 forming the set of ribs 236 as a user moves the actuator 270 relative to the introducer 210, which in turn, vibrates the actuator 270 (and the catheter 260 coupled thereto). In some instances, this vibration can, for example, facilitate the advancing of the catheter 260 through a portion or the transfer device 200, a portion of the PIV, and/or a portion of the vasculature. Moreover, in some instances, the vibration can provide a user with a haptic and/or audible indicator associated with a position of the catheter 260 relative to the introducer 210 and/or PIV, as described in further detail herein.

The ribs 236 formed by the outer surface 235 of the second member 230 can be any suitable shape, size, and/or configuration. For example, as shown in FIGS. 8 and 9, the set of ribs 236 includes a first portion 237 having a first size and shape, and a second portion 238 having a second size and shape, different from the first size and shape. The first portion 237 of ribs 236 can have any suitable configuration and/or arrangement. For example, in this embodiment, each rib in the first portion 237 is substantially uniform having substantially the same size and shape. In other embodiments, each rib included in the first portion 237 can have a size and shape that is different from the remaining ribs of the first portion 237. For example, in some embodiments, the size and shape of each rib in the first portion 237 can increase from a proximal most rib having the smallest size and shape to a distal most rib having the largest size and shape. Moreover, while the ribs of the first portion 237 are shown as being substantially symmetrical, in other embodiments, each rib of the first portion 237 can be asymmetrical. For example, in some embodiments, a proximal surface of each rib can have a first pitch (e.g., angle) and a distal surface of each rib can have a second pitch that is greater than the first pitch. In some embodiments, such an asymmetric arrangement can be such that the portion of the actuator 270 moves along the outer surface 235 with a first set of characteristics when moved in a distal direction and moves along the outer surface 235 with a second set of characteristics, different from the first set of characteristics, when moved in a proximal direction. For example, in some embodiments, the portion of the actuator 270 can move along the outer surface 235 in the distal direction more freely than in the proximal direction.

Similarly, the second portion 238 of the ribs 236 can have any suitable configuration and/or arrangement. For example, in this embodiment, each rib in the second portion 238 is substantially uniform having substantially the same size and shape as the remaining ribs in the second portion 238. As shown in FIG. 9, each rib in the second portion 238 has a size and shape that is greater than the size and shape of each rib of the first portion 237. In some instances, the greater size of the ribs of the second portion 238 can result in a larger amount of vibration as the actuator 270 is moved along the outer surface 235 (as described above). In some instances, the greater size of the ribs of the second portion 238 can result in an increase in a force otherwise sufficient to move the portion of the actuator 270 along the outer surface 235. While the ribs of the second portion 238 are shown and described as being substantially uniform and having a larger size than the ribs of the first portion 237, in other embodiments, the ribs of the second portion 238 can have any of the arrangements and/or configurations described above with reference to the ribs of the first portion 237.

While the set of ribs 236 transitions from the first portion 237 to the second portion 238 at a given point along the length of the second member 230 (see e.g., FIG. 9), in other embodiments, the size and shape of each rib in the set of ribs 236 can increase from a proximal most rib of the first portion 237 having the smallest size and shape to a distal most rib of the second portion 238 having the largest size and shape. In other words, in some embodiments, the size and shape of each of rib in the set of ribs 236 can increase with each successive rib (e.g., in the distal direction). In still other embodiments, the set of ribs 236 can include more than the first portion 237 and the second portion 238. For example, in some embodiments, a second member can include a set of ribs having a first portion and a second portion having a size, shape, and configuration similar to the first portion 237 of the second member 230, and a third portion, disposed between the first portion and the second portion, having a size, shape, and configuration similar to the second portion 238 of the second member 230. That is to say, in such embodiments, the second member includes a proximal portion of ribs and a distal end portion of ribs that are smaller than a medial portion of ribs disposed therebetween. In some embodiments, the arrangement of the set of ribs 236 of the second member 230 can be such that a proximal most rib and a distal most rib are larger and/or otherwise have a shape that operable to at least temporarily maintain the portion of the actuator 270 in a proximal position relative to the proximal most rib and a distal position relative to the distal most rib, respectively.

While the set of ribs 236 are shown as being formed only by the outer surface 235 of the second member 230, in other embodiments, the first member 220 can include an outer surface that forms a set of ribs. In such embodiments, the set of ribs of the first member 220 can be and/or can have any of the configurations and/or arrangements described above with reference to the set of ribs 236 of the second member 230. In some embodiments, the ribs of the first member 220 can be offset from the ribs 236 of the second member 230. For example, in some embodiments, the ribs of the first member 220 can have alternating local minima and local maxima (as described above with reference to the ribs 236) that are distributed along a length of the first member 220 such that the local minima and local maxima of the ribs of the first member 220 are aligned with the local maxima and local minima, respectively, of the ribs 236 of the second member 230 (e.g., offset along a length of the introducer 210). In other embodiments, the ribs of the first member 220 can be in varying positions relative to the ribs 236 of the second member 230. In this manner, the introducer 210 can provide a variable arrangement of ribs that can provide, for example, haptic feedback as the actuator 270 is moved relative to the introducer 210.

Figure 10:
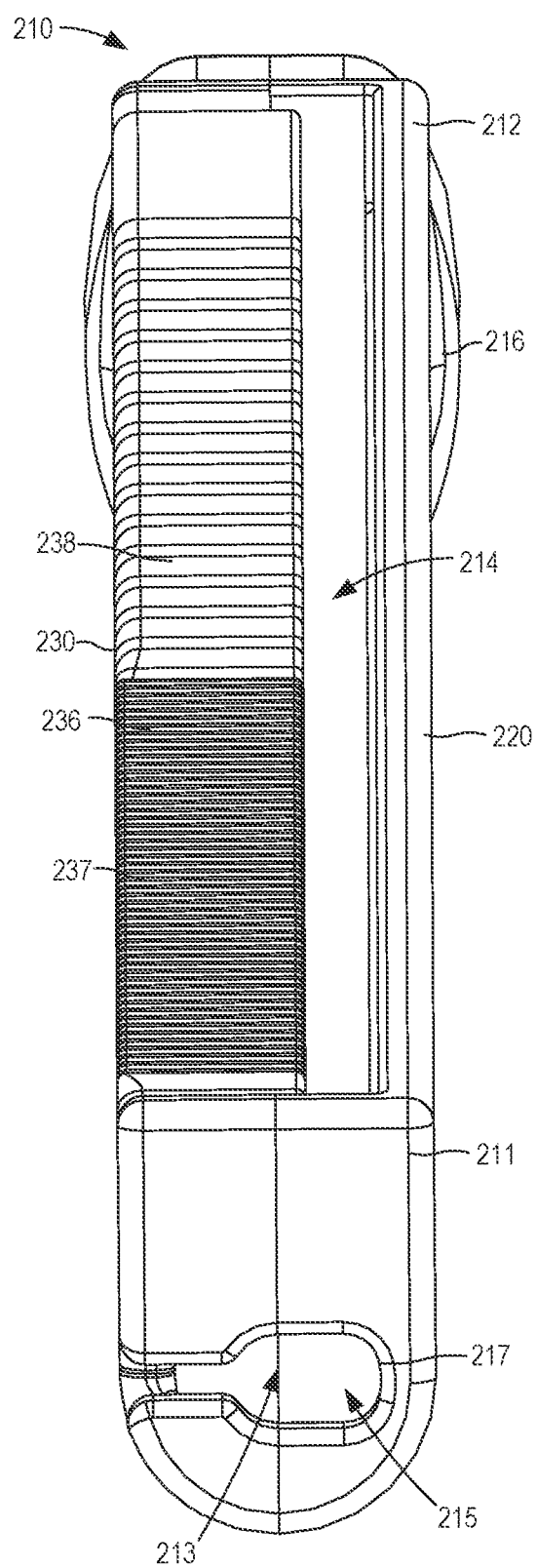
FIG. 10 is a rear perspective view of the introducer formed by coupling the first member illustrated in FIG. 6 to the second member illustrated in FIG. 7.

As shown in FIGS. 10-12, the first member 220 is configured to be coupled to the second member 230 to collectively form the introducer 210. For example, in some embodiments, the first member 220 and the second member 230 can be coupled via ultrasonic welding, an adhesive, a mechanical fastener, one or more tabs, snaps, pins, and/or the like to form the introducer 210. In some embodiments, coupling the first member 220 to the second member 230 (e.g., during a manufacturing process) to form the introducer 210 can facilitate and/or simplify one or more manufacturing processes. For example, in some embodiments, forming the introducer 210 from the first member 220 and the second member 230 can reduce undesirable variations in the shape and/or size of the inner surface 223 and 233 (e.g., due to draft angles and/or manufacturing tolerances) during manufacturing, which in some instances, can reduce a likelihood of kinks, bends, and/or deformations of the catheter 260 during use of the transfer device 200. In some embodiments, forming the introducer 210 from the first member 220 and the second member 230 can allow at least the inner surface 223 of the first member 220 to form a tortuous shape that would otherwise present challenges when manufacturing the introducer 210 from a single work piece.

In other embodiments, a first member 220 can be monolithically formed (e.g., via injection molding and/or any other suitable manufacturing process). That is to say, the first member 220 can be formed from a single work piece or the like rather than two work pieces, namely, the first member 220 and the second member 230. Thus, when referring to features of the first member 220, such features can be formed and/or defined by the first member 220, formed and/or defined by the second member 230, collectively formed and/or defined by the first member 220 and the second member 230, or, when the introducer 210 is formed from a single work piece, formed and/or defined by a corresponding portion of the introducer 210.

The first member 220 and the second member 230 collectively form a proximal end portion 211 and a distal end portion 212 of the introducer 210 and collectively define an inner volume 213 of the introducer 210. As shown in FIG. 10, the proximal end portion 211 of the introducer 210 defines an opening 217. Specifically, the opening 217 is collectively formed and/or defined by the notch 226 of the first member 220 and the notch 234 of the second member 230. The arrangement of the proximal end portion 211 is such that a portion of the opening 217 defined by the notch 226 of the first member 220 has a first size and/or shape and a portion of the opening 217 defined by the notch 234 of the second member 230 has a second size and/or shape that is less than the first size and/or shape. In other words, a portion of the opening 217 is constricted, pinched, obstructed, and/or otherwise reduced. As described in further detail herein, the opening 217 is configured to receive a portion of the secondary catheter 265, which can be moved within the opening 217 from the larger portion of the opening 217 to the reduced portion of the opening 217 (e.g., the portion formed by the notch 234 of the second member 230) to obstruct, pinch, and/or clamp the secondary catheter 265.

As shown in FIG. 11, the distal end portion 212 of the introducer 210 includes and/or otherwise forms a coupler 216. In other words, the distal end portion 222 of the first member 220 and the distal end portion 232 of the second member 230 collectively form the coupler 216 at the distal end portion 212 of the introducer 210. The coupler 216 can be any suitable shape, size, and/or configuration. For example, in this embodiments, the coupler 216 forms a set of threads, which can form a threaded coupling with an associated threaded portion of the lock 240, as described in further detail herein. Although not shown in FIG. 11, the distal end portion 211 of the introducer 210 can include and/or can be configured to receive a seal that can selectively seal and/or fluidically isolate the inner volume 213 of the introducer 210 (at least from an open portion of the coupler 216). In use, the seal can be transitioned from a sealed or closed configuration to an open configuration to allow, for example, a portion of the catheter 260 to pass therethrough. In some embodiments, the seal can contact an outer surface of the catheter 260 to define a seal therebetween that is operable to limit and/or substantially prevent a back flow of fluid between the outer surface of the cannula and the seal.

The seal can be any suitable type of seal. For example, in some embodiments, the seal can be an O-ring, a one-way valve, a diaphragm, a self-healing diaphragm, a check valve, a single crack valve, and/or any other suitable seal or valve member. In some embodiments, the seal is configured to define and/or otherwise have a predetermined "cracking" pressure. That is to say, in some embodiments, the seal can be configured to transition from a closed and/or sealed configuration to a substantially open configuration in response to an increase in pressure, for example, within the introducer 210. In some embodiments, the seal can be a positive pressure seal or the like. In other embodiments, the seal can be a fluid seal such as a saline lock or the like. Although not shown in FIGS. 5-12, in some embodiments, the introducer 210 can include a device, mechanism, assembly, and/or the like, which can be manipulated to increase a pressure (e.g., via air or other suitable fluid or liquid) within the introducer 210 to transition the seal from the closed configuration to the open configuration. For example, the introducer 210 can include and/or can be coupled to a bulb, pump, a syringe, a fluid source, a mechanical actuator, an electric actuator, and/or the like. In other embodiments, the seal can be any other suitable configuration.

The inner surface 223 of the first member 220 and the inner surface 233 of the second member 230 collectively define the inner volume 213 of the introducer 210. As shown in FIG. 12, the arrangement of the inner surfaces 223 and 233 is such that the inner volume 213 has and/or defines a tortuous cross-sectional shape. For example, the inner volume 213 can have a substantially S-shaped or an at least partially S-shaped cross-sectional shape. More specifically, the inner surface 223 of the first member 220 includes and/or forms a ridge, tab, flange, protrusion, and/or wall configured to separate the first portion 224 of the inner surface 223 from the second portion 225 of the inner surface 223. Thus, the tortuous cross-sectional shape of the inner volume 213 forms and/or defines a first portion 214 of the inner volume 213 and a second portion 215 of the inner volume 213. In this manner, the first portion 214 of the inner volume 213 is spaced apart from the second portion 215 of the inner volume 213 without being fluidically isolated therefrom. In other words, the first portion 214 of the inner volume 213 defines an axis that is parallel to and offset from an axis defined by the second portion 215 of the inner volume 213.

As shown in FIG. 12, the first portion 214 of the inner volume 213 extend through a wall of the introducer 210. Similarly stated, the introducer 210 defines (e.g., the first member 220 and the second member 230 collectively define) a slot, channel, track, opening, and/or the like that is in fluid communication with the first portion 214 of the inner volume 213. Conversely, the second portion 215 of the inner volume 213 is entirely defined and/or enclosed (at least in the circumferential direction) by the introducer 210. The tortuous cross-sectional shape of the inner volume 213 is such that the second portion 215 cannot be viewed (e.g., is out of the line of sight) via the slot (in fluid communication with the first portion 214 of the inner volume 213), which in turn, can limit and/or substantially prevent contamination of the catheter 260 disposed therein.

In this embodiment, the second portion 215 of the inner volume 213 is substantially aligned with, for example, a portion of the opening 217 and a portion of an opening defined by the coupler 216. Moreover, the second portion 215 of the inner volume 213 is configured to be substantially aligned with the lock 240 when the lock is coupled to the coupler 216 of the introducer 210. In other words, the axis defined by the second portion 215 of the inner volume 213 is substantially co-axial with an axis defined by a portion of the lock 240, as described in further detail herein. In this manner, the second portion 215 of the inner volume 213 can movably receive, for example, a portion of the actuator 270 and a portion of the catheter 260. Thus, the actuator 270 can be moved relative to the introducer 210 to move the catheter 260 between a first position, in which the catheter 260 is entirely disposed within the second portion 215 of the inner volume 213, and a second position, in which at least a portion of the catheter 260 extends outside of the second portion 215 of the inner volume 213 and distal to the introducer 210, as described in further detail herein.

Figure 13:
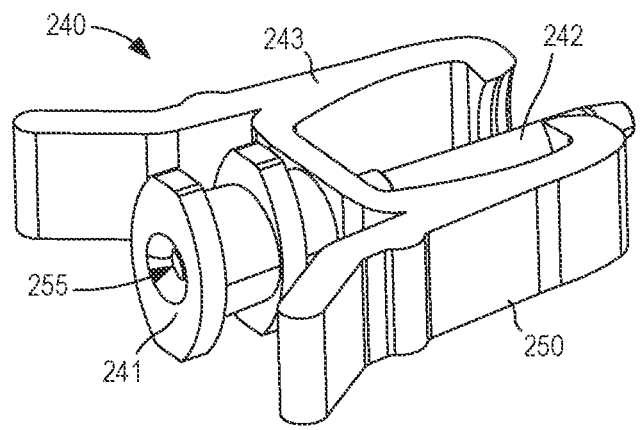
FIGS. 13 and 14 are a rear perspective view and a top view, respectively, of a lock included in the fluid transfer device of FIG. 3.
Figure 14:
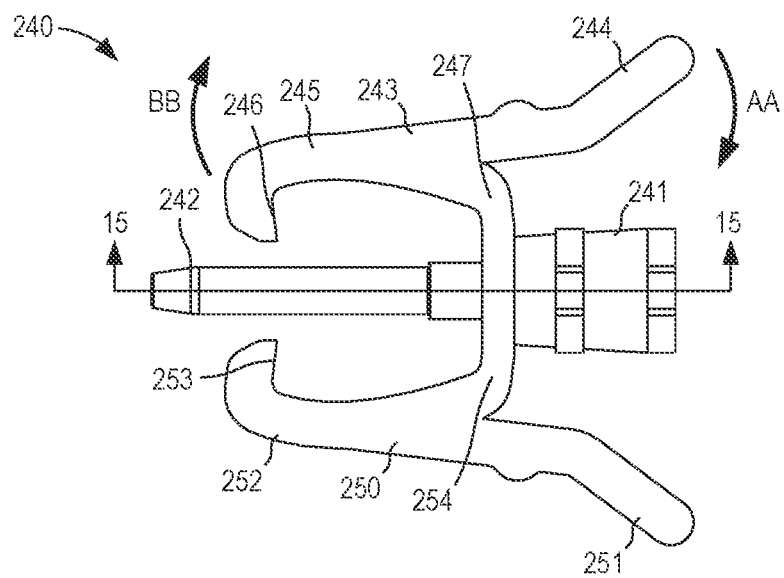
Figure 15:
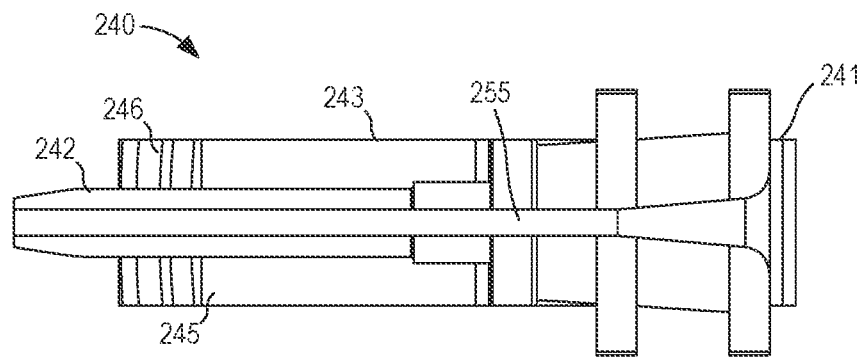
FIG. 15 is a cross-sectional view of the lock taken along the line 15-15 in FIG. 14.

The lock 240 of the transfer device 200 can be any suitable shape, size, and/or configuration. As described above, the lock 240 is configured to be physically and fluidically coupled to the introducer 210 and configured to couple the introducer 210 to the PIV and/or any suitable intermediate device or adapter coupled to the PIV. The lock 240 has a coupler 241, a proboscis 242, a first arm 243, and a second arm 250, as shown in FIGS. 13-15. In addition, the lock 240 defines a lumen 255 extending through the coupler 241 and the proboscis 242. The coupler 241 is configured to couple the lock 240 to the coupler 216 of the introducer 210. Specifically, in this embodiment, the coupler 241 includes and/or forms one or more protrusions configured to selectively engage the threads defined and/or formed by the coupler 216 of the introducer 210, thereby forming a threaded coupling.

The proboscis 242 extends from the coupler 246 and is disposed between the first arm 243 and the second arm 250. The proboscis 242 can be any suitable shape, size, and/or configuration. In some embodiments, the configuration of the proboscis 242 can be associated with or at least partially based on a size and/or shape of the PIV, a size and/or shape of an adapter (e.g., an extension set, a Y-adapter, a T-adapter, or the like), or a collective size and/or shape of the PIV and the adapter. For example, in some embodiments, the proboscis 242 can have a length that is sufficient to extend through at least a portion of the PIV (or adapter). In embodiments including an adapter coupled to the PIV, the proboscis 242 can be sufficiently long to extend through the adapter and at least partially into or through the PIV. In some embodiments, the proboscis 242 can be sufficiently long to extend through an adapter and the PIV such that at least a portion of the proboscis 242 is distal to the PIV. Moreover, the proboscis 242 can have an outer diameter that is similar to or slightly smaller than an inner diameter of a portion of the PIV and/or adapter coupled thereto. For example, in some embodiments, an outer surface of the proboscis 242 can be in contact with an inner surface of the PIV when the proboscis 242 is disposed therein. In this manner, the proboscis 242 can provide structural support to at least a portion of the PIV within which the proboscis 242 is disposed. Similarly, the proboscis 242 can have an inner diameter (a diameter of a surface at least partially defining the lumen 255) that is similar to or slightly larger than an outer diameter of a portion of the catheter 260, as described in further detail herein.

The first arm 243 and the second arm 250 of the lock 240 can be any suitable shape, size, and/or configuration. As shown in FIGS. 13 and 14, the first arm 243 has a first end portion 244, a second end portion 245 including a tab 246, and a pivot portion 247 disposed between the first end portion 244 and the second end portion 245. The tab 246 disposed at and/or formed by the second end portion 245 extends from the second end portion 245 toward, for example, the proboscis 242. In this manner, the tab 246 can selectively engage a portion of the PIV and/or a portion of an adapter coupled to the PIV to couple the lock 240 thereto, as described in further detail herein.

The pivot portion 247 of the first arm 243 extends from the coupler 241, proboscis 242, and/or second arm 250 in a lateral direction. The first end portion 244 and the second end portion 245 of the first arm 243 are proximal to the pivot portion 247 and distal to the pivot portion 247, respectively. As such, the first arm 243 can act as a lever or the like configured to pivot about an axis defined by the pivot portion 247 in response to an applied force. For example, in some instances, a user can exert a force on the first end portion 244 (e.g., toward the coupler 241) that is sufficient to pivot the first end portion 244 of the first arm 243 toward the coupler 241 (as indicated by the arrow AA in FIG. 14) and the second end portion 245 of the first arm 243 away from the proboscis 242 (as indicated by the arrow BB in FIG. 14), as described in further detail herein.

As described above with reference to the first arm 243, the second arm 250 of the lock 240 has a first end portion 251, a second end portion 252 including a tab 253, and a pivot portion 254 disposed between the first end portion 251 and the second end portion 252. In this embodiment, the first arm 243 and the second arm 250 are substantially similar in form and function and are arranged in opposite positions and orientations relative to the coupler 241 and proboscis 242 (e.g., the lock 240 is substantially symmetrical about its longitudinal axis). As such, the discussion of the first arm 243 similarly applies to the second arm 250 and thus, the second arm 250 is not described in further detail herein.

As described above, the lock 240 is configured to be coupled to the PIV and/or an adapter coupled to the PIV. For example, a user can exert a lateral force on the first end portion 244 of the first arm 243 and the first end portion 251 of the second arm 250 to pivot the first arm 243 and the second arm 250, respectively, from a first position toward a second position. The pivoting of the first arm 243, therefore, increases a space defined between the proboscis 242 and the second end portion 245 (and the tab 246) of the first arm 243. Similarly, the pivoting of the second arm 250 increases a space defined between the proboscis 242 and the second end portion 252 (and the tab 253) of the second arm 250. In this manner, the increased space between the proboscis 242 and the arms 243 and 250 is sufficient to allow a portion of the PIV and/or an adapter coupled to the PIV to be inserted within the space. Once the portion of the PIV and/or the adapter is in a desired position relative to the lock 240, the user can remove the force and in turn, the arms 243 and 250 pivot toward their respective first positions. As a result, the second end portions 245 and 252 are moved toward the proboscis 242 until the tabs 246 and 253, respectively, are placed in contact with a portion of the PIV and/or the adapter. The tabs 246 and 253 are configured to engage the portion of the PIV and/or adapter to temporarily couple the lock 240 to the PIV and/or adapter. In some embodiments, the lock 240 can be configured to establish three points of contact with the PIV and/or the adapter, namely, the tabs 246 and 253, and an outer surface of the proboscis 242 (as described above). In some embodiments, the tabs 246 and 253 can be configured to produce an audible output such as a click, a vibratory output such as a haptic bump, and/or the like when placed in contact with the portion of the PIV and/or adapter, which can indicate to a user that the lock 240 is properly coupled to the PIV and/or adapter.

As shown in FIG. 15, the proboscis 242 and the coupler 241 collectively define the lumen 255. The lumen 255 of the lock 240 defines an axis (not shown) that is aligned with and/or substantially co-axial with the axis defined by the second portion 215 of the inner volume 213. Thus, the lumen 255 of the lock 240 receives a portion of the catheter 260 when the transfer device 200 is transitioned between the first configuration and the second configuration. In some embodiments, the lumen 255 can have a size and/or shape that is based at least in part on a size and/or shape of the catheter 260. For example, the lumen 255 can have an inner diameter that is slightly larger than an outer diameter of at least a portion of the catheter 260. In such embodiments, the lock 240 can be and external guide or the like that can support and/or guide the catheter 260 as the catheter 260 is moved within the lumen 255, which in turn, can reduce and/or substantially prevent undesirable bending, kinking, flexing, and/or deforming of the catheter 260.

Although the lock 240 is shown and described above as including the proboscis 242, in other embodiments, a lock need not form a proboscis. For example, in some such embodiments, a lock can include a relatively short hub or the like configured to engage a portion of the PIV and/or an adapter coupled to the PIV. In some embodiments, a fluid transfer device can include and/or can be used with a proboscis or guide member (not formed with or by the lock) configured to be disposed, for example, between a PIV and an adapter such as an IV extension set. For example, such a proboscis or guide member can have an inner surface that is funnel shaped and/or is shaped similar to the inner surface of the proboscis 242. In this manner, the inner surface of such a proboscis and/or guide member can guide a portion of the catheter 260 as the catheter 260 is moved between the first position and the second position. In some embodiments, the lock 240 (including the proboscis 242) can be used in conjunction with such an external or separate proboscis and/or guide member. In some such embodiments, a portion of the proboscis 242 of the lock 240 can be inserted into the proboscis and/or guide member when the lock 240 is coupled to the adapter (e.g., IV extension set).

Figure 16:
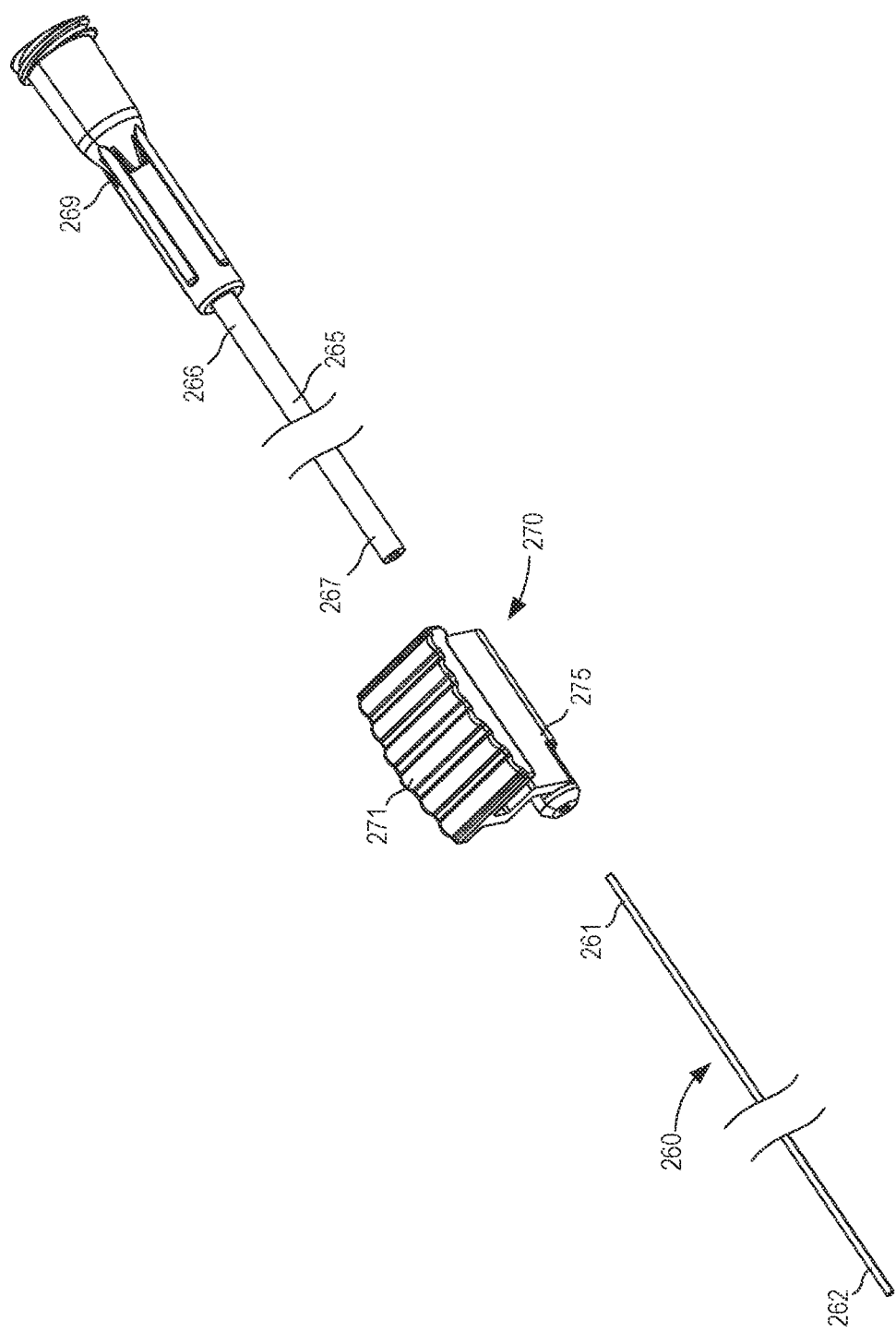
FIG. 16 is an exploded perspective view a catheter, a secondary catheter, and an actuator included in the fluid transfer device of FIG. 3.
Figure 17:
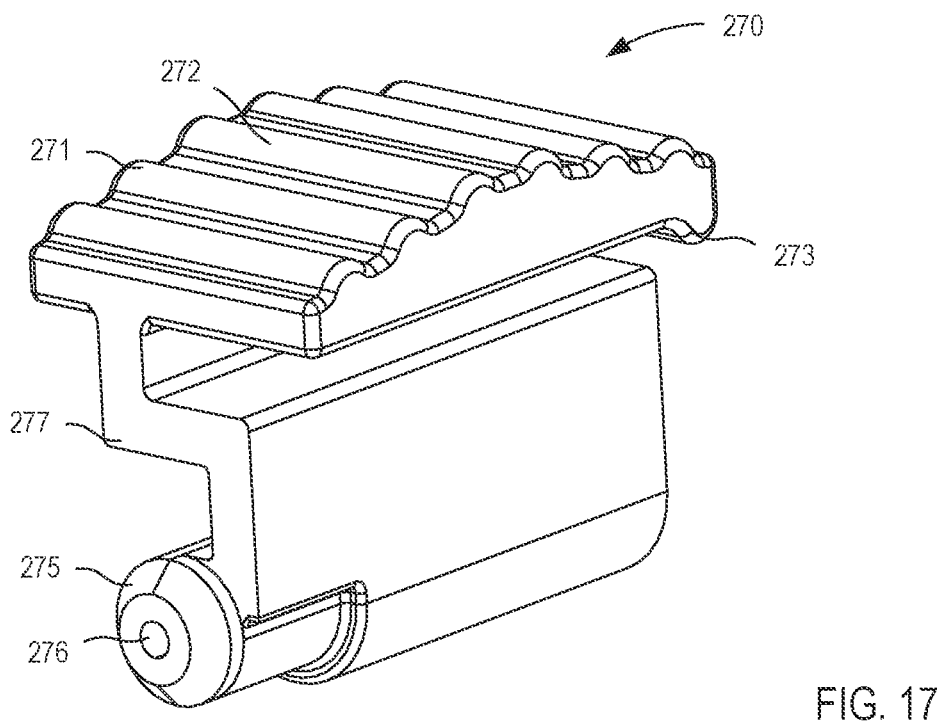
FIGS. 17-19 are a perspective view, a side view, and a front view, respectively, of the actuator illustrated in FIG. 16.

As described above, at least a portion of the catheter 260 and at least a portion of the secondary catheter 265 is movably disposed within the second portion 215 of the inner volume 213 defined by the introducer 210. As shown in FIG. 16, the catheter 260 has a proximal end portion 261 and a distal end portion 262 and defines a lumen 263 (see e.g., FIG. 24). The proximal end portion 261 of the catheter 260 is coupled to a second portion 275 of the actuator 270. In this manner, the actuator 270 can be moved relative to the introducer 210 to move the catheter 260 between a first position, in which the catheter 260 is disposed within the introducer 210 (e.g., the entire catheter 260 is disposed within the introducer 210 or within the introducer 210 and the lock 240) and a second position, in which the distal end portion of the catheter 260 is at least partially disposed in a position distal to the lock 240 and/or the PIV (not shown) when the lock 240 is coupled to the PIV, as described in further detail herein. The distal end portion 262 can be any suitable shape, size, and/or configuration and can define at least one opening in fluid communication the lumen 263. For example, in some embodiments, the distal end portion 262 of the catheter can be substantially similar to any of those described in U.S. Pat. No. 8,366,685 (referred to herein as the "'685 patent") entitled. "Systems and Methods for Phlebotomy Through a Peripheral IV Catheter." filed on Apr. 26, 2012, the disclosure of which is incorporated herein by reference in its entirety.

The catheter 260 can be any suitable shape, size, and/or configuration. For example, in some embodiments, at least a portion of the catheter 260 can have an outer diameter that is substantially similar to or slightly smaller than an inner diameter defined by the lumen 255 of the lock 240, as described above. In some embodiments, an outer surface of the catheter 260 can be configured to contact an inner surface of the lock 240 that defines at least a portion of the lumen 255. In this manner, an inner surface of the portion of the lock 240 defining the lumen 255 can guide the catheter 260 as the catheter 260 is moved between the first position and the second position. In some embodiments, such an arrangement can limit and/or can substantially prevent bending, deforming, and/or kinking of the catheter 260 as the catheter 260 is moved between the first position and the second position. Moreover, in some embodiments, the catheter 260 can have a length that is sufficient to place a distal surface of the catheter 260 in a desired position relative to a distal surface of the PIV when the catheter 260 is in the second position. In other words, the length of the catheter 260 can be sufficient to define a predetermined and/or desired distance between the distal surface of the catheter 260 and the distal surface of the PIV when the catheter 260 is in the second position, as described in further detail herein.

The catheter 260 can be formed from any suitable material or combination of materials, which in turn, can result in the catheter 260 having any suitable stiffness or durometer. For example, in some embodiments, the catheter 260 can be formed of a relatively flexible biocompatible material with a Shore durometer of approximately 20 Shore A to 50 Shore D; approximately 20 Shore A to 95 Shore D; approximately 70 Shore D to 85 Shore D, and/or any other suitable range of Shore durometer. In some embodiments, at least a portion of the catheter 260 can be formed of a braided material or the like, which can modify, change, and/or alter a flexibility of the catheter 260 in response to a bending force or the like. In other words, forming at least a portion of the catheter 260 from the braided material can increase an amount of deformation (in response to a bending force) of the catheter 260 prior buckling, kinking, and/or otherwise obstructing the lumen 263 of the catheter 260. Similarly, forming at least a portion of the catheter 260 of a braided material can result in a compression and/or deformation in response to a compression force exerted in a direction of a longitudinal centerline defined by the catheter 260 (e.g., an axial force or the like). In this manner, the catheter 260 can absorb a portion of force associated with, for example, impacting an obstruction or the like. In some instances, such an arrangement can reduce buckling and/or kinking of the catheter 260 as well as reduce and/or substantially prevent damage to vascular structures that may otherwise result from an impact of the catheter 260. Moreover, in some embodiments, forming at least a portion of the catheter 260 from the braided material, for example, can increase an amount of vibration transmitted through the catheter 260 in response to the portion of the actuator 270 advancing along the set of ribs 236 of the introducer 210 (as described above). While the catheter 260 is described above as including at least a portion formed of a braided material, in other embodiments, at least a portion of the catheter 260 can be formed of and/or can include a support wire, a stent, a fenestrated catheter, and/or the like such as those described in the '685 patent incorporated by reference above.

Figure 24:
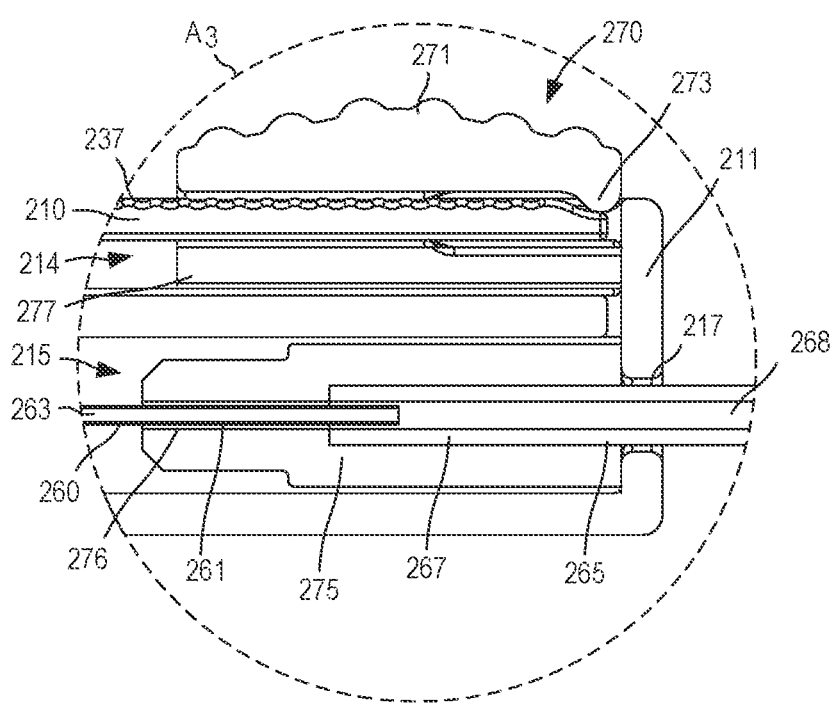
FIG. 24 is an enlarged cross-sectional view of a portion of the fluid transfer device identified by the region A3 in FIG. 22.
Figure 25:
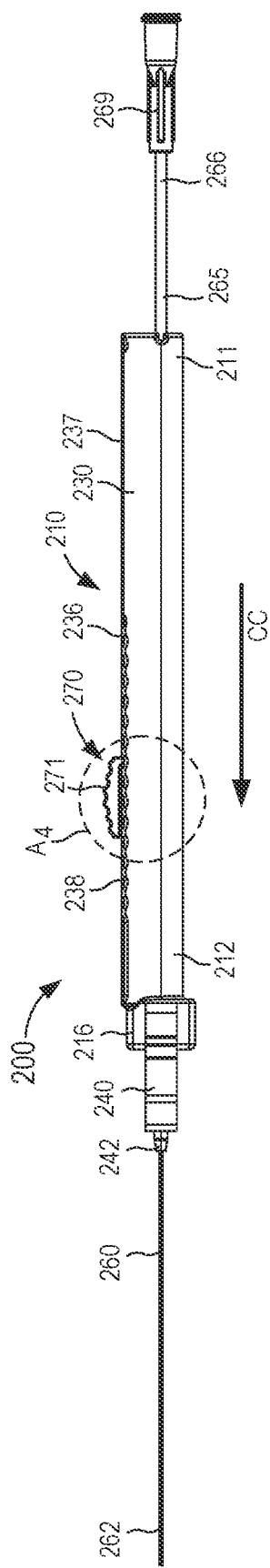
FIG. 25 is a side view of the fluid transfer device of FIG. 3 as the fluid transfer device is being transitioned from the first configuration to a second configuration.
Figure 26:
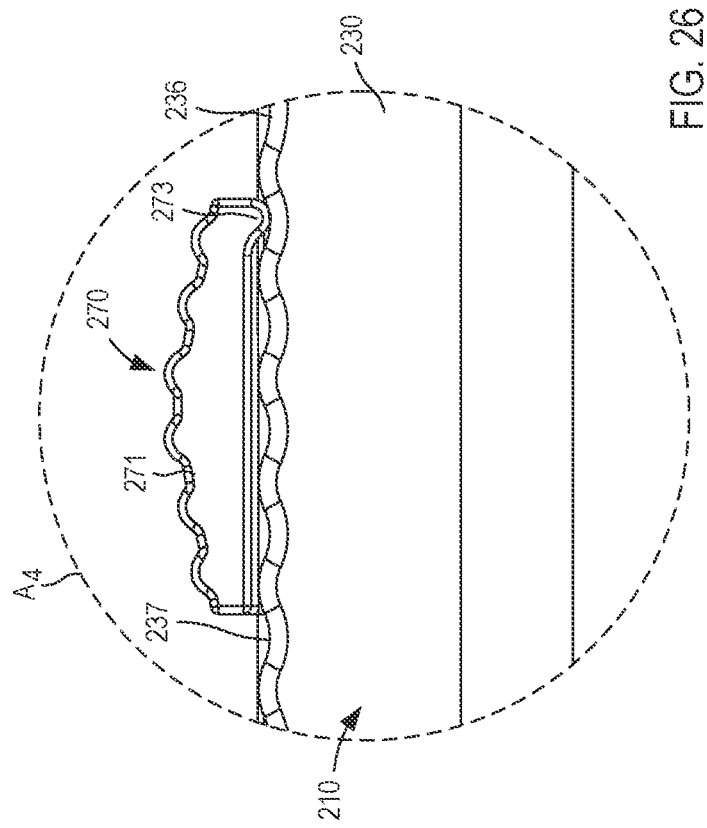
FIG. 26 is an enlarged view of a portion of the fluid transfer device identified by the region A4 in FIG. 24.

The secondary catheter 265 has a proximal end portion 266 and a distal end portion 267 and defines a lumen 268 (see e.g., FIG. 24). A portion of the secondary catheter 265 is disposed within and extends through the opening 217 of the introducer 210 (e.g., collectively defined by the notches 223 and 233 of the first member 220 and second member 230, respectively). As such, the proximal end portion 266 is at least partially disposed outside of the introducer 210 and the distal end portion 267 is at least partially disposed within the second portion 215 of the inner volume 213 defined by the introducer 210. As described above, the secondary catheter 265 can be moved within the opening 217 between a first position and a second position to selectively clamp, pinch, kink, bend, and/or otherwise deform a portion of the secondary catheter 265, which in turn, obstructs, pinches, kinks, closes, seals, etc. the lumen 268 of the secondary catheter 265. For example, the first position can be associated and/or aligned with a first portion of the opening 217 having a larger perimeter and/or diameter than a perimeter and/or diameter of a second portion of the opening 217 associated and/or aligned with the second position. Thus, a user can manipulate the secondary catheter 265 to occlude the lumen 268 of the secondary catheter 265, thereby limiting, restricting, and/or substantially preventing a flow of a fluid therethrough.

As shown in FIG. 16, the proximal end portion 266 of the secondary catheter 265 is coupled to and/or otherwise includes a coupler 269. The coupler 269 is configured to physically and fluidically couple the secondary catheter 265 to any suitable device such as, for example, a fluid reservoir, fluid source, syringe, evacuated container holder (e.g., having a sheathed needle or configured to be coupled to a sheathed needle), pump, and/or the like. The distal end portion 267 of the secondary catheter 265 is at least partially disposed within the second portion 215 of the inner volume 213 defined by the introducer 210 and is coupled to the second portion 275 of the actuator 270. In some embodiments, the secondary catheter 265 can have a larger diameter than the catheter 260 such that the proximal end portion 261 of the catheter 260 is at least partially disposed within the lumen 268 defined by the secondary catheter 265 when the catheter 260 and the secondary catheter 265 are coupled to the second portion 275 of the actuator 270. In some embodiments, such an arrangement can, for example, reduce and/or substantially prevent leaks associated with fluid flowing between the catheter 260 and the secondary catheter 265. In some embodiments, such an arrangement can also limit, reduce, and/or substantially prevent hemolysis of a volume of blood as the volume of blood flows through the catheter 260 and the secondary catheter 265. In this manner, when the coupler 269 is coupled to a fluid reservoir, fluid source, syringe, evacuated container, pump, etc., the secondary catheter 265 establishes fluid communication between the reservoir, source, pump, etc. and the catheter 260.

The actuator 270 of the transfer device 200 is coupled to the catheter 260 can be moved along a length of the introducer 210 to transition the transfer device 200 between its first configuration, in which the catheter 260 is in the first position, and its second configuration, in which the catheter 260 is in the second position. The actuator 270 can be any suitable shape, size, and/or configuration. For example, in some embodiments, the actuator 270 can have a size and shape that is associated with and/or based at least in part on a size and/or shape of the introducer 210.

As shown in FIGS. 17-20, the actuator 270 includes a first portion 271, the second portion 275, and a wall 277 extending therebetween. The first portion 271 of the actuator 270 is at least partially disposed within the first portion 214 of the inner volume 213 defined by the introducer 210 and the second portion 275 of the actuator 270 is disposed within the second portion 215 of the inner volume 213, as described above. The first portion 271 of the actuator 270 includes an engagement member 272. The arrangement of the actuator 270 is such that the engagement member 272 is disposed outside of the introducer 210 while the rest of the first portion 271 is within the first portion 214 of the inner volume 213 defined by the introducer 210. As such, the engagement member 272 can be engaged and/or manipulated by a user (e.g., by a finger or thumb of the user) to move the actuator 270 relative to the introducer 210. In some embodiments, the engagement member 272 can include a set of ridges and/or any suitable surface finish that can, for example, increase the ergonomics of the actuator 270 and/or transfer device 200.

The engagement member 272 includes a tab 273 disposed at or near a proximal end portion of the engagement member 272. The tab 273 can be any suitable tab, rail, ridge, bump, protrusion, knob, roller, slider, etc. that extends from a surface of the engagement member 272. The tab 273 is configured to selectively engage the outer surface 235 of the second member 230 of the introducer 210. More specifically, the tab 273 is in contact with the ribs 236 formed by the second member 230 and moves along each successive rib as the actuator 270 is moved along a length of the introducer 210.

Figure 18:
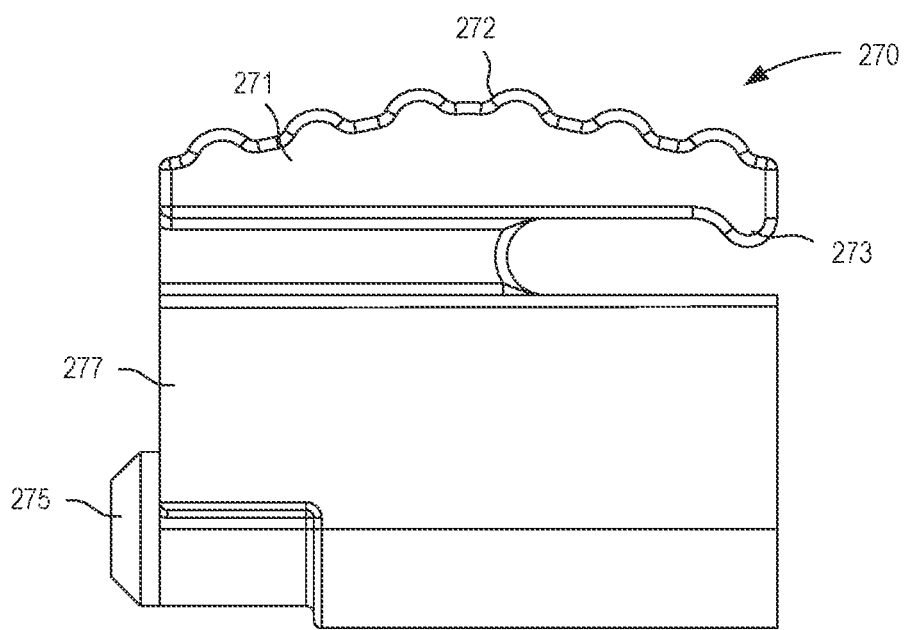

As described above with reference to the set of ribs 236 of the second member 230, the tab 273 can have any suitable shape, size, and/or configuration. For example, as shown in FIG. 18, the tab 273 can include a substantially rounded surface that can be moved along the set of ribs 236. In some embodiments, the size and/or shape of the tab 273 is based at least in part on a size and/or shape of the ribs 236 such that a desired surface area of the tab 273 is in contact with the ribs 236 as the actuator 270 is moved relative to the introducer 210. In some embodiments, an amount of friction defined between the set of ribs 236 and the tab 273 can be based at least in part on a surface area of the tab 273 that is in contact with the set of ribs 236. Moreover, an amount of friction defined between the set of ribs 236 and the tab 273 can be based at least in part on a position of the tab 273 relative to each rib. For example, in some embodiments, an amount of friction defined between the tab 273 and a rib can increase at the tab 273 moves closer to, for example, a local maxima and can decrease as the tab 273 moves away from the local maxima. In some embodiments, the tab 273 can have a size and/or shape that allows the tab 273 to move with substantially less friction between each adjacent rib (e.g., between adjacent local maximums). In other words, the arrangement of the tab 273 and the set of ribs 236 can allow for a desired amount of "play" between adjacent ribs.

With the first portion 237 of the set of ribs 236 having a smaller size than the second portion 238 of the set of ribs 236, a first portion or first surface area of the tab 273 can be in contact with the first portion 237 of the set of ribs 236 and a second portion or second surface area of the tab 273 can be in contact with the second portion 238 of the set of ribs 236. In this manner, the tab 273 can move along the first portion 237 with a first set of characteristics and can move along the second portion 238 with a second set of characteristics different from the first set of characteristics. In some embodiments, for example, a force sufficient to move the tab 273 along the second portion 238 of the set of rib 236 can be greater than a force otherwise sufficient to move the tab 273 along the first portion 237 of the set of ribs 236. In some embodiments, the movement of the tab 273 along the second portion 238 of the set of ribs 236 can result in, for example, a larger amount of vibration of the actuator 270 than an amount of vibration otherwise resulting from the movement of the tab 273 along the first portion 237 of the set of ribs 236. Similarly, the shape of the tab 273 can be such that the tab 273 moves along the set of ribs 236 in the distal direction in response to an applied force that is insufficient to move the tab 273 along the set of ribs 236 in the proximal direction. For example, as shown in FIG. 18, the tab 273 has an asymmetric shape, wherein a proximal surface of the tab 273 has a greater pitch than a pitch of its distal surface.

While the engagement member 272 and tab 273 are particularly shown and described above, in other embodiments, an actuator can include an engagement member and/or tab having any suitable configuration. For example, while the tab 273 is shown as being disposed at or near a proximal end portion of the engagement member 272, in other embodiments, an engagement member can include a first tab disposed at or near a proximal end portion and a second tab disposed at or near a distal end portion, each of which can be selectively in contact with a set of ribs disposed on an outer surface of an introducer. In some embodiments, a space defined between a surface of the wall 277 and a surface of the engagement member 272 can be increased or decreased, which can result in an increase or decrease in an amount of travel of the actuator 270 relative to the introducer 210 in a direction other than an axial direction. That is to say, the increase or decrease in space between the surface of the wall 277 and a surface of the engagement member 272 can result in, for example, an increase or decrease of an amount the actuator 270 can "tilt" relative to the introducer 210. In other embodiments, the arrangement of the engagement member 272, the tab 273, and/or the set of ribs 236 of the introducer 210 can be modified, altered, tuned, adjusted, and/or otherwise changed such that the actuator 270 moves relative to the introducer 210 with a desired set of characteristics. For example, in some embodiments, the arrangement of the actuator 270 and/or introducer 210 can increase or decrease an amount the actuator 270 vibrates as it is moved relative to the introducer 210, increase or decrease an amount of force sufficient to move the actuator 270 relative to the introducer 210, increase or decrease an amount of movement of the actuator 270 relative to the introducer 210 in any suitable direction other than the axial direction (e.g., proximal direction or distal direction), and/or the like.

Figure 19:
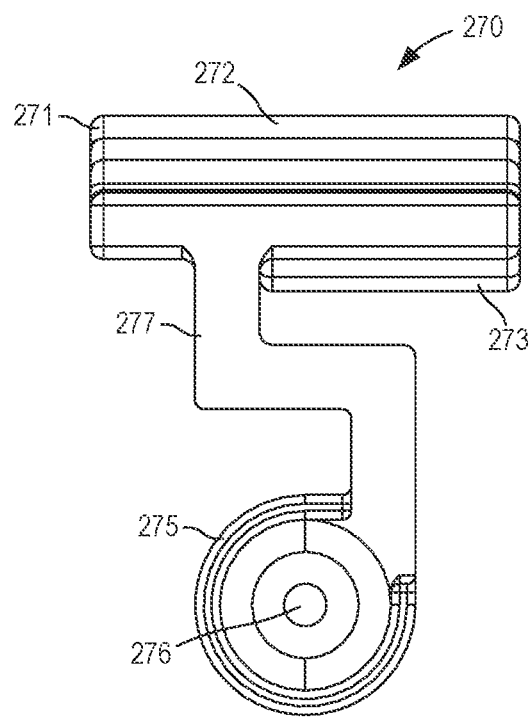
Figure 20:
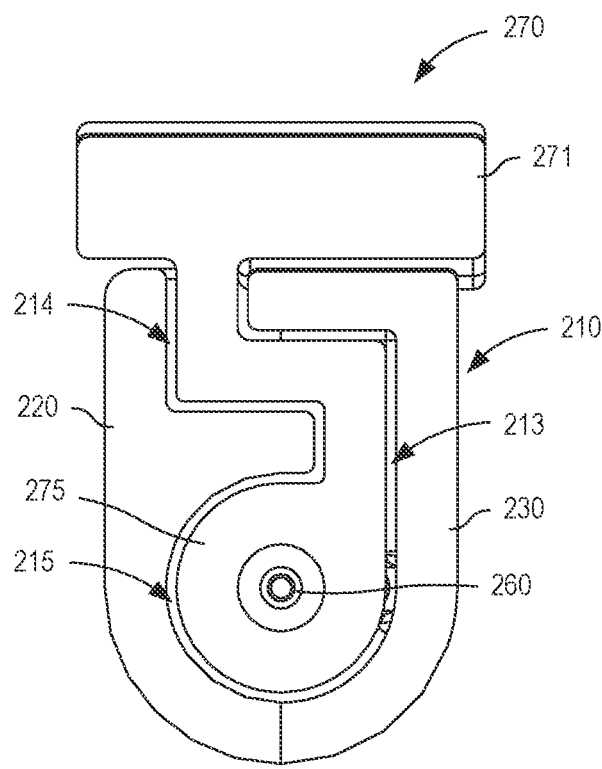
FIG. 20 is a cross-sectional view of the fluid transfer device taken along the line 20-20 in FIG. 4.
Figure 21:
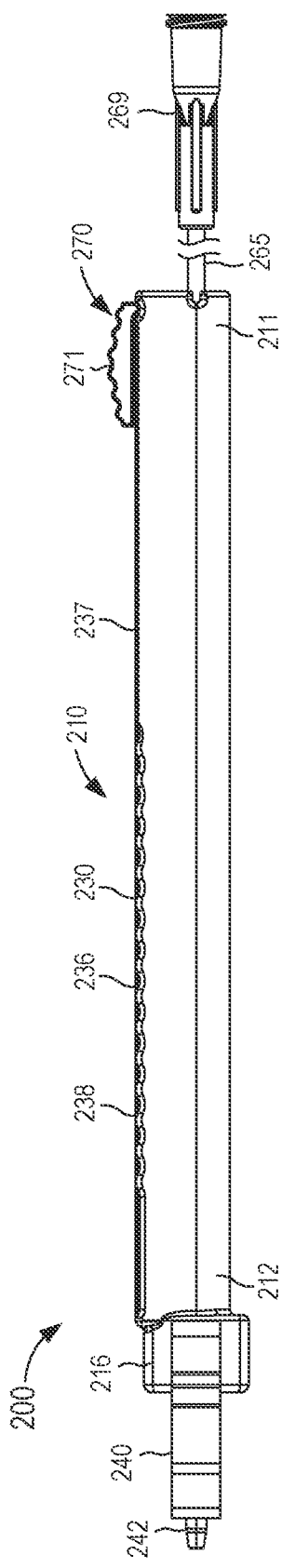
FIG. 21 is a side view of the fluid transfer device of FIG. 3 in the first configuration.
Figure 22:
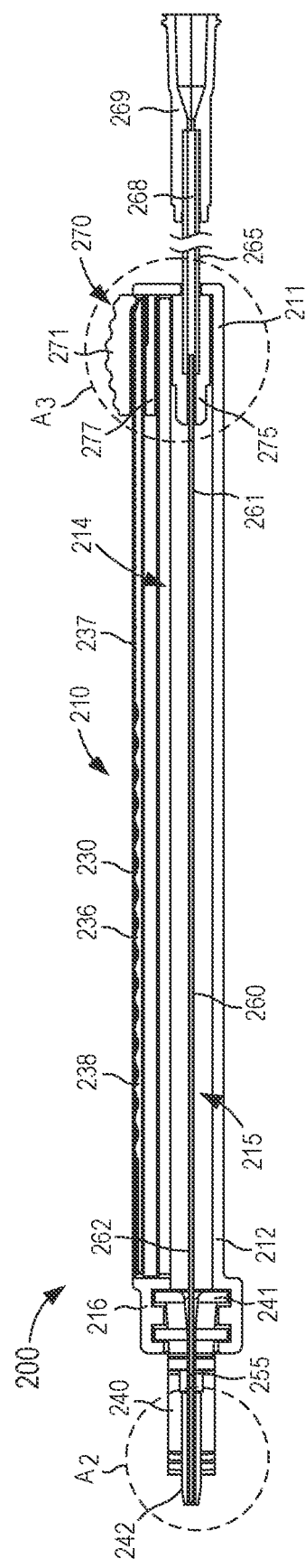
FIG. 22 is a cross-sectional view of the fluid transfer device in the first configuration taken along the line 22-22 in FIG. 3.
Figure 23:
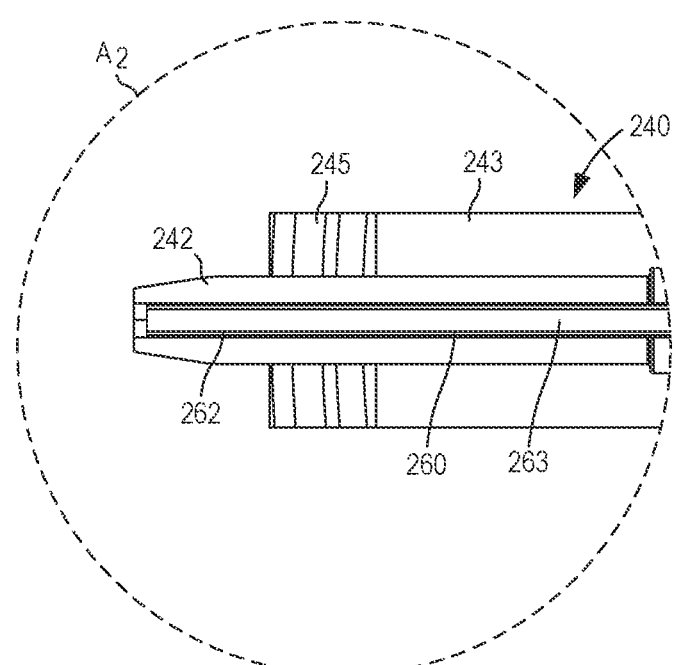
FIG. 23 is an enlarged cross-sectional view of a portion of the fluid transfer device identified by the region A2 in FIG. 22.

As shown, for example, in FIGS. 19 and 20, the second portion 275 has a cross-sectional shape that is based at least in part on a cross-sectional shape of the second portion 215 of the inner volume 213 defined by the introducer 210 (e.g., at least a partially circular cross-sectional shape). In this manner, the inner surface 223 of the first member 220 and the inner surface 233 of the second member 230 can support and/or guide the second portion 275 of the actuator 270 as the actuator 270 moves relative to the introducer 210. As shown, the second portion 275 defines an opening 276 configured to receive a proximal end portion 261 of the catheter 260 and a distal end portion 267 of the secondary catheter 265. In some embodiments, the proximal end portion 261 of the catheter 260 can form a friction fit with an inner surface of the second portion 275 of the actuator 270 when the proximal end portion 261 is disposed in the opening 276. Similarly, the distal end portion 267 of the secondary catheter 265 can form a friction fit with an inner surface of the second portion 275 of the actuator 270 when the distal end portion 267 is disposed in the opening 276. As such, the catheter 260 and the secondary catheter 265 can be maintained in a fixed position relative to the actuator 270 and thus, move concurrently with the actuator 270 as the actuator 270 is moved relative to the introducer 210.

The wall 277 of the actuator 270 couples the first portion 271 of the actuator 270 to the second portion 275 of the actuator 270. As shown in FIGS. 19 and 20, the wall 277 has a tortuous cross-sectional shape that is based at least in part on the tortuous cross-sectional shape of the inner volume 213 defined by the introducer 210. In this manner, the first portion 271 of the actuator 270 can define an axis that is parallel to but offset from an axis defined by the second portion 275 of the actuator 270. In some embodiments, for example, the wall 277 can have a substantially S-shaped or an at least partially S-shaped cross-sectional shape. In some embodiments, the wall 277 can form, for example, a dogleg or the like. The tortuous cross-sectional shape of the wall 277 (and thus, the actuator 270) is such that the second portion 275 of the actuator 270 cannot be viewed (e.g., is out of the line of sight) via the first portion 214 of the inner volume 213 defined by the introducer 210. Similarly, the catheter 260 cannot be viewed via the first portion 214 of the inner volume 213 defined by the introducer 210 when the catheter 260 is in the first position. That is to say, the geometry of the actuator 270 and/or the introducer 210 (e.g., the tortuous cross-sectional shape of the inner volume 213, the height and/or width of the introducer 210, etc.) is configured such that the catheter 260 is at least partially isolated within the second portion 215 of the inner volume 213 when the catheter 260 is in the first position. In this manner, the structure of the introducer 210 and/or the actuator 260 can protect and/or isolate the catheter 260 from a volume outside of the introducer 210, which in turn, can limit and/or substantially prevent contamination of the catheter 260. For example, in some embodiments, the introducer 210 and/or the actuator 270 can act as a "sneeze guard" or the like configured to at least partially isolate the catheter 260 at least when the catheter 260 is in the first position.

Referring now to FIGS. 21-29, the transfer device 200 can be in the first configuration prior to use and can be transitioned by a user (e.g., a doctor, physician, nurse, technician, phlebotomist, and/or the like) from the first configuration (FIGS. 21-24) to the second configuration (FIGS. 27-29) to dispose at least the distal end portion 262 of the catheter 260 in a distal position relative to the introducer 210 (e.g., within an indwelling PIV (not shown) or distal to the indwelling PIV). The transfer device 200 is in the first configuration when the catheter 260 is disposed in the first position 260 within the introducer 210. In some embodiments, substantially the entire catheter 260 is disposed within the introducer 210 when the catheter 260 is in the first position. In such embodiments, the introducer 210 can include the seal or the like (as described above) that can substantially seal the distal end portion 212 of the introducer 210 to isolate the catheter 260 within the second portion 215 of the inner volume 213. In the embodiment shown in FIGS. 22 and 23, however, the catheter 260 is disposed within the introducer 210 and the lock 240 when catheter 260 is in the first position. While the seal is described above as being included in the distal end portion 212 of the introducer 210, in other embodiments, the lock 240 can include a seal or the like that can form a substantially fluid tight seal with an inner surface of the lock 240 that defines the lumen 243. Thus, the seal disposed within the lock 240 can isolate the catheter 260 within the second portion 215 of the inner volume 213. In still other embodiments, the introducer 210 and/or the lock 240 need not include a seal. For example, in some embodiments, a PIV and/or an adapter (e.g., extension set) coupled to the PIV can include a seal that is transitioned from a closed configuration to an open configuration when the lock 240 is coupled thereto. Although not shown, in some embodiments, the catheter 260 can be disposed within a flexible sheath or the like that can maintain the catheter 260 in a substantially sterile environment while the catheter 260 is in the first position (e.g., such as those embodiments in which the introducer 210 and/or lock 240 do not include a seal).

The actuator 270 is disposed in a proximal position when the transfer device 200 is in the first configuration, as shown in FIG. 24. In some embodiments, the tab 273 of the first portion 271 of the actuator 270 can be disposed within a recess or detent or otherwise in contact with a proximal most rib configured to temporarily maintain the actuator 270 in the proximal position until a force is exerted (e.g., by the user) to move the actuator 270 in the distal direction. Moreover, as described above, a portion of the secondary catheter 265 is disposed in the opening 217 defined by the introducer such that the distal end portion 267 is at least partially disposed in the second portion 215 of the inner volume 213 and coupled to the second portion 275 of the actuator 270 while the proximal end portion 266 of the secondary catheter 265 is disposed outside of the introducer 210 (see e.g., FIGS. 21 and 22).

With the transfer device 200 in the first configuration, the user can manipulate the transfer device 200 to couple the lock 240 to an indwelling PIV and/or to an adapter coupled to the PIV (e.g., an extension set or the like). For example, in some embodiments, the user can exert a force sufficient to pivot the first arm 243 and the second arm 250 of the lock 240 such that a portion of the PIV and/or the adapter can be inserted into the space defined between the arms 243 and 250 and, for example, the proboscis 242. In some embodiments, the proboscis 242 can be inserted into the PIV and/or the adapter when the lock 240 is coupled thereto. For example, in some embodiments, a portion of the proboscis 242 can be inserted into a hub or basket of the PIV and/or adapter. As described above, in some embodiments, the proboscis 242 that is sufficiently long to dispose at least a portion of the proboscis 242 within the PIV, which in turn, supports and/or provides structural rigidity to the PIV. Once the PIV and/or adapter is disposed in the desired position relative to the lock 240, the user can remove the force on the arms 243 and 250 of the lock 240, which in turn, move toward proboscis 242 until the tab 246 of the first arm 243 and the tab 253 of the second arm 250 are placed in contact with a surface of the PIV and/or adapter. In some embodiments, the arrangement of the lock 240 is such that the tabs 246 and 253 and the proboscis 242 form three points of contact with the PIV and/or adapter that collectively coupled the lock 240 thereto.

With the transfer device 200 coupled to the PIV and/or adapter, the user can engage the engagement member 272 of the first portion 271 of the actuator 270 to move the actuator 270 relative to the introducer 210, which in turn, moves the catheter 260 from the first position (e.g., disposed within the introducer 210) toward the second position. In this manner, the catheter 260 is moved through the second portion 215 of the inner volume 213 and the lumen 255 of the lock 240 and as such, at least the distal end portion 262 of the catheter 260 is disposed outside of and distal to the lock 240, as indicated by the arrow CC in FIG. 25. In some embodiments, the arrangement of the lumen 255 of the lock 240 and the catheter 260 can be such that an inner surface of the lock 240 defining the lumen 255 contacts, supports, and/or otherwise guides the catheter 260 as the catheter 260 is moved in the distal direction toward the second position. Moreover, in some embodiments, moving the catheter 260 from the first position toward the second position can be operable to transition the seal (e.g., disposed in the lock 240) from a closed or sealed configuration to an open configuration. In other embodiments, the user can manipulate the transfer device 200 (e.g., prior to moving the catheter 260 from the first position) to transition the seal from the sealed configuration to the open configuration. For example, in some embodiments, the user can increase a pressure within at least a portion of the transfer device 200 (e.g., the catheter 260 and/or the lock 240) beyond a predetermined threshold to transition the seal to the open configuration. In some embodiments, the seal can be a one way valve (e.g., a positive pressure valve or seal) that can be transitioned from the sealed configuration to the open configuration, for example, when a pressure exerted on a proximal portion of the seal exceeds a pressure exerted on a distal portion of the seal (e.g., venous pressure exerted on the seal).

As described above, the arrangement of the actuator 270 and the introducer 210 is such that advancing the actuator 270 relative to the introducer 210 advances the tab 273 along the outer surface 235 and more specifically, the set of ribs 236 of the second member 230 of the introducer 210. As shown, for example, in FIG. 26, the tab 273 is in contact with the set of ribs 236, which can produce a vibration of the actuator 270 as the actuator 270 is moved relative to the introducer 210. In some instances, the vibration of the actuator 270 can produce, for example, a haptic, tactile, and/or audible output that can provide an indication associated with a position of the distal end portion 262 of the catheter 260 relative to the introducer 210, lock 240, and/or PIV. For example, in some embodiments, the tab 273 of the actuator 270 and the set of ribs 236 can collectively produce a "click" sound as the tab 273 moves past each rib. In some embodiments, the introducer 210 can include indicia or the like that can indicate to the user the relative position of the distal end portion 262 of the catheter 260. In other embodiments, the amount of times the actuator 270 has vibrated due to being moved relative to that number of ribs can be associated with and/or otherwise provide an indication of the relative position of the distal end portion 262 of the catheter 260.

In some instances, the user can stop moving the actuator 270 relative to the introducer 210 based on the haptic, tactile, and/or audible output indicating a desired placement of the distal end portion 262 of the catheter 260 relative to the PIV (e.g., the second position). In other words, the catheter 260 can be placed in the second position prior to the actuator 270 being advanced, for example, to a distal most position. As described in further detail herein, the catheter 260 is disposed in the second position when the distal end portion 262 of the catheter 260 is placed in a desired position relative to a distal end portion of the PIV. In some instances, for example, a distal end of the catheter 260 can be substantially flush with a distal end of the PIV when the catheter 260 is in the second position. In other instances, the distal end of the catheter 260 can extend a predetermined distance beyond the distal end of the PIV (e.g., distal to the distal end of the PIV). In still other instances, the distal end of the catheter 260 can be disposed within the PIV (e.g., proximal to the distal end of the PIV) when the catheter 260 is in the second position.

Figure 29:
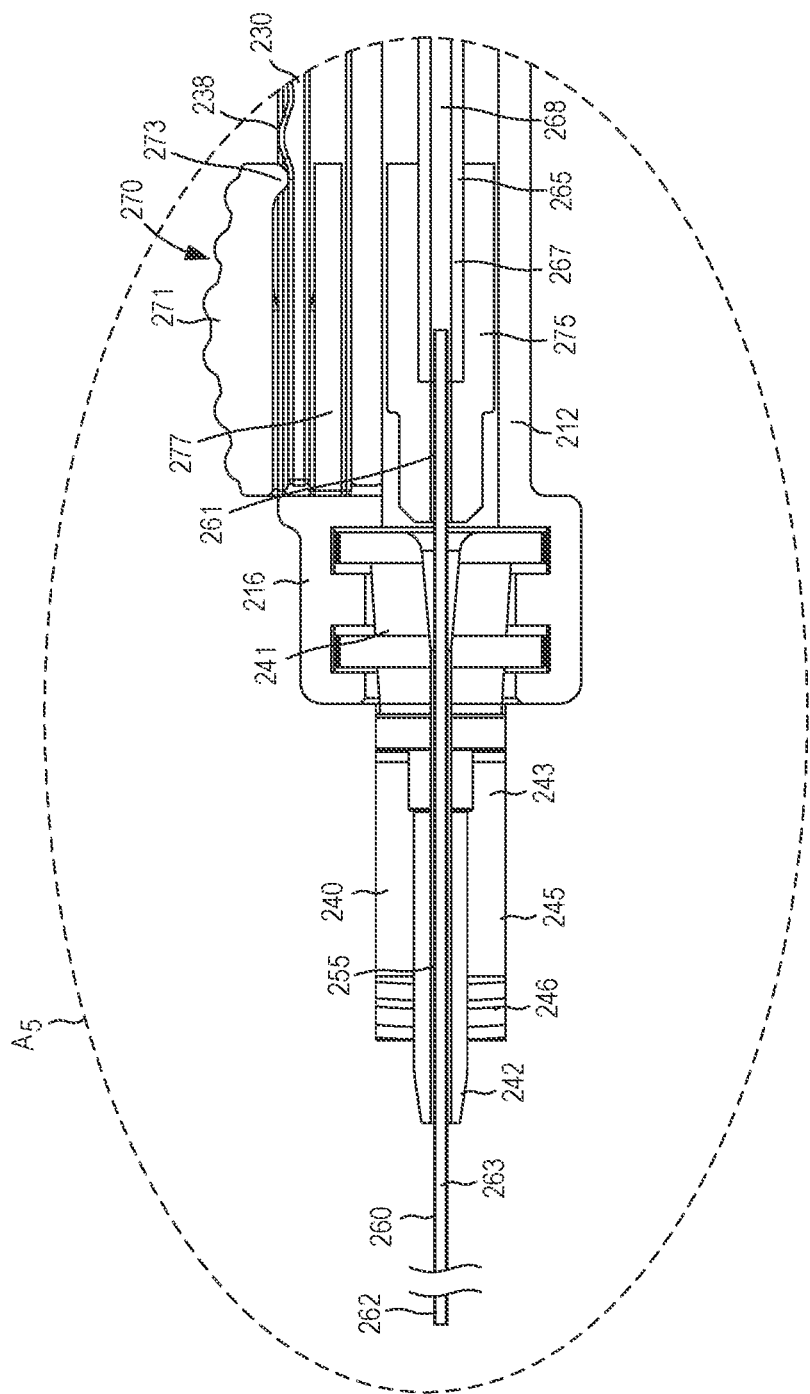
FIG. 29 is an enlarged cross-sectional view of a portion of the fluid transfer device identified by the region A5 in FIG. 28.

As shown in FIGS. 27-29, in some instances, the catheter 260 can be in the second position when the actuator 270 is in a distal most position. In this manner, the distal surface of the catheter 260 is positioned within the vein at a predetermined distance beyond the distal surface of the catheter 260. In some instances, placing the distal surface of the catheter 260 the predetermined and/or desired distance from the distal surface of the PIV can, for example, place the distal surface of the catheter 260 in a position within a vein that is substantially free from debris (e.g., fibrin/blood clots) otherwise surrounding the distal end portion of the PIV.

In some instances, the indwelling PIV can substantially occlude at least a portion of the vein within which the PIV is disposed. As such, PIVs are often suited for delivering a fluid rather than aspirating blood. The venous system, however, is a capacitance system and thus, reroutes blood flow through a different vein (e.g., forms a bypass around the occlusion or substantial occlusion). Moreover, the alternate venous structure typically rejoins the vein in which the PIV is disposed at a given distance downstream of the PIV and thus, delivers at least portion of the flow of blood that would otherwise be flowing through the vein in which the PIV is disposed. Similarly, veins typically have many branch vessels coupled to thereto that similarly deliver a flow of blood to the vein within which the PIV is disposed.

As such, in some instances, the predetermined and/or desired distance between the distal surface of the catheter 260 and the distal surface of the PIV can be sufficient to place the distal surface of the catheter 260 downstream of one or more branch vessels in fluid communication with the vein within which the PIV is disposed. In other words, the distal surface of the catheter 260 can extend beyond the distal surface of the catheter 260 such that at least one branch vessel is disposed between the distal surface of the catheter 260 and the distal surface of the PIV when the catheter 260 is in the second position. Therefore, with the lumen 263 of the catheter 260 extending through the proximal end portion 261 and the distal end portion 262 of the catheter 260, placing the distal surface of the catheter 260 the predetermined and/or desired distance from the distal surface of the PIV places the lumen 263 of the catheter 260 in fluid communication with a portion of the vein receiving a substantially unobstructed or unrestricted flow of blood (e.g., unobstructed by the PIV and/or debris associated with the indwelling of the PIV).

In some instances, for example, the predetermined and/or desired distance can be between about 0.0 millimeters (e.g., the distal surfaces are flush) and about 100 millimeters (mm). In other embodiments, the predetermined and/or desired distance can be between about 10 mm and about 90 mm, between about 20 mm and about 80 mm, between about 30 mm and about 70 mm, between about 30 mm and about 60 mm, between about 40 mm and about 50 mm, or between any other suitable range or subranges therebetween. In some embodiments, for example, the transfer device 200 can be configured such that the actuator 270 can move about 95 mm along the introducer 210 (e.g., the transfer device 200 has a 95 mm stroke) to position the distal surface of the catheter 260 at about 40 mm beyond the distal surface of the PIV to which the transfer device 200 is coupled. In other embodiments, for example, the transfer device 200 can have a 47 mm stroke that positions the distal surface of the catheter 260 at about 20 mm beyond the distal surface of the PIV to which the transfer device 200 is coupled. In still other embodiments, the transfer device 200 can have any suitable stroke length to position the distal surface of the catheter 260 at the predetermined and/or desired distance from the distal surface of the PIV.

Although the predetermined and/or desired distance is described above as being a positive distance, that is, the distal surface of the catheter 260 is distal to the distal surface of the PIV, in other embodiments, the predetermined and/or desired distance can be associated with the distal surface of the catheter 260 being in a proximal position relative to the distal surface of the PIV (e.g., a negative distance). For example, in some instances, the predetermined and/or desired distance can be between about 0.0 mm (e.g., the distal surfaces are flush) to about −50 mm, between about −10 mm and about −40 mm, between about −20 mm and about −30 mm, or between any other suitable range or subranges therebetween. In some instances, the predetermined and/or desired distance can be less than −50 mm (e.g., the distal surface of the catheter 260 is more than 50 mm proximal to the distal surface of the PIV). In some instances, the catheter 260 can be placed in the second position such that the distal end portion 262 of the catheter 260 remains within the PIV in a position distal to, for example, a kink or the like. For example, in some instances, indwelling PIVs can have one or more portions that are kinked such as a portion of the PIV where the peripheral intravenous catheter couples to a hub. In such instances, the predetermined and/or desired distance can be such that the distal surface of the catheter 260 is distal to the portion of the PIV that forms the kink (e.g., where the peripheral intravenous catheter couples to the hub). In some such instances, placing the distal surface of the catheter 260 distal to the kinked portion of the PIV but remaining within the PIV can result in a fluid flow path being sufficiently unrestricted to allow blood to be aspirated through the catheter 260.

With the catheter 260 in the second position (e.g., with the transfer device 200 in the second configuration shown, for example, in FIGS. 25 and 26 or FIGS. 27-29), the user can establish fluid communication between a fluid reservoir, fluid source, syringe, and/or the like and the catheter 260. For example, as described above, in some embodiments, the user can physically and fluidically couple the coupler 269 of the secondary catheter 265 to a fluid reservoir, fluid source, syringe, and/or the like. Although described as establishing fluid communication between the catheter 260 and the fluid reservoir or fluid source after placing the catheter 260 in the second position, in other embodiments, the user can establish fluid communication between the catheter 260 and the fluid reservoir or fluid source prior to moving the actuator 270 relative to the introducer 210. With the catheter 260 in fluid communication with the fluid reservoir and/or fluid source, the transfer device 200 can then transfer a fluid from the patient or transfer a fluid to the patient via the catheter 260 extending through and beyond the PIV. For example, in some instances, the user can physically and fluidically couple the transfer device 200 to a fluid reservoir, evacuated container, syringe, and/or the like and then can aspirate a volume of blood from the vein based at least in part on disposing the distal surface of the catheter 260 at the predetermined and/or desired distance beyond the distal surface of the PIV.

In other instances, the user can physically and fluidically coupled the transfer device 200 to a fluid source or the like and then can deliver a volume of fluid from the fluid source to a portion of the vein at a position downstream of the PIV that receives a substantially uninhibited and/or unrestricted flow of blood. In some instances, disposing the distal surface of the catheter 260 at the predetermined and/or desired distance beyond the distal surface of the PIV, for example, can reduce potential harm associated with infusion of caustic drugs. For example, by positioning the distal surface of the catheter 260 within a portion of the vein receiving a flow of blood that would otherwise be inhibited and/or restricted by the indwelling PIV, the caustic drug can be entrained in the flow of blood and delivered to the target location. As such, a volume of the caustic drug is not retained within the debris or otherwise disposed in a position within the vein receiving little blood flow.

In some instances, once a desired amount of blood has been collected and/or once a desired volume of a drug has been delivered to the patient, the user can move the actuator 270 in the proximal direction, thereby placing the transfer device 200 in a third (used) configuration. In the third configuration, the catheter 260 can be disposed within the introducer 210 (e.g., distal to the seal or the like) and isolated therein. For example, in some embodiments, the actuator 270 can be placed in it proximal most position, in which the catheter 260 is in the first position. Moreover, once the actuator 270 and catheter 260 are in the desired position, the user can, for example, manipulate the secondary catheter 265 within the opening 217 such that a surface of the introducer 210 that defines the smaller portion of the opening 217 contacts and clamps the secondary catheter 265. As such, the lumen 268 of the secondary catheter 265 can be substantially obstructed, occluded, blocked, pinched, etc. to limit and/or substantially prevent a flow of fluid therethrough. In some instances, clamping the secondary catheter 265 as described, for example, can reduce and/or substantially prevent fluid from leaking through the secondary catheter 265. In some instances, the transfer device 200 can then be decoupled from the fluid reservoir, fluid source, syringe, etc. and safely discarded.

FIG. 30 is a flowchart illustrating a method 10 of using a fluid transfer device to transfer a fluid through a peripheral intravenous line, according to an embodiment. The method includes coupling a lock of the fluid transfer device to an indwelling peripheral intravenous line (PIV), at 11. The fluid transfer device can be any suitable device configured for fluid transfer through a PIV. For example, in this embodiment, the fluid transfer device can be substantially similar to the fluid transfer device 200 described above with reference to FIGS. 3-29. As such, the fluid transfer device includes an introducer coupled to the lock, a catheter movably disposed in the introducer, and an actuator coupled to the catheter and in contact with an outer surface of the introducer. In some embodiments, the introducer includes a first member and a second member that collectively form the introducer. In such embodiments, the second member can have an outer surface that defines a set of ribs or the like, as described above with reference to the second member 230 in FIGS. 7-12. In this manner, the actuator can be in contact with the ribs formed by the second member of the introducer. Moreover, as described above with reference to the transfer device 200, the introducer can define an inner volume having a tortuous cross-sectional shape configured to at least partially isolate the catheter disposed in the inner volume from a volume outside of the introducer.

With the lock coupled to the PIV (and/or an adapter coupled to the PIV), the actuator is moved relative to the introducer to advance the catheter from a first position, in which the catheter is disposed within at least one of an inner volume defined by the introducer or the lock, toward a second position, in which at least a portion of the catheter is disposed beyond at least a portion of the PIV, at 12. In this manner, the catheter can be advanced, for example, in the distal direction. In some embodiments, the lock can include an inner surface that defines a lumen configured to receive the catheter as the catheter is moved toward the second position. In some embodiments, the inner surface of the lock can contact, support, and/or otherwise guide the catheter as the catheter is moved in the distal direction toward the second position.

As described above with reference to the transfer device 200 in some embodiments, the arrangement of the actuator and the introducer is such that advancing the actuator relative to the introducer advances a portion of the actuator along the ribs formed by the outer surface of the introducer. In some embodiments, moving the actuator along the ribs can produce a vibration of the actuator, which in turn, can produce, for example, a haptic, tactile, and/or audible output. Thus, an indication associated with a position of a distal end portion of the catheter as the actuator moves the catheter from the first position toward the second position is provided to the user, at 13. For example, in some embodiments, the actuator and the set of ribs can collectively produce a "click" sound, a haptic vibration, and/or the like. In some embodiments, the introducer can include indicia or the like that can indicate to the user the relative position of the distal end portion of the catheter. In other embodiments, the amount of times the actuator has vibrated due to being moved along the ribs can be associated with and/or otherwise provide an indication of the relative position of the distal end portion of the catheter Based at least in part on the indication, the catheter is placed in the second position such that the distal end portion of the catheter is disposed at a predetermined and/or desired distance beyond at least a portion of the PIV (e.g., beyond a distal surface of the PIV), at 14. For example, the catheter can be placed in the second position after moving the actuator at least a portion of the length of the introducer. In some embodiments, the catheter can be disposed in the second position when the actuator is placed in a distal most position. As described above with reference to the transfer device 200, in some instances, the predetermined and/or desired distance beyond the portion of the PIV can position a distal surface of the catheter within a portion of the vein that is substantially free from debris (e.g., fibrin/blood clots) otherwise surrounding a distal end portion of the PIV. Similarly, in some instances, disposing the distal end portion of the catheter at the predetermined and/or desired distance from, for example, the distal end portion of the PIV can place the lumen of the catheter in fluid communication with a portion of the vein receiving a substantially unobstructed or unrestricted flow of blood (e.g., unobstructed by the PIV and/or debris associated with the indwelling of the PIV), as described in detail above. In this manner, a user can couple the transfer device to a fluid reservoir and/or fluid source to transfer fluid from and/or to, respectively, the patient.

FIGS. 31-34 illustrate a fluid transfer device 300 according to an embodiment. The fluid transfer device 300 can be any suitable shape, size, and/or configuration. In some embodiments, the fluid transfer device 300 (also referred to as "transfer device") can be similar to and/or substantially the same as the transfer device 200 described in detail above with reference to FIGS. 3-30. Accordingly, portions and/or aspects of the transfer device 300 are not described in further detail herein and should be considered substantially similar in form and/or function to corresponding portions and/or aspects of the transfer device 200 unless otherwise explicitly described.

As shown in FIG. 31, the transfer device 300 includes an introducer 310, a catheter 360, and an actuator 370. The introducer 310 includes a proximal end portion 311 and a distal end portion 312 and defines an inner volume 313. The distal end portion 312 of the introducer 310 includes and/or is coupled to a lock 340 configured to couple the introducer 310 to a placed and/or indwelling PIV (not shown). As described above with reference to the introducer 210, the introducer 310 has an outer surf ace that includes and/or forms a set of ribs 336 arranged along a length of the introducer 310. The ribs 336 are configured to engage and/or contact a portion of the actuator 370, as described in further detail herein. In this manner, the introducer 310 can be similar to and/or substantially the same as the introducer 210 described in detail above with reference to, for example. FIGS. 3-12.

The catheter 360 is coupled to the actuator 370 and is movably disposed within the introducer 310. In addition, at least a portion of the catheter 360 can be movably disposed in a lumen defined by the lock 340. The catheter 360 can be any suitable shape, size, and/or configuration. For example, in some embodiments, the catheter 360 can be substantially similar to the catheter 260 described in detail above. Accordingly, the catheter 360 is not described in further detail herein.

The actuator 370 can be any suitable shape, size, and/or configuration. As shown in FIGS. 31 and 32, the actuator 370 includes a first portion 371 and a second portion 375, and a wall 377 disposed therebetween. The first portion 371 of the actuator 370 is configured to movably couple to the introducer 310. The second portion 375 of the actuator 370 is configured to couple to a proximal end portion of the catheter 360 and a distal end portion of a secondary catheter 365 (FIG. 31). The arrangement of the catheter 360, the secondary catheter 365, and the actuator 370 is such that a lumen of the catheter 360 is in fluid communication with a lumen of the secondary catheter 365 to allow fluid to flow therebetween, as described above with reference to the arrangement of the catheter 260, the secondary catheter 265, and the actuator 270.

The first portion 371 of the actuator 370 includes a tab 373 that extends from an inner surface of the first portion 371 to contact an outer surface of the introducer 310. For example, the tab 373 can be a protrusion, bump, ridge, knob, etc. configured to contact the set of ribs 336 formed along the outer surface of the introducer 310. In the embodiment shown in FIGS. 31-34, the actuator 370 is disposed at an angle relative to the introducer 310 as a result of the tab 373 contacting the set of ribs 336. That is to say, the contact between the tab 373 extending from the inner surface of the first portion 371 and the set of ribs 336 tilts, pivots, angles, and/or otherwise displaces at least a portion of the actuator 370 such that a longitudinal axis L1 of the actuator 370 is non-parallel to a longitudinal axis L2 of the introducer 310, as shown in FIG. 32. In this manner, a first force F1 is exerted on a proximal end portion of the actuator 370 in a first direction and a second force F2 is exerted on a distal end portion of the actuator 370 in a second direction (e.g., an equal and opposite force). Thus, with the second portion 375 of the actuator 370 coupled to the proximal end portion of the catheter 360 and with a portion of the catheter 360 (e.g., at least a distal end portion of the catheter 360) disposed in the lumen of the lock 340, the angled arrangement and/or orientation of the actuator 370 results in a stress being applied along a length of the catheter 360 disposed between the actuator 370 and the lock 340. As shown in FIG. 31, the stress applied along the length of the catheter 360 can be sufficient to bow, bend, deflect, deform, clutch, and/or otherwise reconfigure at least a portion of the catheter 360 disposed between the actuator 370 and the lock 340. In other words, angling or tilting the actuator 370 results in a preloading of the catheter 360 (e.g., preloaded stress).

Figure 33:
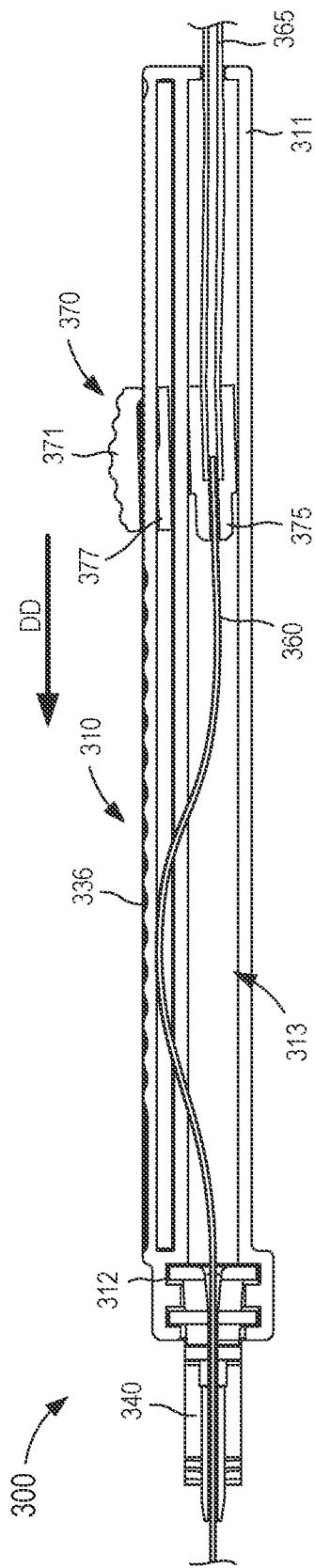
FIG. 33 is a cross-sectional side view of the fluid transfer device of FIG. 31 in a second configuration.
Figure 34:
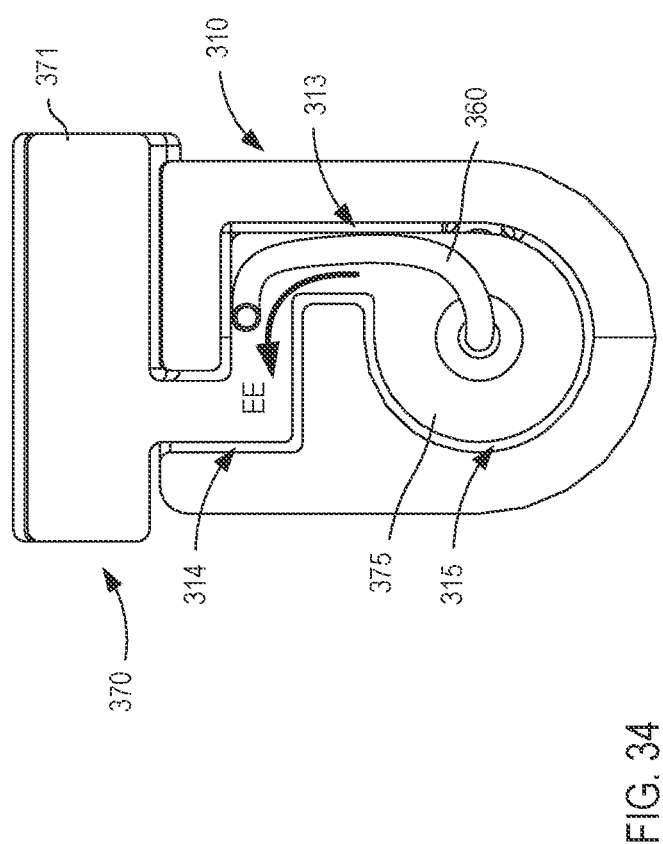
FIG. 34 is a cross-sectional front view of the fluid transfer device of FIG. 31 in the second configuration.

As described in detail above with reference to the device 200, the actuator 370 can be moved along and/or relative to the introducer 310 to move the catheter 360 between a first position (e.g., a proximal position) and a second position (e.g., a distal position). In some instances, the arrangement of the actuator 370 and the catheter 360 can result in a "clutching" of the device 300 as the actuator 370 is advanced along the introducer 310. For example, a user can exert a force on the first portion 371 of the actuator to move the actuator 370 in a distal direction relative to the introducer 310, which in turn, moves the catheter 360 toward its second position (e.g., the distal position), as indicated by the arrow DD in FIG. 33. In some instances, however, the catheter 360 (e.g., the distal end of the catheter 360) may encounter or impact an obstruction or the like that hinders or prevents further distal movement of the catheter 360. In such instances, the preloading of the catheter 360 resulting from the angling of the actuator 370 (described above) produces a stress concentration riser or the like along the length of the catheter 360 disposed between the actuator 370 and the lock 340. Thus, with the distal end of the catheter 360 in contact with the obstruction, the force exerted by the user on the first portion 371 of the actuator 370 (e.g., in the DD direction) results in a "clutching" (e.g., deflection, deformation, bending, bowing, etc.) of the catheter 360. For example, in some embodiments, a portion of the catheter 360 can bend, deform, deflect, and/or move through a portion of the inner volume 313 (e.g., a portion of the inner volume 313 receiving, for example, the wall 377 of the actuator 370) to a "clutched" configuration, as shown in FIGS. 33 and 34.

In some instances, the clutching of the catheter 360 can provide the user with an indication that the movement of the catheter 360 is obstructed and/or otherwise hindered. For example, in some embodiments, the introducer 310 can be formed of a substantially clear and/or transparent material that can allow a user to visualize a status and/or configuration of the catheter 360. In some embodiments, the clutching and/or deformation of the catheter 360 can be such that a portion of the catheter 360 impacts an inner surface of the introducer 310, which in turn, can produce an audible (e.g., a "click") and/or haptic indication that the catheter 360 is in the clutched configuration (e.g., that the movement of the catheter 360 is hindered or blocked).

In some instances, the clutching of the catheter 360 can provide and/or can form a self-relief mechanism or the like that can facilitate the advancement of the catheter 360 beyond an obstruction. For example, in some instances, after the catheter 360 is clutched (i.e., deformed as shown in FIGS. 33 and 34), the user can reduce and/or remove the force exerted on the actuator 370 (e.g., in the DD direction), which in turn, can allow the catheter 360 to at least partially reconfigure. In some such instances, the distal end portion of the catheter 360 can move beyond and/or through the obstruction or the like as the catheter 360 reconfigures. For example, in some instances, the distal end of the catheter 360 can contact and/or impact a wall (e.g., a kinked wall) or structure of a PIV. PIV hub, extension set, and/or the like as the catheter 360 is advanced in the distal direction therethrough. This contact and/or impact, in turn, can result in a clutching of the catheter 360 (as described above). In such instances, reducing and/or removing the force exerted on the first portion 371 of the actuator 370 allows the catheter 360 to reconfigure and/or transition toward an unclutched configuration wherein the distal end portion of the catheter 360 moves beyond the obstructing wall and/or structure in a safe, controlled, and/or predetermined manner. As such, the clutching of the catheter 360 can provide a self-correcting mechanism or the like allowing the catheter 360 to "unclutch" in response to a reduction of the force, which in turn allows the distal end of the catheter 360 to move along and/or beyond an obstruction.

In other instances, the catheter 360 may remain in a clutched configuration when the force exerted on the actuator 370 is reduced and/or removed. In such instances, the user can, for example, manipulate at least one of the device 300 and/or a portion of the patient to "unclutch" the catheter 360. For example, in some instances, the catheter 360 can be inserted through an indwelling PIV and into a vein of a patient's arm. In some such instances, the distal end of the catheter 360 can impact a kink or the like in the indwelling PIV catheter (e.g., often at or near the PIV catheter's insertion site), which in turn, can transition the catheter 360 to the clutched configuration, as described above. Moreover, in some instances, the catheter 360 may remain in the clutched configuration despite reducing and/or removing the force exerted on the actuator 370. As such, the user can, for example, manipulate the arm of the patient and/or can manipulate the device 300 (coupled to the PIV) relative to the arm of the patient to move and/or reconfigure the PIV relative to the vein in which the PIV and the catheter 360 are disposed. In some instances, after manipulating the arm of the patient and/or otherwise reconfiguring the device 300 and/or PIV relative to the vein, the catheter 360 can transition to the unclutched configuration.

In some embodiments, the clutching of the catheter 360 and/or device 300 can be operative in limiting a force associated with impacting an obstruction. For example, in some instances, the catheter 360 can be advanced through at least a portion of an indwelling peripheral intravenous line (PIV) toward a vein. As the catheter 360 is advanced into and/or through the PIV, it may be desirable to reduce or limit a force associated with the distal end of the catheter 360 impacting an internal structure of the PIV or the like. As such, the clutching of the catheter 360 in response to the distal end of the catheter 360 impacting the internal structure of the PIV (and/or any other structure such as an internal structure of an extension set, a vein wall or other venous structure, etc.) can act to limit force exerted thereon. That is to say, the clutching of the catheter 360 absorbs, redirects, and/or otherwise redistributes at least a portion of the force otherwise associated with the distal end of the catheter 360 impacting the structure. Thus, the clutching of the catheter 360 can reduce and/or substantially prevent damage to the catheter 360, the structure of the PIV or extension set, a vein wall, and/or the like, which may otherwise result from an impact with the distal end of the catheter 360.

In some embodiments, the catheter 360 disposed within the introducer 310 can be configured to clutch, bend, flex, bow, and/or otherwise reconfigure in a predetermined and/or predictable manner, which can allow for a "tuning" or control of one or more parameters, characteristics, dynamics, etc. of the device 300. For example, in some embodiments, the catheter 360 can be biased when in a first configuration (e.g., a proximal or unclutched configuration). In this configuration, the amount of bias can be increased or decreased by increasing or decreasing, respectively, an angle of the actuator 370 relative to the introducer 310 (as described above). The increase or decrease in the amount of bias can result in an increase or decrease, respectively, in an amount of preloaded stress and/or force along a portion of the catheter 360, which in turn, can increase or decrease, respectively, a likelihood or ease for the catheter 360 to transition from the unclutched configuration to the clutched configuration.

In some instances, the manner in which the catheter 360 is clutched can be controlled and/or "tuned". For example, as described above, the catheter 360 can be in a biased or bowed configuration when unclutched. In response to impacting an obstruction, the catheter 360 can transition from the unclutched configuration to the clutched configuration such that the catheter 360 deflects in a sinusoidal manner (e.g., curvilinear, substantially S-shaped, etc.), as shown in FIG. 33. In some instances, further force exerted on the actuator 370 can result in a bending or deflecting of the catheter such that a portion of the catheter moves through the second portion 315 of the inner volume 313 of the introducer 310 (e.g., a vertical portion or the like) and into the first portion 314 of the inner volume 313 of the introducer (e.g., a horizontal portion or the like), as indicated by the arrow EE in FIG. 34. Moreover, in some embodiments, a portion of the catheter 360 can deflect, bend, and/or clutch such that the portion of the catheter 360 extends through the first portion 314 of the inner volume 313 to be disposed outside of the introducer 310. Thus, in some embodiments, the catheter 360 can have and/or can experience a four-stage deflection when transitioned from the unclutched configuration to the clutched configuration. In other embodiments, the range of motion of the catheter 360 when moved to the clutched configured can be limited such that the catheter 360 remains in the second portion 315 of the inner volume 313 or the first portion 314 of the inner volume 313 (e.g., the catheter 360 can be moved through a two-stage deflection or a three-stage deflection, respectively). As such, the catheter 360 and/or device 300 can be configured to clutch in a predetermined, desired, and/or predictable manner, which in turn, can change, adjust, tune, and/or otherwise control one or more characteristics associated with the insertion of the catheter 360 through the indwelling PIV and into a vein.

As described above with reference to the device 200, advancing the actuator 370 relative to the introducer 310 results in the tab 373 of the first portion 371 of the actuator 370 being moved along the set of ribs 336. In some instances, the movement of the tab 373 along the set of ribs 336 can provide a user with haptic feedback or the like associated with moving the catheter 360 between the first and second position. In addition, in some instances, vibration of the actuator 370 resulting from the tab 373 being moved along the set of ribs 336 can likewise result in a vibration of the catheter 360. In some instances, the vibration of the catheter 360 while at least partially disposed in a vein can result in a vasodilation or vasorelaxation of the vein, which in turn, can increase a diameter of the vein. The increase in the diameter of the vein and/or a reduction in an amount of constriction of the vein can, for example, allow for increased access to portions of the vein and/or increased blood flow through the vein, which in turn, can result in better fluid (e.g., blood) transfer from the vein via the catheter 360 at least partially disposed therein.

FIGS. 35 and 36 are schematic illustrations of a fluid transfer device 400 according to an embodiment. The fluid transfer device 400 can be any suitable transfer device such as those described herein. For example, the fluid transfer device 400 can be substantially the same in form and/or function as the fluid transfer device 200 described above with reference to FIGS. 3-29. Thus, while relevant portions of the fluid transfer device 400 are identified in FIGS. 35 and 36, the fluid transfer device 400 is not limited thereto and should be considered substantially the same as the fluid transfer device 200 unless otherwise explicitly indicated. For example, the fluid transfer device 400 (also referred to herein as "transfer device" or "device") includes an introducer 410 having a proximal end portion 411 and a distal end portion 412. As described above with reference to the transfer device 200, the device 400 also includes a catheter movably disposed within the introducer and an actuator movably coupled to the introducer and fixedly coupled to the catheter. As described above, a user can exert a force on the actuator to move the actuator along the introducer 410, which in turn, moves the catheter between a first position, in which the catheter is disposed in the introducer 410, and a second position, in which at least a portion of the catheter extends distally beyond the introducer 410.

As shown in FIGS. 35 and 36, the distal end portion 412 of the introducer 410 is coupled to a lock 440 configured to couple the device 400 to, for example, an extension set 490 (e.g., an adapter such as a T-adapter or Y-adapter) and/or a peripheral intravenous line (PIV) 405. The lock 440 can be substantially similar to the lock 240 described above with reference to, for example. FIGS. 13-15. Thus, aspects of the lock 440 are described in further detail herein.

The lock 440 includes a proboscis 442, a first arm 443, and a second arm 450. As shown in FIG. 36, the first arm 443 and the second arm 450 can collectively engage a proximal end portion 491 of the extension set 490 to couple the device 400 thereto. Moreover, the proboscis 442 can be at least partially disposed within the extension set 490 when the lock 440 is coupled thereto to place the lock 440 in fluid communication with the PIV 405 coupled to a distal end portion 492 of the extension set 490. While shown and described as being coupled to the extension set 490, in other embodiments, the first arm 443 and the second arm 450 can collectively engage a portion of the PIV 405 to couple the device 400 thereto (e.g., without the use of the extension set 490).

As shown in FIG. 36, the arrangement of the first arm 443 and the second arm 450 can be such that when coupled to the extension set 490 and/or the PIV 405 and when the first arm 443 or the second arm 450 is placed in contact with a target surface S, the device 400 is disposed at a predetermined and/or desired angle θ. Expanding further, in some embodiments, the target surface S can be an arm of a patient and the PIV 405 can be previously inserted therethrough to be at least partially disposed within a vein of the patient's arm (e.g., the PIV 405 is an indwelling PIV or the like). The lock 440 is rotatably coupled to the distal end portion 412 of the introducer 410, thereby allowing the user to rotate the lock 440 to a desired orientation such that the first arm 443 or the second arm 450 is adjacent to the target surface S. In the example shown in FIG. 36, the second arm 450 is adjacent to, and in contact with, the target surface S. With the lock 440 coupled to the extension 490 and with the extension set 490 coupled to the indwelling PIV 405, the second arm 450 can be in contact with the target surface S such that the device 400 is disposed at the predetermined and/or desired angle θ relative to the target surface S, as shown in FIG. 36.

In some embodiments, the predetermined and/or desired angle θ can be between about 0° and about 30°. For example, in some embodiments, the predetermined and/or desired angle θ can be about 15°. In such embodiments, disposing the device 400 at the predetermined and/or desired angle θ can, for example, facilitate the advancement of the catheter from its first position to its second position such that at least a distal end portion of the catheter extends through the PIV 405 to be disposed within the vein. In some instances, the predetermined and/or desired angle θ of the device 400 can be approximately equal to and/or otherwise associated with an angle of insertion of the PIV 405. Thus, disposing the device 400 at the predetermined and/or desired angle θ can limit and/or reduce a likelihood of kinks along the catheter, which in turn, can facilitate a transfer of bodily fluid (e.g., blood) therethrough). In addition, in some instances, disposing the device 400 at the predetermined and/or desired angle θ can result in less movement of the device 400 and/or PIV, less likelihood of disconnection and/or dislodgment, a reduced risk of hematomas, thrombosis, clots, infections, etc., and/or can increase patient comfort.

Figure 37:
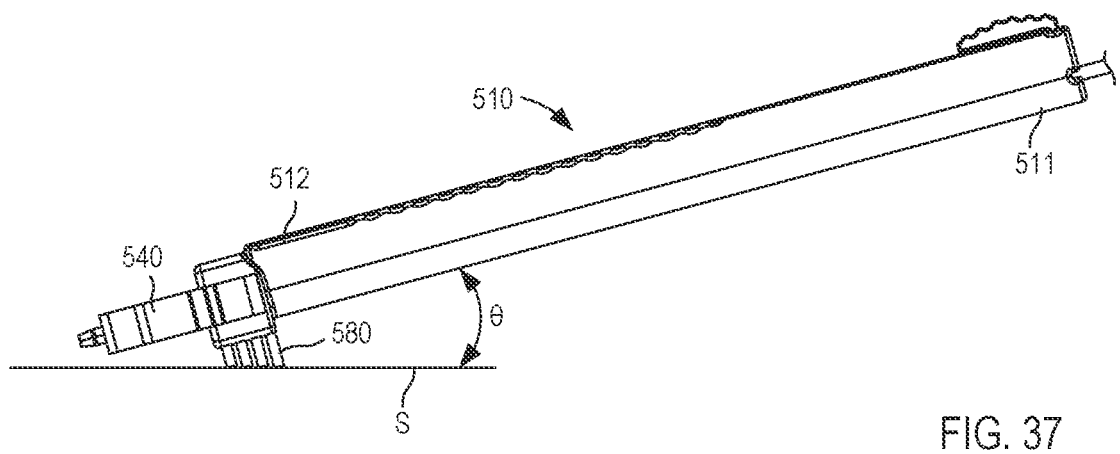
FIGS. 37 and 38 are side views of a fluid transfer device and a support member each according to a different embodiment.

While second arm 450 of the lock 440 is described above as being placed in contact with the target surface S to dispose and/or maintain the transfer device 400 at the predetermine and/or desired angle θ relative to the target surface S, in other embodiments, a fluid transfer device can include and/or can be coupled to any suitable device configured to dispose the transfer device at a predetermined and/or desired angle. For example, FIG. 37 illustrates a fluid transfer device 500 according to an embodiment. The fluid transfer device 500 can be substantially the same in form and/or function as the fluid transfer device 400 described above with reference FIGS. 35 and 36 and, as such, portions of the transfer device are not described in further detail herein.

The fluid transfer device 500 (also referred to herein as "transfer device" or "device") includes an introducer 510 having a proximal end portion 511 and a distal end portion 512. The distal end portion 512 of the introducer 510 is coupled to a lock 540, which in turn, is configured to physically and fluidically couple the device 500 to an indwelling PIV (not shown in FIG. 37), as described in detail above. In the embodiment shown in FIG. 37, the distal end portion 512 of the introducer 510 is coupled to a support member 580. The support member 580 can be any suitable shape, size, or configuration. For example, in this embodiment, the support member 580 can be one or more extensions, posts, protrusions, rods, fingers, and/or the like, each of which are coupled to and/or included in the distal end portion 512 of the introducer 510. As described above with reference to the second arm 450 of the lock 440, the support member 580 can be in contact with a target surface S and can be arranged such that when the support member 580 is coupled to the distal end portion 512 of the introducer 510, the device 500 is maintained and/or disposed at a predetermined and/or desired angle θ relative to the target surface S.

Figure 38:
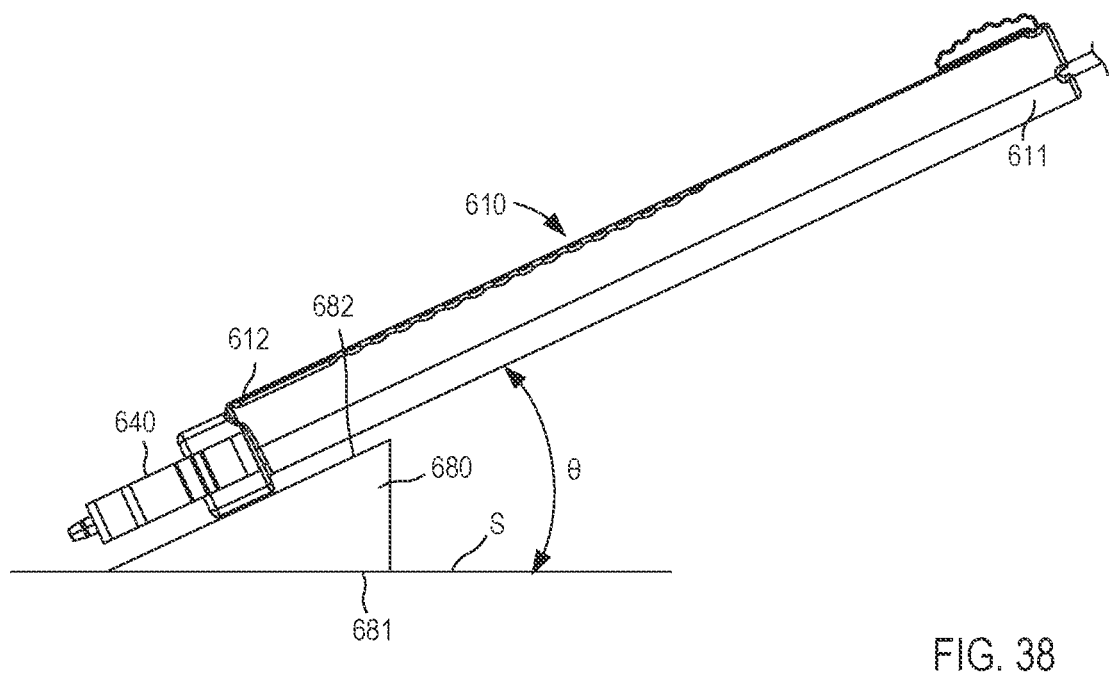

While the support member 580 is particularly shown in FIG. 37, it should be understood that a fluid transfer device can include and/or can be coupled to a support member having any suitable shape, size, and/or configuration. For example. FIG. 38 illustrates a fluid transfer device 600 according to an embodiment. The fluid transfer device 600 can be substantially the same in form and/or function as the fluid transfer device 500 described above with reference FIG. 37 and, as such, portions of the transfer device 600 are not described in further detail herein.

The fluid transfer device 600 (also referred to herein as "transfer device" or "device") includes an introducer 610 having a proximal end portion 611 and a distal end portion 612. The distal end portion 612 of the introducer 610 is coupled to a lock 640, which in turn, is configured to physically and fluidically couple the device 600 to an indwelling PIV (not shown in FIG. 38), as described in detail above. In the embodiment shown in FIG. 38, the distal end portion 612 of the introducer 610 is coupled to a support member 680 configured as a wedge or the like. For example, in some embodiments, the support member 680 can include a first surface 681 configured to be placed in contact with a target surface S and a second surface 682 configured to form an angle relative to the first surface 681. In this manner, the second surface 682 can be placed in contact with a portion of the device 600 (e.g., the distal end portion 612 of the introducer 610 and/or any other suitable portion of the device 600) to dispose and/or maintain the device 600 at a predetermined and/or desired angle θ relative to the target surface S.

Figure 39:
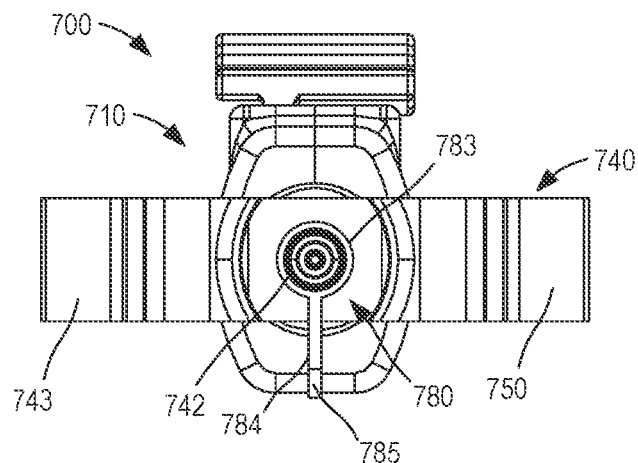
FIG. 39 is a front view of a fluid transfer device and a support member according to an embodiment.
Figure 40:
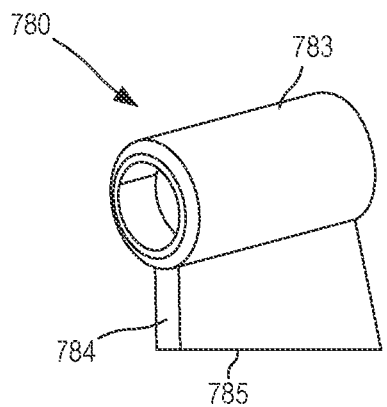
FIG. 40 is a perspective view of the support member of FIG. 39.

While the support members 580 and 680 are described above as being included in and/or coupled to the introducers 510 and 610, respectively, in other embodiments, a support member can be included in and/or coupled to any suitable portion of a fluid transfer device. For example, FIGS. 39 and 40 illustrate a fluid transfer device 700 according to an embodiment. The fluid transfer device 700 can be substantially the same in form and/or function as the fluid transfer device 400 described above with reference to FIGS. 35 and 36 and, as such, portions of the transfer device 700 are not described in further detail herein.

The fluid transfer device 700 (also referred to herein as "transfer device" or "device") includes an introducer 710 having a distal end portion that is coupled to a lock 740 (as described above). The lock 740 includes a proboscis 742, a first arm 743, and a second arm 750. In the embodiment shown in FIGS. 39 and 40, the transfer device 700 includes a support member 780 coupled to the lock 740. More specifically, the support member 780 includes a first portion 783 and a second portion 784. The first portion 783 of the support member 780 can be substantially annular and/or can otherwise define an opening configured to receive, for example, at least a portion of the proboscis 742 of the lock 740. In other words, the proboscis 742 of the lock 740 can be inserted into the first portion 783 of the support member 780, thereby coupling the support member 780 to the lock 740. In some embodiment, the first portion 783 of the support member 780 and a portion of the proboscis 742 can collective form a friction or press fit that can at least temporarily retain the support member 780 in substantially fixed position relative to the lock 740.

As shown in FIG. 40, the second portion 784 of the support member 780 extends from the first portion 783 and includes a contact surface 785. The first portion 783 is disposed at a predetermined and/or desired angle relative to the contact surface 785 of the second portion 784. Said another way, an axis defined by the opening of the first portion 783 is disposed at the predetermined and/or desired angle relative to a plane defined by and/or parallel to the contact surface 785. Accordingly, when the support member 780 is coupled to the lock 740 and the contact surface 785 is placed in contact with a target surface (e.g., a portion of the patient's anatomy), the device 700 can be disposed and/or placed at the predetermined and/or desired angle relative to the target surface. As described above, the predetermined and/or desired angle can be between about 0° and about 30°. For example, in some embodiments, the predetermined and/or desired angle can be about 15°. In other embodiments, the predetermined and/or desired angle can be about 25°. In still other embodiment, the predetermined and/or desired angle can be less than 0° or greater than 30°.

Figure 41:
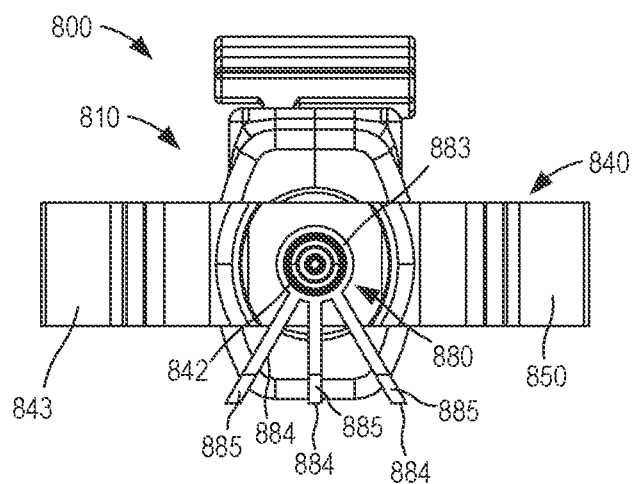
FIG. 41 is a front view of a fluid transfer device and a support member according to an embodiment.

While the support member 780 is described above as including a single member (i.e., the second portion 784) extending from the first portion 783, in other embodiments, a support member can include any number of extensions (e.g., second portions). For example, FIG. 41 illustrates a fluid transfer device 800 according to an embodiment. The fluid transfer device 800 can be substantially the same in form and/or function as the fluid transfer device 700 described above with reference to FIGS. 39 and 40 and, as such, portions of the transfer device 700 are not described in further detail herein.

The fluid transfer device 800 (also referred to herein as "transfer device" or "device") includes an introducer 810 having a distal end portion that is coupled to a lock 840 (as described above). The lock 840 includes a proboscis 842, a first arm 843, and a second arm 850. In the embodiment shown in FIG. 41, the transfer device 800 includes a support member 880 coupled to the lock 840. As described above with reference to the support member 780, the support member 880 includes a first portion 883 and a set of second portions 884 extending from the first portion 883. The first portion 883 is configured to be disposed about a portion of the proboscis 842, as described above with reference to the support member 780. Furthermore, each second portion 884 includes a contact surface 885, as described above with reference to the support member 780.

The support member 880 can differ from the support member 780, however, in the arrangement of the second portion(s) 884. For example, as shown in FIG. 41, the support member 880 includes a set of three second portions 884 distributed about a portion of the circumference of the first portion 883. In this manner, the set of second portions 884 can be placed in contact with a target surface (e.g., a portion of the patient's anatomy) and the device 800 can be disposed and/or placed at the predetermined and/or desired angle relative to the target surface, as described above with reference to the support member 780. Moreover, the arrangement of the set of second portions 884 can, in some instances, provide lateral support to limit and/or substantially prevent rotating, tipping, wobbling, and/or any other undesired movement of the device 800 relative to the target surface.

Although not shown in in the transfer devices 100, 200, 300, 400, 500, 600, 700, and/or 800, any of the fluid transfer device described herein can include an internal support member configured to guide, shield, protect, and/or otherwise support, for example, the catheter disposed within the introducer. For example. FIG. 42 illustrates a fluid transfer device 900 according to an embodiment. The fluid transfer device 900 can be substantially the same in form and/or function as the fluid transfer device 200 described above with reference FIGS. 3-29 and, as such, portions of the transfer device 900 are not described in further detail herein.

The fluid transfer device 900 (also referred to herein as "transfer device" or "device") includes an introducer 910, a catheter 960, an actuator 970, and an internal support member 986. As described in detail above with reference, to the transfer device 200, the introducer 910 has a distal end portion that is coupled to a lock 940, which in turn, is configured to couple the transfer device 900 to, for example, an indwelling PIV and/or an extension set (e.g., a Y-adapter. T-adapter, or the like). The introducer 910 defines an inner volume 913 configured to receive and/or house at least a portion of the catheter 960, the actuator 970, and the internal support member 986. As described above, the actuator 970 is movably coupled to the introducer 910 and includes a first portion 971, a second portion 975, and a wall 977 coupling the first portion 971 to the second portion 975. The first portion 971 of the actuator 970 is disposed outside of the introducer 910. The second portion 975 of the actuator 970 is disposed within the inner volume 913 of the introducer 910 and is fixedly coupled to a distal end portion of the catheter 960. In this manner, a user can exert a force on the first portion 971 of the actuator 970 to move the catheter 960 between a first position (e.g., a proximal position), in which the catheter 960 is disposed within the introducer 910 and/or the lock 940, and a second position (e.g., a distal position), in which at least a portion of the catheter 960 extends distally beyond the lock 940, as described in detail above with reference to the transfer device 200.

As shown in FIGS. 42 and 43, the transfer device 900 also includes the internal support member 986 disposed within the inner volume 913 of the introducer 910 and about at least a portion of the catheter 960. The internal support member 986 can be any suitable shape, size, and/or configuration. For example, in this embodiment, the internal support member 986 is a substantially cylindrical tube having a diameter that allows the internal support member 986 to be disposed within the inner volume 913 (or a portion thereof). Moreover, the internal support member 986 is configured to surround and/or substantially enclose at least a portion of the catheter 960. In some embodiments, the internal support member 986 can support the catheter 960 to limit and/or substantially prevent undesired deflection and/or deformation of the catheter 960. For example, as described above with reference to the transfer device 300, in some embodiments, the catheter 960 can be configured to "clutch" or deflect in response to a distal end of the catheter 960 impacting an obstruction or the like. In such embodiments, disposing the internal support member 986 about at least a portion of the catheter 960 can limit an amount of deflection of the catheter 960 when transitioned to the "clutched" configuration. In some embodiments, such an arrangement can, for example, maintain the catheter 960 within the inner volume 913 of the introducer 910 (or a desired portion thereof). That is to say, the internal support member 986 can support the catheter 960 and/or otherwise limit an amount of deflection of the catheter 960 that may otherwise result in a portion of the catheter 960 extending outside of the inner volume 913 (e.g., via an actuator slot, track, or opening).

The internal support member 986 includes and/or defines a slit 987 that spirals and/or coils along a length of the internal support member 986, as shown in FIGS. 42 and 43. The second portion 975 of the actuator 970 can be disposed within the internal support member 986 and at least a portion of the wall 977 of the actuator 970 can extend through the slit 987 defined by the internal support member 986 (see e.g., FIG. 42). This arrangement of the actuator 970 and the internal support member 986 is such that when a user moves the actuator 970 along a length of the introducer 910, the second portion 975 of the actuator 970 and the catheter 960 are moved within the internal support member 986. With the wall 977 extending through the slit 987, the movement of the actuator 970 along the introducer 910 results in a rotation of the internal support member 986 as the wall 977 is advanced through the slit 987 (e.g., the spiraled or coiled slit). Said another way, the translational motion of the actuator 970 results in a similar translational motion of the catheter 960 and a rotational motion of the internal support member 986 about the catheter 960. Thus, the internal support member 986 can support at least a portion of the catheter 960 disposed within the introducer 910. Moreover, in some embodiments, the internal support member 986 can be configured to substantially maintain a sterility of the catheter 960 prior to use.

While the internal support member 986 is shown and described above as being a substantially cylindrical tube in which the catheter 960 is disposed, in other embodiments, a fluid transfer device can include any suitable internal support member. For example, FIG. 44 illustrates a fluid transfer device 1000 according to an embodiment. The fluid transfer device 1000 can be substantially the same in form and/or function as the fluid transfer device 900 described above with reference to FIGS. 42 and 43 and, as such, portions of the fluid transfer device 1000 are not described in further detail herein.

The fluid transfer device 1000 (also referred to herein as "transfer device" or "device") includes an introducer 1010, a catheter 1060, an actuator 1070, and an internal support member 1086. The introducer 1010 has a distal end portion that is coupled to a lock 1040, which in turn, is configured to couple the transfer device 1000 to, for example, an indwelling PIV and/or an extension set (e.g., a Y-adapter. T-adapter, or the like). The introducer 1010 defines an inner volume 1013 configured to receive and/or house at least a portion of the catheter 1060, at least a portion of the actuator 1070, and the internal support member 1086. As described above, the actuator 1070 is movably coupled to the introducer 1010 and includes a first portion 1071 disposed outside of the introducer and a second portion 1075 disposed in the inner volume 1013 and fixedly coupled to the catheter 1060. In this manner, a user can exert a force on the first portion 1071 of the actuator 1070 to move the catheter 1060 between a first position (e.g., a proximal position), in which the catheter 1060 is disposed within the introducer 1010 and/or the lock 1040, and a second position (e.g., a distal position), in which at least a portion of the catheter 1060 extends distally beyond the lock 1040, as described in detail above.

The transfer device 1000 can differ from the transfer device 900, however, in the arrangement of the internal support member 1086. For example, in the embodiment shown in FIG. 44, the internal support member 1086 can be formed of a relatively flexible material and configured and/or arranged as, for example, a bellows. The internal support member 1086 is disposed in the inner volume 1013 between the second portion 1075 of the actuator 1070 and an interior distal surface of the introducer 1010 at least partially defining a distal end of the inner volume 1013 such that at least a portion of the catheter 1060 is movably disposed within the internal support member 1086. With the internal support member 1086 arranged and/or configured as a bellows, movement of the actuator 1070 results in a compression, deformation, and/or collapse of the internal support member 1086. That is to say, movement of the actuator 1070 from a proximal position toward a distal position compresses the bellows formed by and/or otherwise included in the internal support member 1086. Conversely, when the actuator 1070 is moved from a distal position toward the proximal position, the bellows formed by and/or otherwise included in the internal support member 1086 can expand and/or reconfigure to a pre-deformed configuration. Thus, the internal support member 1086, for example, can support the catheter 1060 (e.g., when the catheter 1060 transitions to a "clutched" configuration) and/or can fluidically isolate at least a portion of the catheter 1060 (e.g., to substantially maintain the sterility of the catheter 1060), as described above with reference to the internal support member 986.

While the internal support member 1086 is shown and described above as forming a bellows or the like in which at least a portion of the catheter 1060 is disposed, in other embodiments, a fluid transfer device can include any suitable internal support member. For example. FIG. 45 illustrates a fluid transfer device 1100 according to an embodiment. The fluid transfer device 1100 can be substantially the same in form and/or function as the fluid transfer device 900 described above with reference FIGS. 42 and 43. Thus, portions of the fluid transfer device 1100 are not described in further detail herein.

The fluid transfer device 1100 (also referred to herein as "transfer device" or "device") includes an introducer 1110, a catheter 1160, an actuator 1170, and an internal support member 1186. The introducer 1110 has a distal end portion that is coupled to a lock 1140, which in turn, is configured to couple the transfer device 1100 to, for example, an indwelling PIV and/or an extension set (e.g., a Y-adapter, T-adapter, or the like). The introducer 1110 defines an inner volume 1113 configured to receive and/or house at least a portion of the catheter 1160, the actuator 1170, and the internal support member 1186. As described above, the actuator 1170 is movably coupled to the introducer 1110 and includes a first portion 1171 disposed outside of the introducer and a second portion 1175 disposed in the inner volume 1113 and fixedly coupled to the catheter 1160. In this manner, a user can exert a force on the first portion 1171 of the actuator 1170 to move the catheter 1160 between a first position (e.g., a proximal position), in which the catheter 1160 is disposed within the introducer 1110 and/or the lock 1140, and a second position (e.g., a distal position), in which at least a portion of the catheter 1160 extends distally beyond the lock 1140, as described in detail above.

The transfer device 1100 can differ from the transfer device 900, however, in the arrangement of the internal support member 1186. For example, in the embodiment shown in FIG. 45, the internal support member 1186 can be formed of a relatively thin and flexible material that is disposed in, for example, a zig-zag configuration (e.g., a set of wall segments arranged in alternating angular orientations). The internal support member 1186 is disposed within the inner volume 1113 of the introducer 1110 between a distal surface at least partially defining a distal end of the inner volume 1113 and the second portion 1175 of the actuator 1170. In other embodiments, the internal support member 1186 can extend along only a portion of the inner volume disposed between the actuator 1170 and the distal surface.

The catheter 1160 is disposed within and/or extends through an opening or hole defined in each wall segment (see e.g., FIG. 45). In some embodiments, the size and/or diameter of the opening or hole defined in each wall segment can be "tuned" and/or set to adjust the amount of support provided to the catheter 1160. For example, in some embodiments, the opening or hole can be similar to and/or slightly larger than the outer diameter of the catheter 1160. In such embodiments, a relatively tight tolerance between the size and/or diameter of the opening and the size and/or outer diameter of the catheter 1160 can result in a relatively high level of support, which in turn, can reduce an amount of deflection and/or deformation of the catheter 1160, for example, when the catheter 1160 is transitioned from the unclutched configuration to the clutched configuration. In other embodiments, the opening and/or hole defined by each wall segment of the internal support member 1186 can be larger than an outer diameter of the catheter 1160 (e.g., a relatively large tolerance therebetween). In such embodiments, the larger size and/or diameter of the opening can allow the catheter 1160 to deflect relative to the internal support member 1186. Thus, in some embodiments, an increase in the size and/or diameter of the openings in the internal support member 1186 can result in an increased range of motion of the catheter 1160 (e.g., an increase in an amount of deflection and/or deformation when the catheter 1160 is transitioned from the unclutched configuration to the clutched configuration.

In some embodiments, the internal support member 1186 can be formed of a material having sufficient flexibility to bend, deform, flex, and/or otherwise reconfigure. For example, when the actuator 1170 is moved along the introducer 1110, the second portion 1175 of the actuator 1170 can compress and/or fold the interior support member 1185 (e.g., reduce an angle defined between adjoining wall segments). In addition, at least a portion of the internal support member 1186 can be configured to bend and/or flex in response to the catheter 1160 being transitioned to the "clutched" configuration, while substantially limiting an amount of deflection of the catheter 1160 that may otherwise result in a portion of the catheter 1160 extending outside of the introducer 1110 (as described above with reference to the internal support member 986). Thus, the internal support member 1186 can support at least a portion of the catheter 1160 disposed within the introducer 1110.

While the internal support member 1186 is shown as extending along substantially the entire length of the catheter 1160, in other embodiments, an internal support member may extend along any suitable portion of a catheter (e.g., less than substantially the entire length of the catheter). While the internal support member 1186 is described above as being formed of a relatively thin and flexible material having the set of wall segments arranged in alternating angular orientations, in other embodiments, an internal support member can be any suitable shape, size, and/or configuration. For example, in some embodiments, a fluid transfer device can include a spring (e.g., a coil spring) or the like disposed within an inner volume of the introducer and about at least a portion of a catheter. In such embodiments, the spring or the like can support at least a portion of the catheter in a manner substantially similar to that described above with reference to the internal support members 986, 1086, and/or 1186.

In other embodiments, an internal support member can be integrally formed with and/or otherwise coupled to the catheter. For example, in some embodiments, one or more portions of a catheter can be formed as a support member. Such portions, for example, can have an increased wall thickness and/or can be formed of a different constituent material. In other embodiments, an internal support member can be selectively coupled to a catheter. For example, in some embodiments, a catheter can include a set of rings or beads that can be movably coupled to and/or disposed along a length of the catheter. In some embodiments, the rings and/or beads can be evenly and/or uniformly spaced or can be randomly and/or unevenly spaced. In some embodiments, the rings and/or beads can be configured to move along a length of the catheter in response to an actuation of the actuator (e.g., movement of the catheter). For example, in some embodiments, each ring and/or bead can be coupled to the catheter and can be temporarily maintained in a substantially fixed position. In some instances, as the catheter is advanced in the distal direction, the rings and/or beads can be moved such that the rings and/or beads bunch and/or slide into a position along, for example, the proximal end portion of the catheter. As such, the rings and/or beads can be configured to increase an amount of support provided to the catheter as the catheter is advanced in the distal direction (e.g., as a spacing between the rings and/or beads is reduced).

In still other embodiments, an introducer can include an internal support member formed of and/or otherwise having deformable tape and/or foam disposed along an inner surface of the catheter (e.g., an upper inner surface). In such embodiments, the tape and/or foam can be configured to compress, bend, flex, deform, and/or otherwise reconfigure as the actuator and/or catheter is relative thereto. For example, in some embodiments, foam or the like can be disposed between the actuator and the distal surface of the inner volume of the introducer and can be compressed (e.g., axially) in response to a distal movement of the actuator. In other embodiments, the introducer can include foam or the like along an upper surface of the inner volume and can be deformed, displaced, deflected, and/or compressed, for example, in a transverse direction at or near a position of the actuator. Moreover, as the actuator is advanced along a length of the introducer, a portion of the foam can be configured to return to an undeformed configuration as the actuator is moved relative to the portion. Thus, a portion of the foam that is proximal to the actuator (or a portion thereof) can be in an undeformed configuration and a portion of the foam that is distal to the actuator (or the portion thereof) can be in an undeformed configuration. That is to say, the actuator displaces a predetermined and/or defined portion of the foam as the actuator is moved along the introducer. In some embodiments, the foam can limit and/or reduce an open or unoccupied portion of the inner volume, which in turn, can result in a limited and/or reduced range of motion of the catheter (e.g., when transitioning from an unclutched configuration to a clutched configuration). In some embodiments, the deformation of the foam in response to the movement of the actuator can further limit and/or reduce the open or unoccupied portion of the inner volume, which in turn, can result in an increased amount of support provided to the catheter (e.g., a decreased range of motion).

Although some of the fluid transfer devices described herein are not shown explicitly with a peripheral intravenous line (PIV), it should be understood that any of the fluid transfer devices described herein can be coupled to any suitable peripheral intravenous line (PIV). In some instances, use of a PIV can include coupling the PIV to an IV extension set and/or an adapter (e.g., a single port adapter, a Y-adapter, a T-adapter, or the like). Thus, while some of the transfer devices are described herein as being coupled to a PIV, it should be understood that the transfer devices can be coupled to either a PIV or an adapter (e.g., extension set) coupled thereto based on the situation and/or configuration. The transfer devices can be configured to couple to any suitable commercially available PIV, adapter, and/or extension set. For example, while the first arm 243 and the second arm 250 of the lock 240 are shown (e.g., in FIGS. 13 and 14) and described above as having a given shape and/or configuration, in other embodiments, a lock can include a first arm and a second arm that have a size, shape, and/or configuration that can allow the lock to be coupled to various PIVs, adapters, and/or extension sets. By way of example, in some embodiments, the arms of a lock can be rounded, bent, bowed, widened, and/or the like to allow the lock to receive a portion of any suitable PIV, adapter, and/or extension set. In some embodiments, the arrangement of the arms 243 and 250 of the lock 240 can allow the lock 240 to be rotated substantially 360° about any suitable PIV, adapter, and/or extension set when coupled thereto. Moreover, in some embodiments, the ability to rotate the lock 240 to, for example, place the arms of the lock 240 in a predetermined position such that placing a surface of the arm 243 or the arm 250 in contact with a surface disposes the device 200 at a predetermined and/or desired angle relative to the surface, as described above with reference to the device 400 illustrated in FIGS. 35 and 36.

While the proboscis 242 is shown and described above as having a particular size and/or shape, in other embodiments, a lock can include a proboscis that has any suitable length (e.g., longer or shorter than the proboscis 242), width (e.g., wider or narrower than the proboscis 242), and/or shape (e.g., curved, tapered, flared, etc.). In some embodiments, a proboscis can have a surface finish or feature such as one or more threads, flighting (e.g., an auger flighting), ribs, grooves, and/or the like. In some embodiments, the proboscis 242 can have a diameter and/or length that is associated with and/or at least partially based on one or more internal dimensions of an extension set, PIV, and/or the like. In other words, in some embodiments, the devices described herein can be configured for use with an extension set and/or PIV having one or more desired internal dimensions such as, for example, an internal diameter of a lumen defined by the extension set, a length of the lumen, and/or the like. For example, in some embodiments, an extension set can define a lumen, at least a portion of which has an inner diameter of about 1.0 millimeter (mm) to about 1.6 mm. In other embodiments, an extension set can define a lumen (or portion thereof) having a diameter that is associated with and/or slightly larger than an outer diameter of the catheter configured to be inserted therethrough (e.g., a diameter that is slightly larger than a diameter of a 30 gauge catheter or about 0.20 mm).

In some embodiments, such an extension set having the one or more desired internal dimensions (inner diameters) can act as a guide or the like configured to guide the catheter 260 through the extension set and/or at least a portion of the PIV substantially without bending, kinking, breaking, and/or substantially without getting stuck. More specifically, in some embodiments, an extension set can couple to a PIV hub or the like such that a distal end portion of the extension set extends through a portion of the PIV hub or basket. In such embodiments, the extension set can define a lumen having an inner diameter of about 1.4 mm at a distal end portion thereof (e.g., the lumen can taper toward the distal end portion to approximately 1.4 mm in diameter or can have a substantially constant diameter of approximately 1.4 mm between its proximal end portion and its distal end portion). In such embodiments, the extension set can guide, for example, the distal end portion 262 of the catheter 260 through the extension set and the hub or basket of the PIV and into, for example, a vein of the patient substantially without impacting an obstruction or "snagging" on one or more portions of the extension set and/or PIV. In this manner, the extension set can be an adapter and/or guide that can allow the transfer device 200 to be used with any suitable PIV such as, for example, commercially available PIVs or the like.

In other embodiments, the extension set, PIV, and/or any of the devices described herein can include and/or can be coupled to an external guide member or the like that can be disposed between components. Such external guide members can be configured to direct a catheter as the catheter is advanced in a distal direction (as described in detail above). For example, in some embodiments, the guide member can have a taper and/or can be funnel shaped having a larger diameter, for example, at a proximal end portion and a smaller diameter, for example, at a distal end portion. In some embodiments, such a guide member can be disposed between an introducer of any of the devices described herein and an extension set. In other embodiments, such a guide member can be disposed between an extension set and a PIV. In still other embodiments, such a guide member can be disposed between the introducer of any of the devices described herein and a PIV. In still other embodiments, any of the devices described herein can include and/or can be coupled to one or more guide members having any suitable configuration.

The embodiments described herein can be used to transfer fluid from a patient or to the patient by accessing a vein via an indwelling PIV. As described above, the transfer devices 100 and/or 200, for example, can be manipulated to place a distal surface of a catheter at a predetermined and/or desired distance from a distal surface of the PIV. In some instances, the embodiments described herein allow for efficient blood draw while maintaining the integrity of the sample. While extracting blood, the transfer devices 100 and/or 200 can be configured to receive and/or produce a substantially laminar (e.g., non-turbulent or low turbulent) flow of blood through the transfer device 100 and/or 200, respectively, to reduce and/or substantially prevent hemolysis of the blood as the blood flows through the transfer devices 100 and/or 200, respectively.

In some instances, when a transfer device such as those described herein is used to collect a sample volume of blood (e.g., a blood culture) it may be desirable to occlude and/or otherwise block the lumen of the catheter as the catheter is inserted through an indwelling PIV and into the vein. For example, in some embodiments, the transfer device 200 can be used to collect a volume of blood. In such embodiments, the lock 240 of the transfer device 200 can be coupled to an indwelling PIV and a fluid source can be coupled to the coupler 269 of the secondary catheter 265. In some embodiments, for example, the fluid source can be a squeezable ball or bulb and/or suitable form of fluid reservoir and pump (e.g., a syringe and/or the like). The fluid source can contain, for example, saline or the like. Thus, with the fluid source coupled to the coupler 269, the fluid source is placed in fluid communication with the lumen 268 defined by the secondary catheter 265, which in turn, places the fluid source in fluid communication with the lumen 263 defined by the catheter 260.

In some embodiments, the fluid source can be actuated or the like to release a flow of fluid (e.g., saline) through the catheters 260 and 265, thereby flushing the lumens 263 and 268, respectively. Once flushed, the catheter 260 can be, for example, placed in a fluidic or hydraulic locked configuration and can be advanced to its second position (as described in detail above). In other embodiments, the fluid source can be actuated or the like (e.g., a squeeze bulb can be squeezed) to release a flow of fluid such that a substantially continuous flow of the fluid elutes from the catheter 260. With the fluid eluting from the catheter 260, the transfer device 200 can be actuated to advance the catheter 260 to its second position (as described above). In this manner, flushing the lumens 263 and 268 of the transfer device 200 prior to and/or during the advancement of the catheter 260 can limit and/or can substantially prevent contaminants from entering the fluid flow path defined by the lumens 263 and 268 (e.g., can be fluidically and/or hydraulically locked).

In some instances, once the catheter 260 is advanced to its second position, the fluid source can be, for example, reversed or the like such that a reservoir of the fluid source receives a flow of fluid. For example, in some instances, a squeeze ball or bulb can be actuated (squeezed), which in turn, reduces a volume of the squeeze ball or bulb as a flow of the fluid contained therein is released. In some instances, after the catheter 260 is placed in its second position, the force can be removed from the squeeze ball or bulb, which in turn, increases the volume of the squeeze ball or bulb. The increase of volume produces and/or results in a suction force, which in some instances, can be operable to draw any remaining saline and a volume of blood into the volume defined by the squeeze ball or bulb. As such. "reversing" the fluid source or the like can remove any remaining saline and can prime the transfer device 200. After priming the transfer device 200, any suitable fluid reservoir can be coupled to the coupler 269 such that a flow of clean blood is transferred from the vein and into the fluid reservoir.

While the squeeze ball or bulb is described above, it should be understood that any suitable fluid reservoir and/or pump can be used to flush and/or prime any of the transfer devices described herein. While the embodiments are described above as using a fluid such as saline to flush and/or prime the catheter and/or transfer device, in other embodiments, a catheter and/or transfer device can be flushed and/or primed via any suitable compressible fluid, incompressible fluid, and/or the like. In other embodiments, a gas such as air or any suitable inert gas can be used to form a pneumatic lock, flush, and/or prime. In still other embodiments, a guide wire and/or any other suitable occluding device can be disposed in the lumen of the catheter to limit and/or substantially prevent fluid from entering the lumen as the catheter is advanced to a desired position within the vein of a patient. In some such embodiments, an occluding device can include, for example, one or more portions configured to dissolve over a predetermined period, in response to a given temperature, and/or in response to fluid contact. In other embodiments, an occluding device and/or the like can include a deformable member, a shape memory or changing component (e.g., nickel-titanium alloy (nitinol)), a reversible valve (e.g., a mechanical valve configured to transition in response to a force or pressure or an electrical valve configured to transition in response to a flow of electric current), and/or any other suitable member.

Although not shown, any of the transfer devices described herein can include and/or can be coupled to a flash chamber or the like configured to receive, for example, a first volume of blood (e.g., a pre-sample of blood). In some embodiments, a flash chamber can be coupled to the coupler 269 of the secondary catheter 295 of the transfer device 200 to receive the first volume of blood. In other embodiments, any suitable portion of the transfer device 200 can form a flash chamber or the like configured to at least temporarily store the first volume of blood. In such embodiments, the first volume of blood can flow through, for example, a one-way seal such as a sponge seal or the like and into the flash chamber. The arrangement of the seal can be such that once the seal is wetted (e.g., with blood), the flow of the first volume of blood stops. Once a desired amount of blood is transferred into the flash chamber (e.g., the first volume), the transfer device 200 can be manipulated to transfer a second volume (e.g., a sample volume) of blood to a fluid reservoir (e.g., a sample reservoir).

While the embodiments described herein can be used in a variety of settings (ER, in-patient, etc.), the following scenario of withdrawing a sample volume of blood from a patient is provided by way of example. In some instances, for example, a peripheral intravenous line and/or catheter (PIV) is inserted into a vein of a patient following standard guidelines and an extension set and/or adapter is attached. The PIV can remain within the vein for an extended period and can provide access to the vein for the transfer of fluids (e.g., saline, blood, drug compounds, etc.) to the patient. When it is time to draw blood, a user (e.g., nurse, physician, phlebotomist, and/or the like) can stop the transfer of fluid to the patient, if it is transferring fluid, for approximately 1-5 minutes to allow the fluid to disperse from the blood-drawing site. To draw the blood sample, the user attaches a transfer device (e.g., the transfer devices 100 and/or 200) to a port and/or suitable portion of the extension set and/or adapter and transitions the transfer device to from a first configuration (e.g., a storage configuration) to a second configuration, in which a portion of a catheter included in the transfer device extends through the peripheral IV and into the vein.

As described in detail above with reference to the transfer device 200, an end of the catheter can be disposed at a predetermined and/or desired distance from an end of the PIV when the transfer device is in the second configuration to place the catheter in fluid communication with a portion of the vein that receives an unobstructed and/or uninhibited flow of blood. For example, the end of the catheter can be in a distal position relative to the end portion of the PIV and at least one branch vessel, valve, and/or the like in fluid communication with the vein. Once the catheter is in the desired position, the user can attach one or more negative pressure collection containers, tubes, and/or syringes to the transfer device to extract a volume of blood. In some instances, the volume of blood can be a first volume of blood that can be discarded and/or at least temporarily stored apart from a subsequent sample volume of blood (e.g., typically a volume of about 1-3 milliliters (mL) but up to 8-10 mL of blood can be a "waste" or "pre-sample" volume). In some instance, the waste volume can include contaminants, non-dispersed residual fluids, and/or the like. After the collective of the waste volume, the user can couple one or more negative pressure containers (e.g., sample containers) to the transfer device to collect a desired blood sample volume. Once the sample volume is collected, the transfer device can be transitioned from the second configuration toward the first configuration and/or a third configuration (e.g., a "used" configuration). The transfer device can then be decoupled from the extension set and/or adapter and safely discarded. In some instances, after collecting the sample volume but prior to transitioning the transfer device from the second configuration, the waste or pre-sample volume, for example, can be reinfused into the vein.

As described above, in some instances, the transfer devices described herein can be coupled to a fluid reservoir configured to receive a volume of bodily fluid (e.g., blood). In some instances, such a fluid reservoir can be a negative pressure container such as, for example, a Vacutainer® or the like. In some instances, however, it may be desirable to limit and/or control a rapid change in pressure through a transfer device and/or in a vein, which may otherwise result in hemolysis of a blood sample or portion thereof, a collapsed or "blown" vein, and/or the like. Accordingly, in some embodiments, any of the transfer devices described herein can be configured to modulate a negative pressure exerted therethrough.

For example, as described in detail above, the transfer device 200 includes a secondary catheter 265 that is in fluid communication with the catheter 260 and that includes a coupler 269 configured to couple the transfer device 200 to a fluid reservoir (e.g., a negative pressure reservoir). In some embodiments, the secondary catheter 265 can be configured to modulate a negative pressure exerted through the transfer device 200. For example, the secondary catheter 265 can be formed of a relatively flexible polymer material and/or the like that can allow the secondary catheter 265 to bend, flex, deform, and/or otherwise reconfigure in response to an applied force. Moreover, in some embodiments, the catheter 260 can have a stiffness or durometer that is greater than a stiffness or durometer of the secondary catheter 265. In some instances, when the secondary catheter 265 is exposed to the negative pressure differential, the lumen 268 defined by the secondary catheter 265 is exposed to a rapid decrease in pressure, which in turn, exerts a suction force within the lumen 268 that draws the walls of the secondary catheter 265 inward, thereby reducing an inner diameter of the secondary catheter 265. As such, reducing the diameter of the lumen 268 of the secondary catheter 265 results in a modulated and/or reduced suction force being exerted through the lumen 268 and on or in the lumen 263 of the catheter 260. Likewise, reducing the amount and/or magnitude of the suction force being exerted through the lumen 263 of the catheter 260, in turn, modulates and/or reduces a magnitude of the suction force that is exerted on or in the vein. Thus, a negative pressure differential experienced by or in the vein that might otherwise be sufficient to collapse the vein is reduced.

Furthermore, as bodily fluid (e.g., blood) is transferred through the transfer device 200 and into the negative pressure reservoir, a negative pressure differential between the reservoir and the vein is reduced. In other words, the negative pressure or suction force exerted by the negative pressure reservoir is reduced as a volume of blood is transfer therein. Said another way, the negative pressure differential is equalized as a volume of blood is transferred into the negative pressure reservoir. In some embodiments, the reduction in the magnitude of the negative pressure and/or the suction force exerted by the negative pressure reservoir can result in the secondary catheter 265 transitioning toward its undeformed configuration (i.e., the configuration prior to being exposed to the negative pressure). That is to say, as the magnitude of the negative pressure and/or negative pressure differential is reduced, a diameter of the lumen 268 defined by the secondary catheter 265 can increase or can return to a non-reduced diameter, which in turn, can increase a fluid flow rate therethrough. Thus, selectively modulating the negative pressure transferred through the secondary catheter 265 can result in a reduction in flow rate through the secondary catheter 265 when there is a large pressure differential (e.g., due to the reduction in the diameter of the lumen) and can result in an increase in flow rate through the secondary catheter 265 as the pressure differential is equalized (e.g., due to the increase in the diameter of the lumen).

In some embodiments, the arrangement and/or configuration of the secondary catheter 265 can be "tuned" and/or controlled to modulate the negative pressure exerted through the lumen. For example, the secondary catheter 265 can be formed of a material having sufficient flexibility to allow the secondary catheter 265 to deform in a desired manner when exposed to a negative pressure. In other embodiments, the walls of the secondary catheter 265 can have a thickness that is sufficiently thin to allow the walls to deform when exposed to the negative pressure. Moreover, in some embodiments, the length and/or an inner diameter of the secondary catheter 265 can be configured, for example, to reduce a fluid flow rate therethrough. In still other embodiments, any combination of flexibility, wall thickness, length, diameter, and/or the like can be used to collectively control and/or modulate a negative pressure exerted therethrough. In yet other embodiments, a negative pressure and/or the like can be modulated in response to a change in temperature of the secondary catheter 265. For example, in some instances, a temperature of the secondary catheter 265 is increased as the warm blood begins to flow therethrough. In some instances, the increase in temperature causes a relaxation of the diameter (e.g., an increase in inner diameter) and thus accelerates a flow of the blood as the negative pressure is decreased over the same period of time. In some instances, a cooling of the secondary catheter 265 can result in a constriction and/or reduction in the inner diameter of the secondary catheter 265.

In some instances, the transfer devices described herein can be assembled during one or more manufacturing processes and packaged in a pre-assembled configuration. For example, in some instances, the transfer device 200 can be assembled by coupling the catheter 260 and the secondary catheter 265 to the actuator 270; positioning the catheter 260, secondary catheter 265, and actuator 270 relative to the first member 220 or second member 230 of the introducer 210; coupling the first member 220 and the second member 230 to form the introducer 210 with the actuator 270 and at least a portion of the catheter 260 and secondary catheter 265 disposed in the inner volume 213 of the introducer 210; and coupling the lock 240 to the introducer 210. In some instances, the assembly of the transfer device 200 can be performed in a substantially sterile environment such as, for example, an ethylene oxide environment, or the like. In other embodiments, the transfer devices described herein can be packaged in a non-assembled configuration (e.g., a user can open the package and assemble the components to form the transfer device). The components of the transfer devices can be packaged together or separately. In some embodiments, the transfer devices can be packaged with, for example, a PIV, an extension set, a Y-adapter or T-adapter, and/or any other suitable component.

Any of the transfer devices described herein can be configured such that at least a portion of the catheter is biased and/or selectively deflected as the catheter is advanced from its first position to its second position, as described in detail above with reference to the device 300 shown in FIGS. 31-34. Moreover, a device having such an arrangement can be configured such that the biasing or selective deflection of the catheter results in a predictable and/or desired deflection, deformation, and/or reconfiguration of at least a portion of the catheter in response to a distal end portion of the catheter impacting an obstruction as the catheter is advanced from its first position to its second position. In other words, any of the devices described herein can be configured to "clutch" (e.g., deflect in a desired or predetermined manner) in response to the catheter impacting an obstruction.

Figure 46:
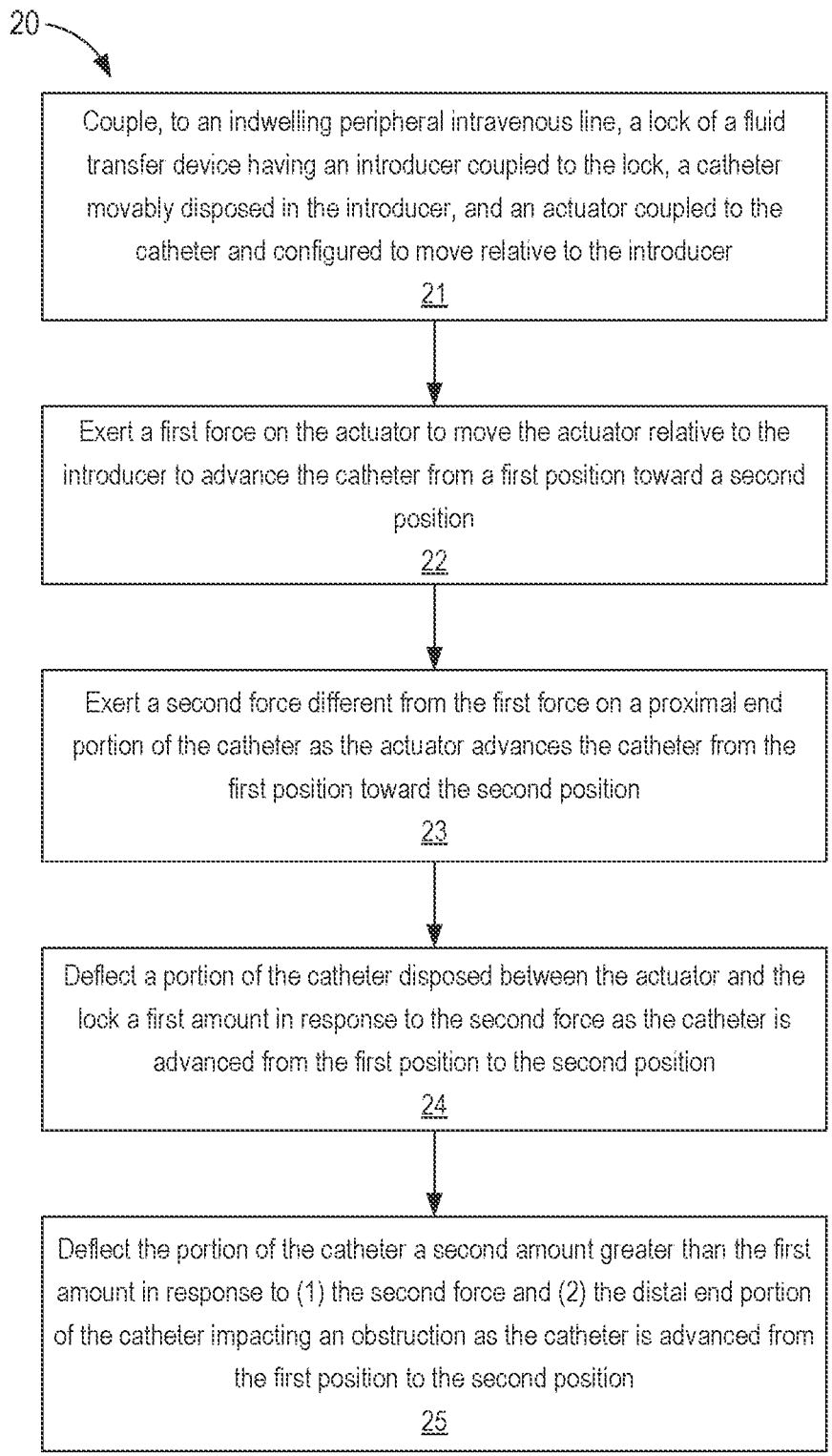
FIG. 46 is a flowchart illustrating a method of using a fluid transfer device according to an embodiment.

For example, FIG. 46 is a flowchart illustrating a method 20 of using such a fluid transfer device according to an embodiment. As described above with reference to the device 300, the fluid transfer device (also referred to herein as "device") can include an introducer, a catheter, and an actuator. The introducer can have a distal end portion that includes a lock configured to couple to a vascular access device. The catheter can be at least temporarily disposed within the introducer and can be coupled to a portion of the actuator. The actuator, in turn, can be movably coupled to the introducer and configured to move the catheter relative to the introducer, as described below.

As described above, the device can be used to transfer fluid to or from a patient. More particularly, in this example, the device can be configured to transfer a volume of bodily fluid (e.g., blood) from the vasculature of the patient to a fluid collection device such as a reservoir, syringe, evacuated container, and/or the like configured to be placed in fluid communication with the catheter. Accordingly, the method 20 includes coupling the lock of the device to an indwelling peripheral intravenous line (PIV), at 21. In other words, the lock is coupled to a PIV at least partially disposed within the vasculature of the patient.

A first force is exerted on the actuator to move the actuator relative to the introducer to advance the catheter from a first position to a second position, at 22. For example, the actuator can be movably coupled to the introducer and can include a first portion disposed outside of the introducer and a second portion disposed inside of the introducer and coupled to a proximal end portion of the catheter. As such, the user can engage the device and can exert the first force (e.g., with his or her finger or thumb) to move the actuator relative to the introducer. As described above with reference to at least the devices 200 and/or 300, the catheter is disposed within the introducer when in the first position and is advanced toward the second position to place a distal end portion of the catheter is in a distal position relative to the introducer (e.g., outside of and distal to the introducer).

A second force different from the first force is exerted on the proximal end portion of the catheter as the actuator advances the catheter from the first position toward the second position, at 23. As described above with reference to the device 300, for example, the arrangement of the actuator and the introducer can be such that the first portion of the actuator is in contact with an outer surface of the introducer. In some embodiments, the contact between the first portion of the actuator and the outer surface of the introducer can be sufficient to tilt or angle the actuator relative to the introducer such that a longitudinal axis of the actuator that would otherwise be parallel to a longitudinal axis of the introducer is instead nonparallel to the longitudinal axis of the introducer. In such embodiments, the contact between the first portion of the actuator and the outer surface of the introducer, in turn, results in the second portion of the actuator exerting the second force on the proximal end portion of the catheter. Moreover, the second force has a magnitude and a direction that are different from a magnitude and direction, respectively, of the first force.

As described above with reference to the device 300, the catheter is at least partially disposed within the introducer such that a portion of the catheter is disposed between the actuator (coupled to the proximal end portion of the catheter) and the lock (configured to movably receive the catheter). The method 20 includes deflecting the portion of the catheter disposed between the actuator and the lock a first amount in response to the second force as the catheter is advanced from the first position to the second position, at 24. For example, the lock defines a lumen that movably receives the catheter. The lumen of the lock can define a longitudinal axis that is parallel to the longitudinal axis of the introducer. More particularly, in some embodiments, the longitudinal axis of lock can be coaxial with the longitudinal axis of the introducer. As described above, the contact between the first portion of the actuator and the outer surface of the introducer tilts or angles the actuator relative to the introducer such that the longitudinal axis of the actuator is nonparallel to the longitudinal axis of the introducer. With the second portion of the actuator being coupled to the proximal end portion of the catheter, the tilt or angle of the actuator (and/or the second force) similarly angles or tilts at least the proximal end portion of the catheter relative to the introducer. Thus, with the catheter disposed within the lumen of the lock (e.g., the distal end portion of the catheter when the catheter is in the first position) and with the proximal end portion of the catheter being coupled to the second portion of the actuator, the second force exerted on the proximal end portion of the catheter results in a deflection of the portion of the catheter that is disposed between the lock and the actuator (e.g., as described in detail above with reference to FIGS. 31 and 32). Moreover, the deflection of the portion of the catheter is operable to bias the catheter and/or otherwise pre-load or pre-stress the catheter in a predetermined and/or desired manner.

The portion of the catheter disposed between the lock and the actuator is deflected a second amount greater than the first amount in response to (1) the second force and (2) the distal end portion of the catheter impacting an obstruction as the catheter is advanced from the first position to the second position, at 25. For example, in some instances, as the catheter is advanced from the first position toward the second position, the distal end of the catheter can impact an obstruction such as, for example, a portion of the hub of the PIV, a bend or kink in the PIV catheter, a clot or debris within the PIV or the vasculature of the patient, a wall or other anatomic structure of the vasculature and/or the like. As such, the obstruction can resist and/or exert a reaction force on the distal end of the catheter that can limit and/or prevent further advancement (e.g., distal movement) of the catheter. In some devices in which the portion of the catheter is not deflected the first amount (described above at 24), the first force exerted on the actuator can be transferred through the actuator and catheter, which in turn, can result in the distal end portion of the catheter becoming damaged, kinked, bent, broken, etc. in response to the impact. In other instances, the distal end of the catheter may puncture the wall or anatomic structure of the vasculature in response to the impact therebetween. In still other instances, the distal end portion of the catheter may damage or puncture a portion of the PIV in response to an impact therebetween.

The use of the device according to the method 20, however, is such that the impact between the distal end portion of the catheter and the obstruction is operable to deflect the second portion of the catheter the second amount, as described in detail above with reference to the device 300 (see e.g., FIGS. 33 and 34). Accordingly, at least a portion of the first force otherwise being exerted by the distal end of the catheter on the obstruction is transferred to the biased, pre-loaded, and/or pre-stressed portion of the catheter disposed between the lock and the actuator, which in turn, is operable to deflect the portion of the catheter the second amount. The arrangement of the device is such that the catheter deflects the second amount in a predictable, predetermined, and/or desired manner, which in turn, limits and/or substantially prevents damage to the catheter, the device, the PIV, and/or the vasculature of the patient. In other words, the arrangement of the device is such that the catheter is "clutched" in response to the distal end portion of the catheter impacting an obstruction as the catheter is advanced from the first position to the second position. Moreover, the device can be configured such that after "clutching" or deflecting of the catheter, the user can reduce a magnitude of the first force exerted on the actuator which in turn, can allow the catheter to "unclutch" and/or otherwise reconfigure to reduce an amount of the second deflection. In some instances, such reconfiguring can, for example, allow the distal end portion of the catheter to be repositioned relative to the obstruction, which in some instances, can allow the distal end portion to be advanced beyond the obstruction, which was previously limited and/or prevented due to the impact therebetween. Thus, the method 20 can be used to advance the catheter while reducing, limiting, and/or substantially preventing damage to the device, the PIV, and/or the vasculature of the patient. Moreover, in some instances, once the catheter is placed in the second position, the device can be used to aspirate a volume of bodily fluid (e.g., blood) as described in detail above with reference to specific embodiments.

While various embodiments have been described above, it should be understood that they have been presented by way of example only, and not limitation. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above.

While the embodiments have been particularly shown and described, it will be understood that various changes in form and details may be made. For example, while the transfer device 200 is shown and described above as including the catheter 260 and the secondary catheter 265, each of which being coupled to the actuator 270, in other embodiments, the transfer device 200 can include a single catheter (e.g., the catheter 260). For example, in some embodiments, at least the second portion 275 of the actuator 270 can be configured to transition between an open configuration and a closed configuration. In such embodiments, the catheter 260 can be placed in a desired position relative to the second portion 275 when the second portion 275 is in the open configuration. The second portion 275 can then be transitioned from the open configuration to the closed configuration to retain at least a portion of the catheter 260 within the opening 276 defined by the second portion 275. In such embodiments, the second portion 275 and the portion of the catheter 260 disposed in the opening 276 can form a friction fit operable to retain the catheter 260 in a fixed position relative to the actuator 270. Moreover, the friction fit defined between the second portion 275 of the actuator 270 and the catheter 260 can isolate a portion of the catheter 260 that is distal to the actuator 270 from a portion of the catheter 260 that is proximal to the actuator 270. Thus, the portion of the catheter 260 that is proximal to the actuator 270 can extend through the opening 217 and at least partially outside of the introducer 210 without contaminating the portion of the catheter 260 distal to the actuator 270.

Any of the aspects and/or features of the embodiments shown and described herein can be modified to affect the performance of the transfer device. For example, the ribs in the set of ribs 236 of the introducer 210 and the tab 273 of the actuator 270 can have any suitable shape, size, configuration, and/or arrangement to produce a desired set of characteristics associated with the movement of the actuator 270 relative to the introducer 210, as described above. By way of another example, any of the components of the transfer devices 100 and/or 200 can be formed from any suitable material that can result in a desired hardness, durometer, and/or stiffness of that component. For example, in some embodiments, at least the proboscis 242 of the lock 240 can be formed from a substantially rigid material such as a metal or hard plastic. In such embodiments, forming at least the proboscis 242 from the substantially rigid material can increase the structure support provided by the proboscis 242 to a PIV when the proboscis 242 is at least partially disposed therein. Similarly, the proboscis 242 can provide support to and/or otherwise can guide the catheter 260 when the catheter 260 is moved therethrough.

Where methods and/or schematics described above indicate certain events and/or flow patterns occurring in certain order, the ordering of certain events and/or flow patterns maybe modified. Additionally certain events may be performed concurrently in parallel processes when possible, as well as performed sequentially.

What is claimed is:

1. A method, comprising:
    coupling a lock of a fluid transfer device to an indwelling peripheral intravenous line, the fluid transfer device including an introducer having a distal end portion coupled to the lock, a catheter movably disposed in an inner volume defined by the introducer, and an actuator coupled to a proximal end portion of the catheter and configured to be moved relative to the introducer;
    exerting a first force on the actuator to move the actuator relative to the introducer to advance the catheter from a first position, in which a distal end portion of the catheter is disposed within a lumen defined by the lock, toward a second position;
    exerting a second force different from the first force on the proximal end portion of the catheter as the actuator advances the catheter from the first position toward the second position, the second force being exerted by the actuator on the proximal end portion of the catheter;
    deflecting a portion of the catheter a first amount in response to the second force as the catheter is advanced from the first position to the second position, the portion of the catheter being disposed between the actuator and the lock; and
    deflecting the portion of the catheter a second amount greater than the first amount in response to (1) the second force and (2) the distal end portion of the catheter impacting at least one of an obstruction within the peripheral intravenous line or a vascular wall as the catheter is advanced from the first position to the second position.

2. The method of claim 1, wherein the actuator includes a first portion disposed outside of the introducer and a second portion disposed within the introducer and coupled to the proximal end portion of the catheter,
    the first force being exerted by a user on the first portion of the actuator to move the actuator relative to the introducer, the second force being exerted by the second portion of the actuator on the proximal end portion of the catheter.

3. The method of claim 2, wherein the first portion of the actuator is in contact with an outer surface of the introducer, the contact between the first portion of the actuator and the outer surface of the introducer tilts the actuator relative to the introducer such that a longitudinal axis defined by the second portion of the actuator is nonparallel to a longitudinal axis defined by the introducer.

4. The method of claim 1, further comprising:
    placing the catheter in the second position such that the catheter extends through the lock to place the distal end portion of the catheter distal to the lock.

5. The method of claim 1, wherein the catheter defines a lumen extending through the proximal end portion and the distal end portion, the method further comprising:
    transferring a volume of fluid from a fluid source fluidically coupled to the catheter to the lumen of the catheter prior to exerting the first force on the actuator, the volume of fluid configured to (1) flush the lumen of the catheter and (2) fluidically obstruct the lumen of the catheter as the catheter is advanced from the first position toward the second position.

6. The method of claim 1, further comprising:
    coupling the lock to a support member prior to exerting the first force on the actuator, the support member configured to dispose the fluid transfer device at a predetermined angle relative to a target surface, the predetermined angle being substantially equal to an angle of insertion of the peripheral intravenous line.

* * * * *